United States Patent
Mitra et al.

(10) Patent No.: US 12,180,486 B2
(45) Date of Patent: Dec. 31, 2024

(54) COMPOSITIONS OF SELF-REPORTING TRANSPOSON (SRT) CONSTRUCTS AND METHODS FOR MAPPING TRANSPOSON INSERTIONS

(71) Applicants:Robi D. Mitra, St. Louis, MO (US); Arnav Moudgil, St. Louis, MO (US); Michael Nathaniel Wilkinson, St. Louis, MO (US); Zongtai Qi, St. Louis, MO (US)

(72) Inventors: Robi D. Mitra, St. Louis, MO (US); Arnav Moudgil, St. Louis, MO (US); Michael Nathaniel Wilkinson, St. Louis, MO (US); Zongtai Qi, St. Louis, MO (US)

(73) Assignee: Washington University, St. Louis, MO (US)

(*) Notice: Subject to any disclaimer, the term of this patent is extended or adjusted under 35 U.S.C. 154(b) by 1376 days.

(21) Appl. No.: 16/711,011

(22) Filed: Dec. 11, 2019

(65) Prior Publication Data
US 2020/0181626 A1    Jun. 11, 2020

Related U.S. Application Data

(60) Provisional application No. 62/777,995, filed on Dec. 11, 2018.

(51) Int. Cl.
| | |
|---|---|
| *C12N 15/63* | (2006.01) |
| *C12N 9/22* | (2006.01) |
| *C12N 15/10* | (2006.01) |
| *C12N 15/113* | (2010.01) |
| *C12N 15/90* | (2006.01) |

(52) U.S. Cl.
CPC .............. *C12N 15/635* (2013.01); *C12N 9/22* (2013.01); *C12N 15/102* (2013.01); *C12N 15/113* (2013.01); *C12N 15/907* (2013.01); *C12N 2310/11* (2013.01); *C12N 2310/20* (2017.05); *C12N 2310/3513* (2013.01)

(58) Field of Classification Search
CPC ...... C12N 15/635; C12N 9/22; C12N 15/102; C12N 15/113; C12N 15/907; C12N 2310/11; C12N 2310/20; C12N 2310/3513; C12N 2800/90; C12N 15/1082
See application file for complete search history.

(56) References Cited

FOREIGN PATENT DOCUMENTS

WO    WO-2018213886 A1 * 11/2018 ............ C12N 15/85

OTHER PUBLICATIONS

Balasubramanian et al., Multigene Expression in Stable CHO Cell Pools Generated with the piggyBac Transposon System. Biotechnol. Prog., 2016, vol. 32, No. 5 (Year: 2016).*
Sumiyoshi et al. 2009. Stable Transgene Expression in Primitive Human CD34þ Hematopoietic Stem=Progenitor Cells, Using the Sleeping Beauty Transposon System. Human Gene Therapy 20:1607-1626 (Year: 2009).*
Wu et al. 2014. PLE-wu, a new member of piggyBac transposon family from insect, is active in mammalian cells. Journal of Bioscience and Bioengineering vol. 118 No. 4, 359e366 (Year: 2014).*
Garg et al. 2014 The Hybrid Cytomegalovirus Enhancer/Chicken—Actin Promoter along with Woodchuck Hepatitis Virus Post-transcriptional Regulatory Element Enhances the Protective Efficacy of DNA Vaccines J Immunol (2004) 173 (1): 550-558 (Year: 2004).*
Angermueller C, Clark SJ, Lee HJ, Macaulay IC, Teng MJ, Hu TX, et al. Parallel single-cell sequencing links transcriptional and epigenetic heterogeneity. Nature Methods. Nature Publishing Group; 2016;13: 229-232. doi:10.1038/nmeth.3728.
Avey D, Sankararaman S, Yim AKY, Barve R, Milbrandt J, Mitra RD. Single-Cell RNA-Seq Uncovers a Robust Transcriptional Response to Morphine by Glia. Cell Reports. Cell Press; 2018;24: 3619-3629. e4. doi:10.1016/j.celrep.2018.08.080.
Balciunas et al. (2004) Enhancer trapping in zebrafish using the Sleeping Beauty transposon. Reference. BMC Genomics, vol. 5 (62).
Brandeis M, Frank D, Keshet I, Siegfried Z, Mendelsohn M, Nemes A, et al. Sp1 elements protect a CpG island from de novo methylation. Nature. Nature Publishing Group; 1994;371: 435-438. doi:10.1038/371435a0.
Brunner AL, Johnson DS, Kim SW, Valouev A, Reddy TE, Neff NF, et al. Distinct DNA methylation patterns characterize differentiated human embryonic stem cells and developing human fetal liver. Genome Res. Cold Spring Harbor Lab; 2009;19: 1044-1056. doi:10.1101/gr.088773.108.
Buenrostro, J. D. et al. Single-cell chromatin accessibility reveals principles of regulatory variation. *Nature* 523, 486-490, doi:10.1038/nature14590 (2015).
Cadinanos J, Bradley A. Generation of an inducible and optimized piggyBac transposon system. Nucl Acids Res. Oxford University Press; 2007;35: e87-e87. doi:10.1093/nar/gkm446.
Campbell JN, Macosko EZ, Fenselau H, Pers TH, Lyubetskaya A, Tenen D, et al. A molecular census of arcuate hypothalamus and median eminence cell types. Nature Neuroscience. 2017;20: 484-496. doi:10.1038/nn.4495.
Cao J, Cusanovich DA, Ramani V, Aghamirzaie D, Pliner HA, Hill AJ, et al. Joint profiling of chromatin accessibility and gene expression in thousands of single cells. Science. American Association for the Advancement of Science; 2018;33: eaau0730. doi:10.1126/science.aau0730.

(Continued)

*Primary Examiner* — Celine X Qian
*Assistant Examiner* — Tiffany Nicole Grooms

(57) ABSTRACT

Among the various aspects of the present disclosure is the provision of compositions and methods for mapping transposon insertions. Applications can include mapping the locations of self-reporting transposons (SRTs) from thousands of single cells in parallel, while simultaneously measuring mRNA abundance from the same single cells; analyzing genome-associated protein (GAP) (e.g., transcription factor) binding/interactions in a small number of cells in bulk, without single cell resolution; lineage tracing; or as an improved readout for transposon mutagenesis screens.

9 Claims, 69 Drawing Sheets

Specification includes a Sequence Listing.

(56) References Cited

OTHER PUBLICATIONS

Cao J, Packer JS, Ramani V, Cusanovich DA, Huynh C, Daza R, et al. Comprehensive single-cell transcriptional profiling of a multicellular organism. Science. American Association for the Advancement of Science; 2017;357: 661-667. doi:10.1126/science.aam8940.

Castillo-Hair SM, Sexton JT, Landry BP, Olson EJ, Igoshin OA, Tabor JJ. FlowCal: A User-Friendly, Open Source Software Tool for Automatically Converting Flow Cytometry Data from Arbitrary to Calibrated Units. ACS Synth Biol. American Chemical Society; 2016;5: 774-780. doi:10.1021/acssynbio.5b00284.

Cervera et al. (2016) Retrozymes are a unique family of non-autonomous retrotransposons with hammerhead ribozymes that propagate in plants through circular RNAs. Genome Biology vol. 17 (135).

Chen W, Jia Q, Song Y, Fu H, Wei G, Ni T. Alternative Polyadenylation: Methods, Findings, and Impacts. Elsevier; 2017;15: 287-300. doi:10.1016/j.gpb.2017.06.001.

Clark SJ, Argelaguet R, Kapourani C-A, Stubbs TM, Lee HJ, Alda-Catalinas C, et al. scNMT-seq enables joint profiling of chromatin accessibility DNA methylation and transcription in single cells. Nat Commun. Nature Publishing Group; 2018;9: 390. doi:10.1038/s41467-018-03149-4.

Coactivator condensation at super-enhancers links phase separation and gene control. Science. 2018;361: eaar3958. doi:10.1126/science.aar3958.

Cusanovich, D. A. et al. Multiplex single cell profiling of chromatin accessibility by combinatorial cellular indexing. *Science* 348, 910-914, doi:10.1126/science.aab1601 (2015).

Datlinger P, Rendeiro AF, Schmidl C, Krausgruber T, Traxler P, Klughammer J, et al. Pooled CRISPR screening with single-cell transcriptome readout. Nature Research; 2017;14: 297-301. doi:10.1038/nmeth.4177.

Davis RL, Weintraub H, Lassar AB. Expression of a single transfected cDNA converts fibroblasts to myoblasts. Cell. Cell Press; 1987;51: 987-1000. doi:10.1016/0092-8674(87)90585-X.

Dey SS, Kester L, Spanjaard B, Bienko M, van Oudenaarden A. Integrated genome and transcriptome sequencing of the same cell. Nat Biotechnol. Nature Publishing Group; 2015;33: 285-289. doi:10.1038/nbt.3129.

Ding S, Wu X, Li G, Han M, Zhuang Y, Xu T. Efficient transposition of the piggyBac (PB) transposon in mammalian cells and mice. Cell. 2005;122: 473-483. doi:10.1016/j.cell.2005.07.013.

Dixit A, Parnas O, Li B, Chen J, Fulco CP, Jerby-Arnon L, et al. Perturb-Seq: Dissecting Molecular Circuits with Scalable Single-Cell RNA Profiling of Pooled Genetic Screens. Cell. 2016;167: 1853-1866.e17. doi:10.1016/j.cell.2016.11.038.

Epicentre, An Illumina Company (2012). EZ-Tn5TM <T7/KAN-2> Promoter Insertion Kit, Cat. No. EZI03T7, Accessed from http://www.epibio.com/docs/default-source/protocols/ez-tn5-lt-t7-kan-2-gt-promoter-insertion-kit.pdf?sfvrsn=8 on Jun. 24, 2018.

Ernst J, Kheradpour P, Mikkelsen TS, Shoresh N, Ward LD, Epstein CB, et al. Mapping and analysis of chromatin state dynamics in nine human cell types. Nature. Nature Publishing Group; 2011;473: 43-49.

Fan X, Kim H-J, Bouton D, Warner M, Gustafsson J-A. Expression of liver X receptor β is essential for formation of superficial cortical layers and migration of later-born neurons. PNAS. National Academy of Sciences; 2008;105: 13445-13450. doi:10.1073/pnas.0806974105.

Fincher CT, Wurtzel O, de Hoog T, Kravarik KM, Reddien PW. Cell type transcriptome atlas for the planarian Schmidtea mediterranea. Science. American Association for the Advancement of Science; 2018;20: eaaq1736-757. doi:10.1126/science.aaq1736.

Fogarty NME, McCarthy A, Snijders KE, Powell BE, Kubikova N, Blakeley P, et al. Genome editing reveals a role for OCT4 in human embryogenesis. Nature. 2017;9: 346. doi:10.1038/nature24033.

Frith MC, Valen E, Krogh A, Hayashizaki Y, Carninci P, Sandelin A. A code for transcription initiation in mammalian genomes. Genome Res. Cold Spring Harbor Lab; 2008;18: 1-12. doi:10.1101/gr.6831208.

Gasperini M, Hill AJ, McFaline-Figueroa JL, Martin B, Kim S, Zhang MD, et al. A Genome-wide Framework for Mapping Gene Regulation via Cellular Genetic Screens. Cell. Cell Press; 2019. doi:10.1016/j.cell.2018.11.029.

Gogol-Doring A, Ammar I, Gupta S, Bunse M, Miskey C, Chen W, et al. Genome-wide Profiling Reveals Remarkable Parallels Between Insertion Site Selection Properties of the MLV Retrovirus and the piggyBac Transposon in Primary Human CD4+ T Cells. Molecular Therapy. 2016;24: 592-606. doi:10.1038/mt.2016.11.

Gonen N, Futtner CR, Wood S, Alexandra Garcia-Moreno S, Salamone IM, Samson SC, et al. Sex reversal following deletion of a single distal enhancer of Sox9. Science. American Association for the Advancement of Science; 2018;360: 1469-1471. doi:10.1126/science.aas9408.

Greil F, Moorman C, van Steensel B. DamID: Mapping of In Vivo Protein-Genome Interactions Using Tethered DNA Adenine Methyltransferase. DNA Microarrays, Part A: Array Platforms and Wet-Bench Protocols. Elsevier; 2006. pp. 342-359. doi:10.1016/S0076-6879(06)10016-6.

Gurdon JB. Cell Fate Determination by Transcription Factors. Essays on Developmental Biology, Part A. Elsevier; 2016. pp. 445-454. doi:10.1016/bs.ctdb.2015.10.005.

Hafler BP, Surzenko N, Beier KT, Punzo C, Trimarchi JM, Kong JH, et al. Transcription factor Olig2 defines subpopulations of retinal progenitor cells biased toward specific cell fates. PNAS. National Academy of Sciences; 2012;109: 7882-7887. doi:10.1073/pnas.1203138109.

Han X, Wang R, Zhou Y, Fei L, Sun H, Lai S, et al. Mapping the Mouse Cell Atlas by Microwell-Seq. Cell. Elsevier; 2018;172: 1091-1107.e17. doi:10.1016/j.cell.2018.02.001.

Hnisz D, Abraham BJ, Lee TI, Lau A, Saint-Andre V, Sigova AA, et al. Super-Enhancers in the Control of Cell Identity and Disease. Cell. 2013;155: 934-947. doi:10.1016/j.cell.2013.09.053.

Hwang B, Lee JH, Bang D. Single-cell RNA sequencing technologies and bioinformatics pipelines. Exp Mol Med. Nature Publishing Group; 2018;50: 96. doi:10.1038/s12276-018-0071-8.

Ivics Z, Hackett PB, Plasterk RH, Izsvak Z. Molecular Reconstruction of Sleeping Beauty, a Tc1-like Transposon from Fish, and Its Transposition in Human Cells. Cell. Cell Press; 1997;91: 501-510. doi:10.1016/S0092-8674(00)80436-5.

Johnson DS, Mortazavi A, Myers RM, Wold B. Genome-Wide Mapping of in Vivo Protein-DNA Interactions. Science. American Association for the Advancement of Science; 2007;316: 1497-1502. doi:10.1126/science.1141319.

Kalhor R, Kalhor K, Mejia L, Leeper K, Graveline A, Mali P, et al. Developmental barcoding of whole mouse via homing CRISPR. Science. American Association for the Advancement of Science; 2018;113: eaat9804. doi:10.1126/science.aat9804.

Karaiskos N, Wahle P, Alles J, Boltengagen A, Ayoub S, Kipar C, et al. The *Drosophila* embryo at single-cell transcriptome resolution. Science. 2017;8: eaan3235. doi:10.1126/science.aan3235.

Kettlun C, Galvan DL, George AL, Kaja A, Wilson MH. Manipulating piggyBac transposon chromosomal integration site selection in human cells. Molecular therapy : the journal of the American Society of Gene Therapy. 2011;19: 1636-1644. doi:10.1038/mt.2011.129.

Kind J, Pagie L, de Vries SS, Nahidiazar L, Dey SS, Bienko M, et al. Genome-wide Maps of Nuclear Lamina Interactions in Single Human Cells. Cell. Cell Press; 2015;163: 134-147. doi:10.1016/j.cell.2015.08.040.

Kind J, Pagie L, Ortabozkoyun H, Boyle S, de Vries SS, Janssen H, et al. Single-Cell Dynamics of Genome-Nuclear Lamina Interactions. Cell. Cell Press; 2013;153: 178-192. doi:10.1016/j.cell.2013.02.028.

Klein, A.M. et al. Droplet Barcoding for Single-Cell Transcriptomics Applied to Embryonic Stem Cells. *Cell* 161, 1187-1201, doi:10.1016/j.cell.2015.05.002 (2015).

(56) References Cited

OTHER PUBLICATIONS

Kvon EZ, Kamneva OK, Melo US, Barozzi I, Osterwalder M, Mannion BJ, et al. Progressive Loss of Function in a Limb Enhancer during Snake Evolution. Cell. 2016;167: 633-642.e11. doi:10.1016/j.cell.2016.09.028.

Lawrence M, Daujat S, Schneider R. Lateral Thinking: How Histone Modifications Regulate Gene Expression. Molecular Cell. 2016;32: 42-56. doi:10.1016/j.tig.2015.10.007 It is made available under a CC-BY-NC-ND 4.0 International license. was not peer-reviewed) is the author/funder, who has granted bioRxiv a license to display the preprint in perpetuity. bioRxiv preprint first posted online Feb. 1, 2019; doi: http://dx.doi.org/10.1101/538553.

Lee TI, Young RA. Transcriptional Regulation and Its Misregulation in Disease. Cell. Elsevier; 2013;152: 1237-1251. doi:10.1016/j.cell.2013.02.014.

Liu X, Huang J, Chen T, Wang Y, Xin S, Li J, et al. Yamanaka factors critically regulate the developmental signaling network in mouse embryonic stem cells. Cell Res. 2008;18: 1177-1189. doi:10.1038/cr.2008.309.

Loven J, Hoke HA, Lin CY, Lau A, Orlando DA, Vakoc CR, et al. Selective Inhibition of Tumor Oncogenes by Disruption of Super-Enhancers. Cell. Cell Press; 2013;153: 320-334. doi:10.1016/j.cell.2013.03.036.

Macaulay IC, Haerty W, Kumar P, Li YI, Hu TX, Teng MJ, et al. G&T-seq: parallel sequencing of single-cell genomes and transcriptomes. Nature Methods. Nature Research; 2015;12: 519-522. doi:10.1038/nmeth.3370.

Machanick P, Bailey TL. MEME-ChIP: motif analysis of large DNA datasets. Bioinformatics. Oxford University Press; 2011;27: 1696-1697. doi:10.1093/bioinformatics/btr189.

Macleod D, Charlton J, Mullins J, Bird AP. Sp1 sites in the mouse aprt gene promoter are required to prevent methylation of the CpG island. Genes Dev. 1994;8: 2282-2292.

Macosko EZ, Basu A, Satija R, Nemesh J, Shekhar K, Goldman M, et al. Highly Parallel Genome-wide Expression Profiling of Individual Cells Using Nanoliter Droplets. Cell. 2015;161: 1202-1214.

Macosko, E. Z. et al. Highly Parallel Genome-wide Expression Profiling of Individual Cells Using Nanoliter Droplets. *Cell* 161, 1202-1214, doi:10.1016/j.cell.2015.05.002 (2015).

Martin M. Cutadapt removes adapter sequences from high-throughput sequencing reads. EMBnetjournal. 2011;17: 10-12. doi:10.14806/ej.17.1.200.

Mates L, Chuah MKL, Belay E, Jerchow B, Manoj N, Acosta-Sanchez A, et al. Molecular evolution of a novel hyperactive *Sleeping Beauty* transposase enables robust stable gene transfer in vertebrates. Nat Genet. Nature Publishing Group; 2009;41: 753-761. doi:10.1038/ng.343.

Mayhew, D. & Mitra, R. D. Transcription factor regulation and chromosome dynamics during pseudohyphal growth. *Mol Biol Cell* 25, 2669-2676, doi:10.1091/mbc.E14-04-0871 (2014).

McCleland ML, Mesh K, Lorenzana E, Chopra VS, Segal E, Watanabe C, et al. CCAT1 is an enhancer templated RNA that predicts BET sensitivity in colorectal cancer. J Clin Invest. American Society for Clinical Investigation; 2016;126: 639-652. doi:10.1172/JCI83265.

Mi H, Huang X, Muruganujan A, Tang H, Mills C, Kang D, et al. PANTHER version 11: expanded annotation data from Gene Ontology and Reactome pathways, and data analysis tool enhancements. Nucl Acids Res. Oxford University Press; 2017;45: D183-D189. doi:10.1093/nar/gkw1138.

Mizuguchi R, Sugimori M, Takebayashi H, Kosako H, Nagao M, Yoshida S, et al. Combinatorial Roles of Olig2 and Neurogenin2 in the Coordinated Induction of Pan-Neuronal and Subtype-Specific Properties of Motoneurons. Neuron. Elsevier; 2001;31: 757-771. doi:10.1016/S0896-6273(01)00413-5.

Molyneaux BJ, Arlotta P, Menezes JRL, Macklis JD. Neuronal subtype specification in the cerebral cortex. Nature Reviews Neuroscience. Nature Publishing Group; 2007;8: 427-437. doi:10.1038/nrn2151.

Peterson VM, Zhang KX, Kumar N, Wong J, Li L, Wilson DC, et al. Multiplexed quantification of proteins and transcripts in single cells. Nat Biotechnol. 2017;9: 2579. doi:10.1038/nbt.3973.

Philipsen S, Suske G. A tale of three fingers: the family of mammalian Sp/XKLF transcription factors. Nucl Acids Res. Oxford University Press; 1999;27: 2991-3000. doi:10.1093/nar/27.15.2991.

Picelli S, Bjorklund AK, Reinius B, Sagasser S, Winberg G, Sandberg R. Tn5 transposase and tagmentation procedures for massively scaled sequencing projects. Genome Res. Cold Spring Harbor Lab; 2014;24: 2033-2040. doi:10.1101/gr.177881.114.

Pott S, Lieb JD. What are super-enhancers? Nat Genet. 2014;47: 8-12. doi:10.1038/ng.3167.

Pucilowska J, Puzerey PA, Karlo JC, Galan RF, Landreth GE. Disrupted ERK Signaling during Cortical Development Leads to Abnormal Progenitor Proliferation, Neuronal and Network Excitability and Behavior, Modeling Human Neuro-Cardio-Facial-Cutaneous and Related Syndromes. Journal of Neuroscience. Society for Neuroscience; 2012;32: 8663-8677. doi:10.1523/JNEUROSCI.1107-12.2012.

Qi Z, Wilkinson MN, Chen X, Sankararaman S, Mayhew D, Mitra RD. An optimized, broadly applicable piggyBac transposon induction system. Nucl Acids Res. Oxford University Press; 2017;: gkw1290. doi:10.1093/nar/gkw1290.

Quinlan AR, Hall IM. BEDTools: a flexible suite of utilities for comparing genomic features. Bioinformatics. Oxford University Press; 2010;26: 841-842. doi:10.1093/bioinformatics/btq033.

Raff T, van der Giet M, Endemann D, Wiederholt T, Paul M. Design and Testing of β-Actin Primers for RT-PCR that Do Not Co-amplify Processed Pseudogenes. BioTechniques. Future Science Ltd London, UK; 1997;23: 456-460. doi:10.2144/97233st02.

Ramirez F, Ryan DP, Gruning B, Bhardwaj V, Kilpert F, Richter AS, et al. deepTools2: a next generation web server for deep-sequencing data analysis. Nucl Acids Res. Oxford University Press; 2016;44: W160-W165. doi:10.1093/nar/gkw257.

Rašin M-R, Gazula V-R, Breunig JJ, Kwan KY, Johnson MB, Liu-Chen S, et al. Numb and Numbl are required for maintenance of cadherin-based adhesion and polarity of neural progenitors. Nature Neuroscience. Nature Publishing Group; 2007;10: 819-827. doi:10.1038/nn1924.

Rodriguez-Fraticelli AE, Wolock SL, Weinreb CS, Panero R, Patel SH, Jankovic M, et al. Clonal analysis of lineage fate in native haematopoiesis. Nature. Nature Publishing Group; 2018;124: 1929. doi:10.1038/nature25168 It is made available under a CC-BY-NC-ND 4.0 International license. was not peer-reviewed) is the author/funder, who has granted bioRxiv a license to display the preprint in perpetuity. bioRxiv preprint first posted online Feb. 1, 2019; doi: http://dx.doi.org/10.1101/538553. The copyright holder for this preprint (which.

Rosenberg AB, Roco CM, Muscat RA, Kuchina A, Sample P, Yao Z, et al. Single-cell profiling of the developing mouse brain and spinal cord with split-pool barcoding. Science. American Association for the Advancement of Science; 2018;360: 176-182. doi:10.1126/science.aam8999.

Rotem A, Ram O, Shoresh N, Sperling RA, Goren A, Weitz DA, et al. Single-cell ChIP-seq reveals cell subpopulations defined by chromatin state. Nat Biotechnol. Nature Publishing Group; 2015;33: 1165-1172. doi:10.1038/nbt.3383.

Saridey SK, Liu L, Doherty JE, Kaja A, Galvan DL, Fletcher BS, et al. PiggyBac transposon-based inducible gene expression in vivo after somatic cell gene transfer. Molecular therapy : the journal of the American Society of Gene Therapy. 2009;17: 2115-2120. doi:10.1038/mt.2009.234.

Saunders A, Macosko EZ, Wysoker A, Goldman M, Krienen FM, de Rivera H, et al. Molecular Diversity and Specializations among the Cells of the Adult Mouse Brain. Cell. Cell Press; 2018;174: 1015-1030.e16. doi:10.1016/j.cell.2018.07.028.

Saxena A, Wagatsuma A, Noro Y, Kuji T, Asaka-Oba A, Watahiki A, et al. Trehalose-enhanced isolation of neuronal sub-types from adult mouse brain. BioTechniques. Future Science Ltd London, UK; 2012;52: 381-385. doi:10.2144/0000113878.

Scargle JD, Norris JP, Jackson B, Chiang J. Studies in Astronomical Time Series Analysis. VI. Bayesian Block Representations. ApJ. IOP Publishing; 2013;764: 167. doi:10.1088/0004-637X/764/2/167.

(56) References Cited

OTHER PUBLICATIONS

Scheiber IF, Dringen R. Astrocyte functions in the copper homeostasis of the brain. Neurochemistry International. Pergamon; 2013;62: 556-565. doi:10.1016/j.neuint.2012.08.017.

Schuster DJ, Dykstra JA, Riedl MS, Kitto KF, Belur LR, McIvor RS, et al. Biodistribution of adenoassociated virus serotype 9 (AAV9) vector after intrathecal and intravenous delivery in mouse. Front Neuroanat. Frontiers; 2014;8: 42. doi:10.3389/fnana.2014.00042.

Shapiro E, Biezuner T, Linnarsson S. Single-cell sequencing-based technologies will revolutionize whole-organism science. Nature Reviews Genetics. Nature Research; 2013;14: 618-630. doi:10.1038/nrg3542 It is made available under a CC-BY-NC-ND 4.0 International license. was not peer-reviewed) is the author/funder, who has granted bioRxiv a license to display the preprint in perpetuity. bioRxiv preprint first posted online Feb. 1, 2019; doi: http://dx.doi.org/10.1101/538553.

Shema E, Bernstein BE, Buenrostro JD. Single-cell and single-molecule epigenomics to uncover genome regulation at unprecedented resolution. Nat Genet. Nature Publishing Group; 2018;51: 19-25. doi:10.1038/s41588-018-0290-x.

Sloan CA, Chan ET, Davidson JM, Malladi VS, Strattan JS, Hitz BC, et al. ENCODE data at the ENCODE portal. Nucl Acids Res. Oxford University Press; 2016;44: D726-D732. doi:10.1093/nar/gkv1160.

Stoeckius M, Hafemeister C, Stephenson W, Houck-Loomis B, Chattopadhyay PK, Swerdlow H, et al. Simultaneous epitope and transcriptome measurement in single cells. Nature Methods. Nature Publishing Group; 2017;14: 865-868. doi:10.1038/nmeth.4380.

Stoeckius M, Zheng S, Houck-Loomis B, Hao S, Yeung BZ, Mauck WM, et al. Cell Hashing with barcoded antibodies enables multiplexing and doublet detection for single cell genomics. Genome Biol. BioMed Central; 2018;19: 224. doi:10.1186/s13059-018-1603-1.

Stroud H, Su SC, Hrvatin S, Greben AW, Renthal W, Boxer LD, et al. Early-Life Gene Expression in Neurons Modulates Lasting Epigenetic States. Cell. 2017;171: 1151-1164.e16. doi:10.1016/j.cell.2017.09.047 66. Zhang Y, Chen K, Sloan SA, Bennett ML, Scholze AR, O'Keeffe S, et al. An RNA-Sequencing Transcriptome and Splicing Database of Glia, Neurons, and Vascular Cells of the Cerebral Cortex. Journal of Neuroscience. Society for Neuroscience; 2014;34: 11929-11947. doi:10.1523/JNEUROSCI.1860-14.2014.

Sun J, Ramos A, Chapman B, Johnnidis JB, Le L, Ho Y-J, et al. Clonal dynamics of native haematopoiesis. Nature. Nature Research; 2014;514: 322-327. doi:10.1038/nature13824.

Svensson V, Vento-Tormo R, Teichmann SA. Exponential scaling of single-cell RNA-seq in the past decade. Nature Protocols. Nature Publishing Group; 2018;13: 599-604. doi:10.1038/nprot.2017.149.

Takahashi K, Yamanaka S. Induction of Pluripotent Stem Cells from Mouse Embryonic and Adult Fibroblast Cultures by Defined Factors. Cell. 2006;126: 663-676. doi:10.1016/j.cell.2006.07.024.

Tasic B, Yao Z, Graybuck LT, Smith KA, Nguyen TN, Bertagnolli D, et al. Shared and distinct transcriptomic cell types across neocortical areas. Nature. 5 ed. Nature Publishing Group; 2018;563: 72-78. doi:10.1038/s41586-018-0654-5.

The ENCODE Project Consortium. An integrated encyclopedia of DNA elements in the human genome. Nature. Nature Publishing Group; 2012;489: 57-74. doi:10.1038/nature11247.

Transcriptional Pause Sites Delineate Stable Nucleosome-Associated Premature Polyadenylation Suppressed by U1 snRNP. Molecular Cell. 2018;69: 648-663.e7. doi:10.1016/j.molcel.2018.01.006.

VanderPlas J, Connolly AJ, Ivezic Z, Gray A. Introduction to astroML: Machine learning for astrophysics. IEEE; pp. 47-54. doi:10.1109/CIDU.2012.6382200.

Vink et al. (2009) Sleeping Beauty Transposition From Nonintegrating Lentivirus. Molecular Therapy vol. 17(7), pp. 1197-1204.

Vogel MJ, Peric-Hupkes D, van Steensel B. Detection of in vivo protein-DNA interactions using DamID in mammalian cells. Nature Protocols. 2007;2: 1467-1478. doi:10.1038/nprot.2007.148.

Wang H, Johnston M, Mitra RD. Calling cards for DNA-binding proteins. Genome Res. Cold Spring Harbor Lab; 2007;17: 1202-1209. doi:10.1101/gr.6510207 33. Wang H, Mayhew D, Chen X, Johnston M, Mitra RD. Calling Cards enable multiplexed identification of the genomic targets of DNA-binding proteins. Genome Res. Cold Spring Harbor Lab; 2011;21: 748-755. doi:10.1101/gr.114850.110.

Wang H, Mayhew D, Chen X, Johnston M, Mitra RD. "Calling Cards" for DNA-Binding Proteins in Mammalian Cells. Genetics. Genetics; 2012;190: 941-949. doi:10.1534/genetics.111.137315.

Wang W, Lin C, Lu D, Ning Z, Cox T, Melvin D, et al. Chromosomal transposition of PiggyBac in mouse embryonic stem cells. Proc Natl Acad Sci USA. National Academy of Sciences; 2008;105: 9290-9295. doi:10.1073/pnas.0801017105.

Wang, H., Heinz, M. E., Crosby, S. D., Johnston, M. & Mitra, R. D. 'Calling Cards' method for high-throughput identification of targets of yeast DNA-binding proteins. *Nat Protoc* 3, 1569-1577 (2008).

Wang, H., Mayhew, D., Chen, X., Johnston, M. & Mitra, R. D. Calling Cards enable multiplexed identification of the genomic targets of DNA-binding proteins. *Genome Res* 21, 748-755, doi:10.1101/gr.114850.110 (2011).

Whyte WA, Orlando DA, Hnisz D, Abraham BJ, Lin CY, Kagey MH, et al. Master Transcription Factors and Mediator Establish Super-Enhancers at Key Cell Identity Genes. Cell. 2013;153: 307-319. doi:10.1016/j.cell.2013.03.035.

Wilson MH, Coates CJ, George AL. PiggyBac transposon-mediated gene transfer in human cells. Molecular therapy : the journal of the American Society of Gene Therapy. 2007;15: 139-145. doi:10.1038/sj.mt.6300028.

Wolf FA, Angerer P, Theis Fj. SCANPY : large-scale single-cell gene expression data analysis. Genome Biol. BioMed Central; 2018;19: 15. doi:10.1186/s13059-017-1382-0.

Wu SC-Y, Meir Y-JJ, Coates CJ, Handler AM, Pelczar P, Moisyadi S, et al. piggyBac is a flexible and highly active transposon as compared to sleeping beauty, Tol2, and Mos1 in mammalian cells. PNAS. National Acad Sciences; 2006;103: 15008-15013. doi:10.1073/pnas.0606979103.

Xi H, Yu Y, Fu Y, Foley J, Halees A, Weng Z. Analysis of overrepresented motifs in human core promoters reveals dual regulatory roles of YY1. Genome Res. Cold Spring Harbor Lab; 2007;17: 798-806. doi:10.1101/gr.5754707.

Yen L, Svendsen J, Lee J-S, Gray JT, Magnier M, Baba T, et al. Exogenous control of mammalian gene expression through modulation of RNA self-cleavage. Nature. Nature Publishing Group; 2004;431: 471-476. doi:10.1038/nature02844.

Yoshida J, Akagi K, Misawa R, Kokubu C, Takeda J, Horie K. Chromatin states shape insertion profiles of the piggyBac, Tol2 and Sleeping Beauty transposons and murine leukemia virus. Scientific Reports. Nature Publishing Group; 2017;7: 43613. doi:10.1038/srep43613.

Yusa K, Zhou L, Li MA, Bradley A, Craig NL. A hyperactive piggyBac transposase for mammalian applications. Proc Natl Acad Sci USA. National Acad Sciences; 2011;108: 1531-1536. doi:10.1073/pnas.1008322108.

Zeisel A, Hochgerner H, Lonnerberg P, Johnsson A, Memic F, van der Zwan J, et al. Molecular Architecture of the Mouse Nervous System. Cell. Elsevier; 2018; 174: 999-1014.e22. doi:10.1016/j.cell.2018.06.021.

Zeisel A, Munoz-Manchado AB, Codeluppi S, Lonnerberg P, La Manno G, Jureus A, et al. Cell types in the mouse cortex and hippocampus revealed by single-cell RNA-seq. Science. American Association for the Advancement of Science; 2015;347: 1138-1142. doi:10.1126/science.aaa1934.

Zhang Y, Liu T, Meyer CA, Eeckhoute J, Johnson DS, Bernstein BE, et al. Model-based Analysis of ChIP-Seq (MACS). Genome Biol. BioMed Central; 2008;9: R137. doi:10.1186/gb-2008-9-9-r137.

Zheng D, Liu X, Tian B. 3'READS+, a sensitive and accurate method for 3" end sequencing of polyadenylated RNA. RNA. Cold Spring Harbor Lab; 2016;22: 1631-1639. doi:10.1261/rna.057075.116.

(56) References Cited

OTHER PUBLICATIONS

Zheng GXY, Terry JM, Belgrader P, Ryvkin P, Bent ZW, Wilson R, et al. Massively parallel digital transcriptional profiling of single cells. Nat Commun. Nature Publishing Group; 2017;8: 14049. doi:10.1038/ncomms14049.

Zhu X, Zuo H, Maher BJ, Serwanski DR, LoTurco JJ, Lu QR, et al. Olig2-dependent developmental fate switch of NG2 cells. Development. Oxford University Press for The Company of Biologists Limited; 2012;139: 2299-2307. doi:10.1242/dev.078873.

\* cited by examiner

A. Reverse Transcription

B. Template Switching

C. Initial PCR

D. Specific PCR

E. Circularization

F. Shear and Pull Down

G. End Repair and A-Tailing

H. Y-adapter Ligation

I. PCR Amplification and Illumina Sequencing with Custom Primers

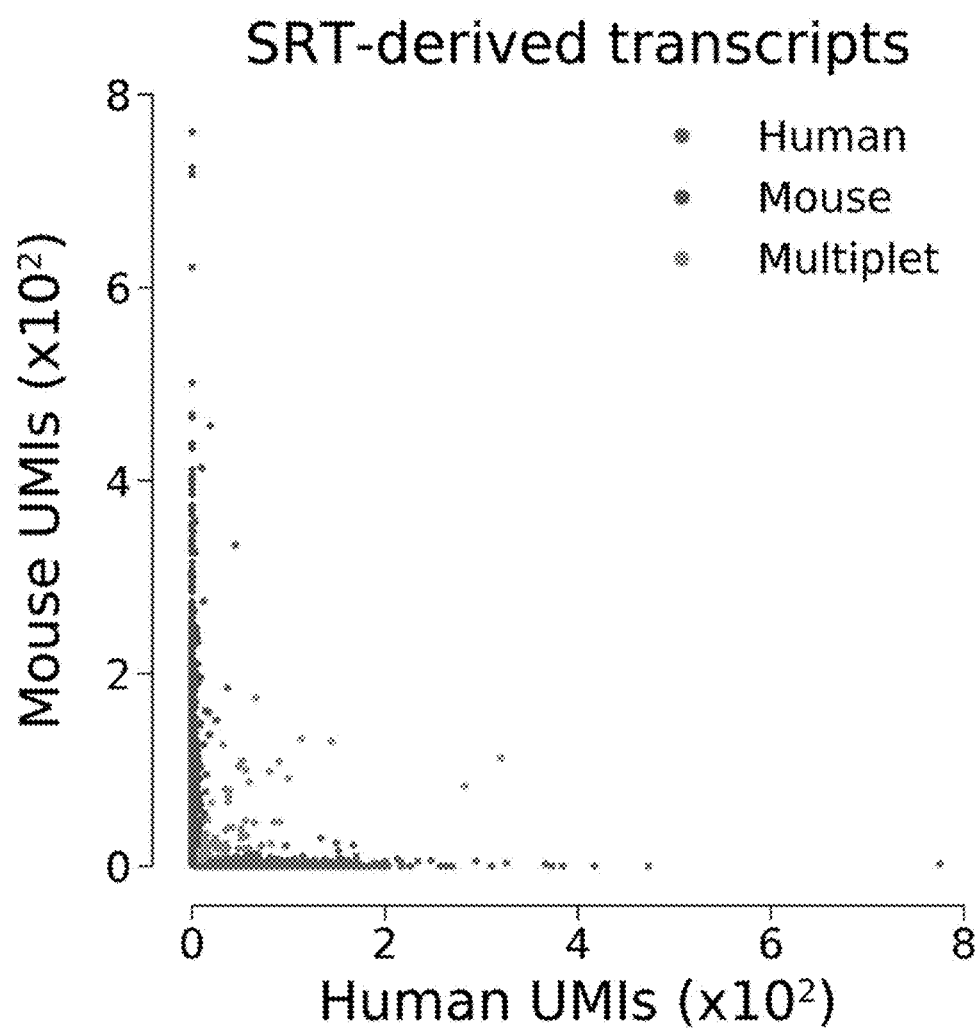

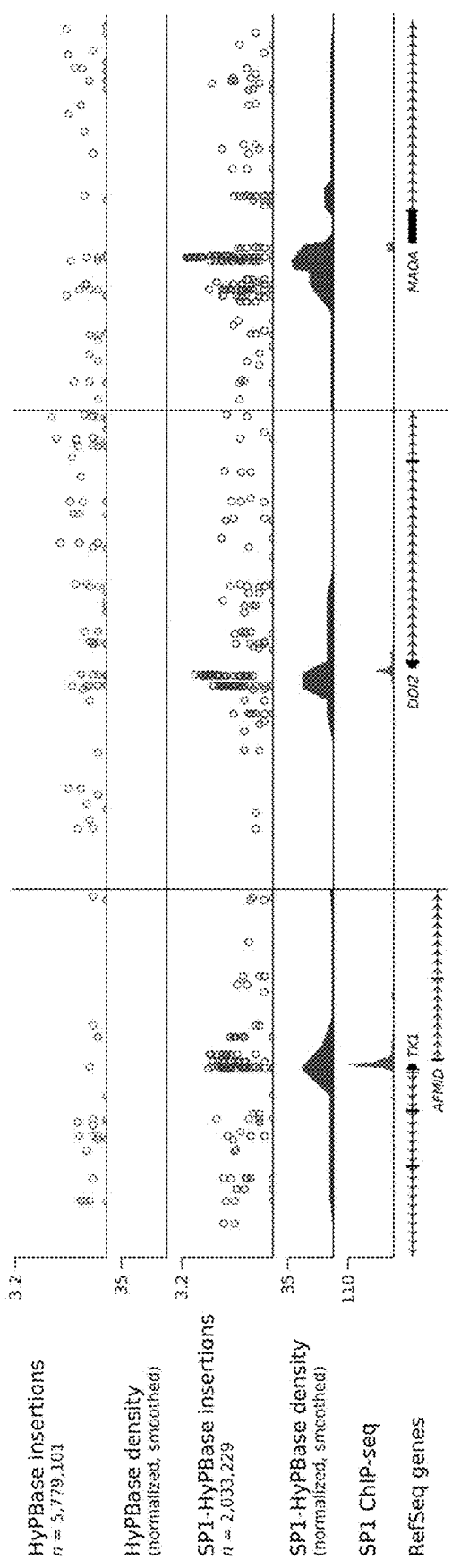

FIG. 12F
HT-SELEX derived motif (Jolma et al. 2013)
SP1-HyPBase derived motif
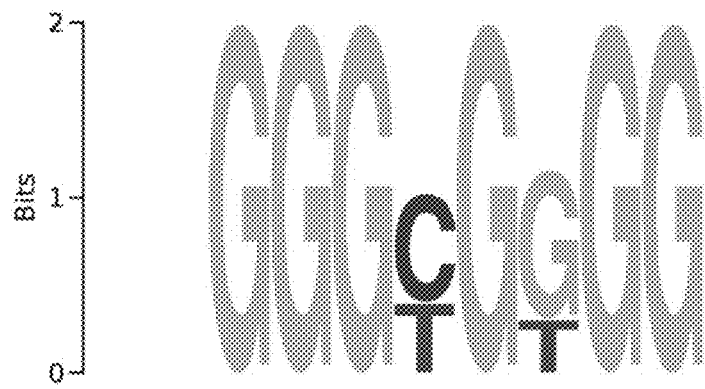

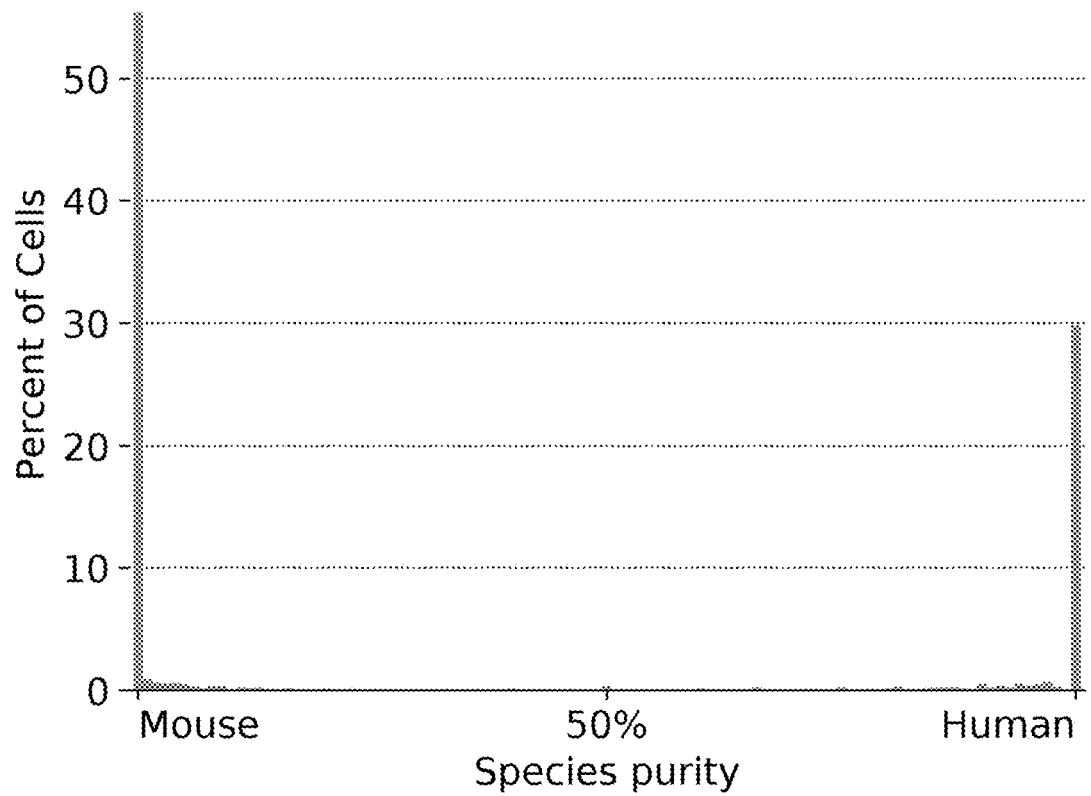

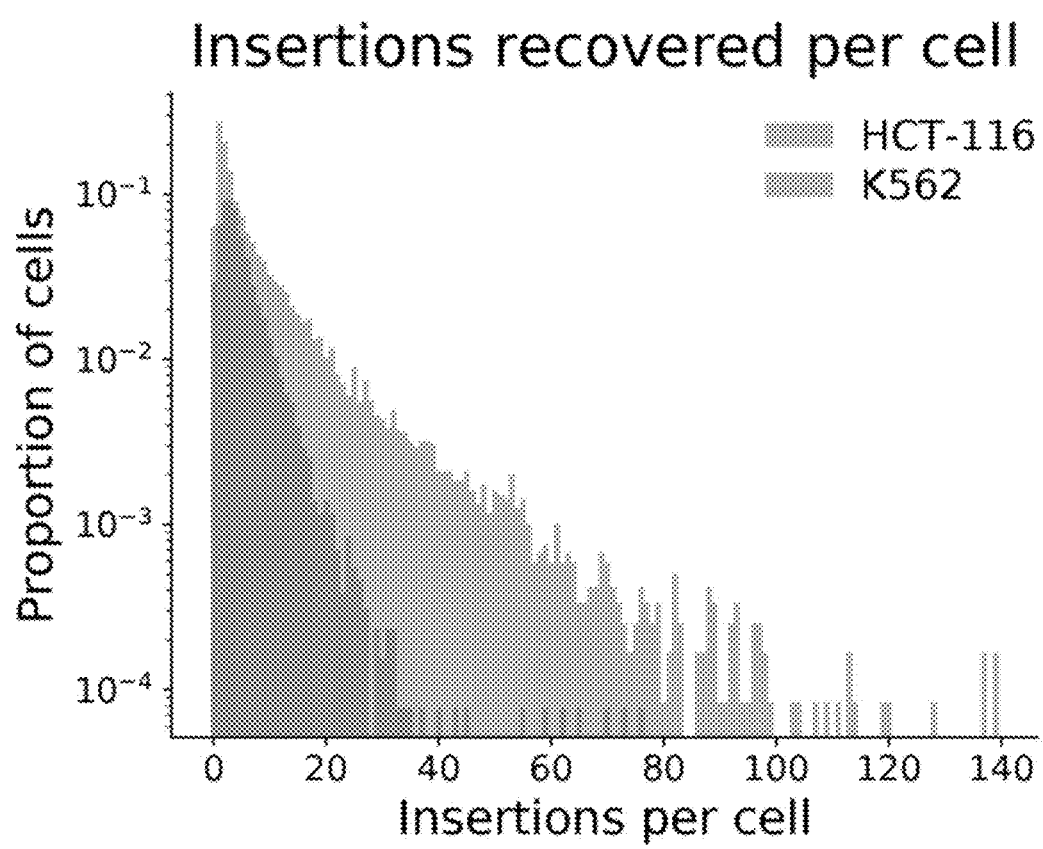

| | Mapped reads | Unique insertions |
|---|---|---|
| WT_L1 | 1,097,928 | 25,870 |
| SP1_L1 | 1,219,701 | 28,460 |

| | WT_L1 insertion (%) | Random insertion(%) | SP1_L1 insertion (%) |
|---|---|---|---|
| 3UTR | 0.87 | 0.69 | 0.67 |
| miRNA | 0.00 | 0.00 | 0.00 |
| ncRNA | 0.17 | 0.18 | 0.15 |
| TTS | 0.88 | 0.93 | 0.83 |
| pseudo | 0.02 | 0.06 | 0.05 |
| Exon | 1.02 | 1.07 | 0.91 |
| Intron | 44.25 | 37.18 | 39.93 |
| Intergenic | 51.67 | 58.76 | 54.88 |
| Promoter | 0.92 | 0.99 | 2.42 * |
| 5UTR | 0.05 | 0.05 | 0.15 * |
| CpG-Island | 0.12 | 0.21 | 0.44 * |

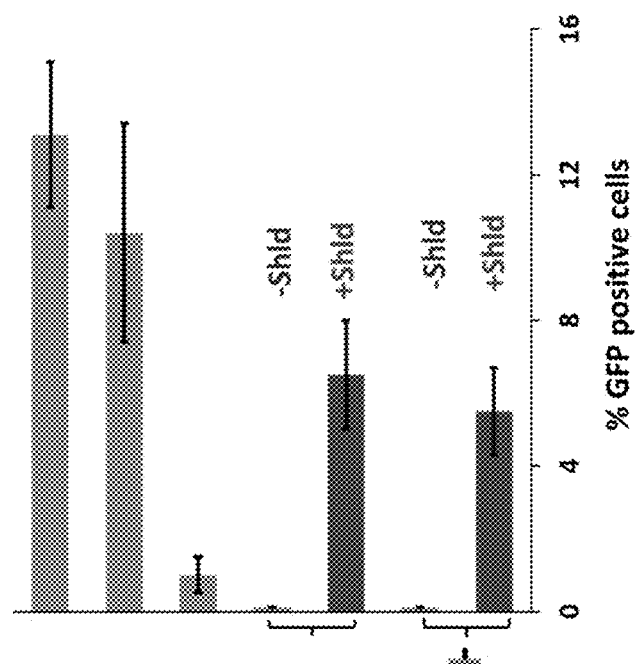
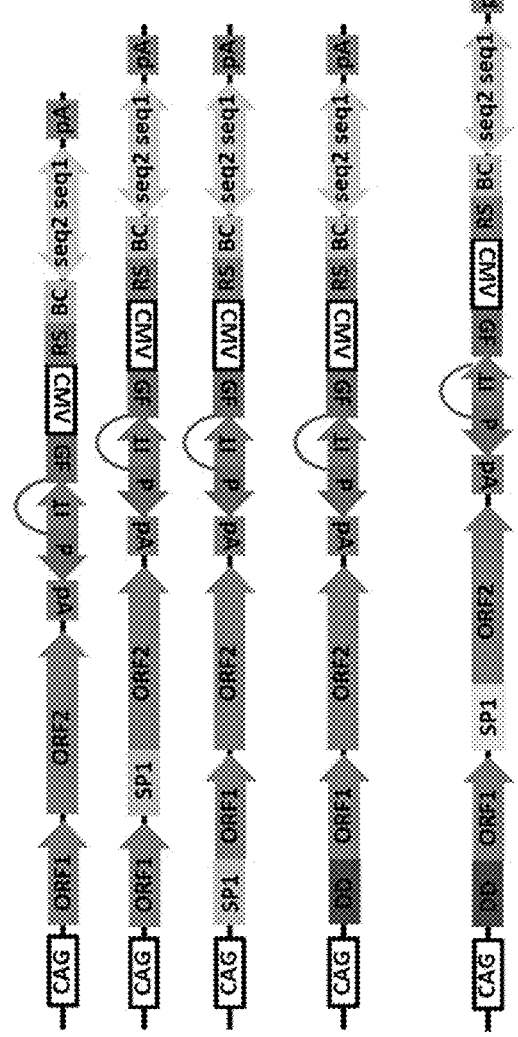
FIG. 23

SEQUENCE LISTING

```
<160> NUMBER OF SEQ ID NOS: 50

<210> SEQ ID NO 1
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 1
cacttagctt tg                                                              12

<210> SEQ ID NO 2
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 2
cgccgtagtc cc                                                              12

<210> SEQ ID NO 3
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 3
aatgaaaaac ct                                                              12

<210> SEQ ID NO 4
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 4
atggactttg tt                                                              12

<210> SEQ ID NO 5
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 5
ttgggtagca tc                                                              12

<210> SEQ ID NO 6
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 6
aggaatctga ac                                                              12

<210> SEQ ID NO 7
<211> LENGTH: 12
<212> TYPE: DNA
<213> ORGANISM: Artificial Sequence
```

```
<220> FEATURE:
<223> OTHER INFORMATION: Synthetic DNA Barcode

<400> SEQUENCE: 7
cctgtgaatg tg                                                              12

<210> SEQ ID NO 8
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 8
ggggtcgcgc gc                                                              12

<210> SEQ ID NO 9
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 9
atagaccttt at                                                              12

<210> SEQ ID NO 10
<211> LENGTH: 12
<212> TYPE: DNA
<213> ORGANISM: Artificial Sequence
<220> FEATURE:
<223> OTHER INFORMATION: Synthetic DNA Barcode

<400> SEQUENCE: 10
ctccggttca ag                                                              12

<210> SEQ ID NO 11
<211> LENGTH: 36
<212> TYPE: DNA
<213> ORGANISM: Artificial Sequence
<220> FEATURE:
<223> OTHER INFORMATION: Synthetic DNA Barcode
<220> FEATURE:
<221> NAME/KEY: misc_feature
<222> LOCATION: (21)..(27)
<223> OTHER INFORMATION: n is a, c, g, or t

<400> SEQUENCE: 11
atgcgttgat aacgatgtcc nnnnnnnggt actcaa                                    36

<210> SEQ ID NO 12
<211> LENGTH: 6
<212> TYPE: RNA
<213> ORGANISM: Artificial Sequence
<220> FEATURE:
<223> OTHER INFORMATION: Synthetic cryptic poly a sequence

<400> SEQUENCE: 12 aauaaa                                                                      6

<210> SEQ ID NO 13
<211> LENGTH: 59
<212> TYPE: DNA
<213> ORGANISM: Artificial Sequence
<220> FEATURE:
<223> OTHER INFORMATION: Synthetic DNA primer
<220> FEATURE:
```

```
<221> NAME/KEY: misc_feature
<222> LOCATION: (59)..(59)
<223> OTHER INFORMATION: n is a, c, g, or t

<400> SEQUENCE: 13
aagcagtggt atcaacgcag agtacgtttt tttttttttt tttttttttt tttttttvn      59

<210> SEQ ID NO 14
<211> LENGTH: 23
<212> TYPE: DNA
<213> ORGANISM: Artificial Sequence
<220> FEATURE:
<223> OTHER INFORMATION: Synthetic DNA primer

<400> SEQUENCE: 14
aagcagtggt atcaacgcag agt                                             23

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 15
caacctcccc ttctacgagc                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 16
tcctgtacgg catggacgag                                                 20

<210> SEQ ID NO 17
<211> LENGTH: 19
<212> TYPE: DNA
<213> ORGANISM: Artificial Sequence
<220> FEATURE:
<223> OTHER INFORMATION: Synthetic DNA primer

<400> SEQUENCE: 17
cctcgccttt gccgatccg                                                  19

<210> SEQ ID NO 18
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 18
ggatcttcat gaggtagtca gtcaggtcc                                       29

<210> SEQ ID NO 19
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 19
aatgatacgg cgaccaccga gatctacact ctttccctac acgacgctct tccgatctac     60
```
gtttacgcag actatctttc tag                                            83

<210> SEQ ID NO 20
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 20
aatgatacgg cgaccaccga gatctacact ctttccctac acgacgctct tccgatctct    60
atttacgcag actatctttc tag                                            83

<210> SEQ ID NO 21
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 21
aatgatacgg cgaccaccga gatctacact ctttccctac acgacgctct tccgatctga    60
ttttacgcag actatctttc tag                                            83

<210> SEQ ID NO 22
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 22
aatgatacgg cgaccaccga gatctacact ctttccctac acgacgctct tccgatcttg    60
ctttacgcag actatctttc tag                                            83

<210> SEQ ID NO 23
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 23
aatgatacgg cgaccaccga gatctacact ctttccctac acgacgctct tccgatctta    60
gtttacgcag actatctttc tag                                            83

<210> SEQ ID NO 24
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 24
aatgatacgg cgaccaccga gatctacact ctttccctac acgacgctct tccgatctat    60
ctttacgcag actatctttc tag                                            83

<210> SEQ ID NO 25
<211> LENGTH: 83
<212> TYPE: DNA
<213> ORGANISM: Artificial Sequence
<220> FEATURE:

<223> OTHER INFORMATION: Synthetic DNA primer

<400> SEQUENCE: 25
aatgatacgg cgaccaccga gatctacact ctttccctac acgacgctct tccgatctcg    60
ttttacgcag actatctttc tag    83

<210> SEQ ID NO 26
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 26
aatgatacgg cgaccaccga gatctacact ctttccctac acgacgctct tccgatctgc    60
atttacgcag actatctttc tag    83

<210> SEQ ID NO 27
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 27
aatgatacgg cgaccaccga acactctttc cctacacgac gctcttccga tctacgtaag    60
tgtatgtaaa cttccgactt caa    83

<210> SEQ ID NO 28
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 28
aatgatacgg cgaccaccga acactctttc cctacacgac gctcttccga tctctataag    60
tgtatgtaaa cttccgactt caa    83

<210> SEQ ID NO 29
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 29
aatgatacgg cgaccaccga acactctttc cctacacgac gctcttccga tctgattaag    60
tgtatgtaaa cttccgactt caa    83

<210> SEQ ID NO 30
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 30
aatgatacgg cgaccaccga acactctttc cctacacgac gctcttccga tcttgctaag    60
tgtatgtaaa cttccgactt caa    83

```
<210> SEQ ID NO 31
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 31
aatgatacgg cgaccaccga acactctttc cctacacgac gctcttccga tcttagtaag      60
tgtatgtaaa cttccgactt caa                                              83

<210> SEQ ID NO 32
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 32
aatgatacgg cgaccaccga acactctttc cctacacgac gctcttccga tctatctaag      60
tgtatgtaaa cttccgactt caa                                              83

<210> SEQ ID NO 33
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 33
aatgatacgg cgaccaccga acactctttc cctacacgac gctcttccga tctcgttaag      60
tgtatgtaaa cttccgactt caa                                              83

<210> SEQ ID NO 34
<211> LENGTH: 83
<212> TYPE: DNA
<213> ORGANISM: Artificial Sequence
<220> FEATURE:
<223> OTHER INFORMATION: Synthetic DNA primer

<400> SEQUENCE: 34
aatgatacgg cgaccaccga acactctttc cctacacgac gctcttccga tctgcataag      60
tgtatgtaaa cttccgactt caa                                              83

<210> SEQ ID NO 35
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 35
caagcagaag acggcatacg agat                                             24

<210> SEQ ID NO 36
<211> LENGTH: 15
<212> TYPE: DNA
<213> ORGANISM: Artificial Sequence
<220> FEATURE:
<223> OTHER INFORMATION: Synthetic DNA primer

<400> SEQUENCE: 36
gtctcgtggg ctcgg                                                       15
```

```
<210> SEQ ID NO 37
<211> LENGTH: 33
<212> TYPE: DNA
<213> ORGANISM: Artificial Sequence
<220> FEATURE:
<223> OTHER INFORMATION: Synthetic DNA primer

<400> SEQUENCE: 37
aagcagtggt atcaacgcag agtacatrgr grg                                33

<210> SEQ ID NO 38
<211> LENGTH: 33
<212> TYPE: DNA
<213> ORGANISM: Artificial Sequence
<220> FEATURE:
<223> OTHER INFORMATION: Synthetic DNA primer
<220> FEATURE:
<221> NAME/KEY: misc_feature
<222> LOCATION: (13)..(13)
<223> OTHER INFORMATION: biotinylated base
<220> FEATURE:
<221> NAME/KEY: misc_feature
<222> LOCATION: (30)..(33)
<223> OTHER INFORMATION: phosphorothioate bonds between bases

<400> SEQUENCE: 38
acactctttc cctacacgac gctcttccga tct                                33

<210> SEQ ID NO 39
<211> LENGTH: 29
<212> TYPE: DNA
<213> ORGANISM: Artificial Sequence
<220> FEATURE:
<223> OTHER INFORMATION: Synthetic DNA primer
<220> FEATURE:
<221> NAME/KEY: misc_feature
<222> LOCATION: (16)..(19)
<223> OTHER INFORMATION: phosphorothioate bond between bases
<220> FEATURE:
<221> NAME/KEY: misc_feature
<222> LOCATION: (20)..(20)
<223> OTHER INFORMATION: biotinylated thymine base

<400> SEQUENCE: 39
gcgtcaattt tacgcagaca tctttctag                                     29

<210> SEQ ID NO 40
<211> LENGTH: 58
<212> TYPE: DNA
<213> ORGANISM: Artificial Sequence
<220> FEATURE:
<223> OTHER INFORMATION: Synthetic DNA primer
<220> FEATURE:
<221> NAME/KEY: misc_feature
<222> LOCATION: (57)..(58)
<223> OTHER INFORMATION: phosphorothioate bond between bases

<400> SEQUENCE: 40
aatgatacgg cgaccaccga gatcttcact cattccacac gactccttgc cagtctct     58

<210> SEQ ID NO 41
<211> LENGTH: 33
<212> TYPE: DNA
<213> ORGANISM: Artificial Sequence
<220> FEATURE:
<223> OTHER INFORMATION: Synthetic DNA primer

<400> SEQUENCE: 41
gagactggca agtacacgtc gcactcacca tga                                33
```

<210> SEQ ID NO 42
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 42
atctcgtatg ccgtcttctg cttg                                    24

<210> SEQ ID NO 43
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 43
aatgatacgg cgaccaccga gatc                                    24

<210> SEQ ID NO 44
<211> LENGTH: 24
<212> TYPE: DNA
<213> ORGANISM: Artificial Sequence
<220> FEATURE:
<223> OTHER INFORMATION: Synthetic DNA primer

<400> SEQUENCE: 44
caagcagaag acggcatacg agat                                    24

<210> SEQ ID NO 45
<211> LENGTH: 48
<212> TYPE: DNA
<213> ORGANISM: Artificial Sequence
<220> FEATURE:
<223> OTHER INFORMATION: Synthetic DNA primer

<400> SEQUENCE: 45
cgtgtaggga aagagtgtgc gtcaatttta cgcagactat ctttctag          48

<210> SEQ ID NO 46
<211> LENGTH: 33
<212> TYPE: DNA
<213> ORGANISM: Artificial Sequence
<220> FEATURE:
<223> OTHER INFORMATION: Synthetic DNA primer

<400> SEQUENCE: 46
gagactggca agtacacgtc gcactcacca tga                          33

<210> SEQ ID NO 47
<211> LENGTH: 31
<212> TYPE: DNA
<213> ORGANISM: Artificial Sequence
<220> FEATURE:
<223> OTHER INFORMATION: Synthetic DNA barcode
<220> FEATURE:
<221> NAME/KEY: misc_feature
<222> LOCATION: (1)..(3)
<223> OTHER INFORMATION: n is a, c, g, or t

<400> SEQUENCE: 47
nnntttacgc agactatctt tctagggtta a                            31

<210> SEQ ID NO 48

```
<211> LENGTH: 35
<212> TYPE: DNA
<213> ORGANISM: Artificial Sequence
<220> FEATURE:
<223> OTHER INFORMATION: Synthetic DNA barcode
<220> FEATURE:
<221> NAME/KEY: misc_feature
<222> LOCATION: (1)..(3)
<223> OTHER INFORMATION: n is a, c, g, or t

<400> SEQUENCE: 48
nnntaagtgt atgtaaactt ccgacttcaa ctgta                               35

<210> SEQ ID NO 49
<211> LENGTH: 68
<212> TYPE: DNA
<213> ORGANISM: Artificial Sequence
<220> FEATURE:
<223> OTHER INFORMATION: Synthetic DNA barcode
<220> FEATURE:
<221> NAME/KEY: misc_feature
<222> LOCATION: (36)..(45)
<223> OTHER INFORMATION: n is a, c, g, or t

<400> SEQUENCE: 49
ctgtctctta tacacatctc cgagcccacg agactnnnnn nnnnntctcg tatgccgtct    60
tctgcttg                                                             68

<210> SEQ ID NO 50
<211> LENGTH: 67
<212> TYPE: DNA
<213> ORGANISM: Artificial Sequence
<220> FEATURE:
<223> OTHER INFORMATION: Synthetic DNA barcode
<220> FEATURE:
<221> NAME/KEY: misc_feature
<222> LOCATION: (35)..(43)
<223> OTHER INFORMATION: n is a, c, g, or t

<400> SEQUENCE: 50
agagactggc aagtacacgt cgcactcacc atgannnnnn nnnatctcgt atgccgtctt    60
ctgcttg                                                              67
```

COMPOSITIONS OF SELF-REPORTING TRANSPOSON (SRT) CONSTRUCTS AND METHODS FOR MAPPING TRANSPOSON INSERTIONS

CROSS-REFERENCE TO RELATED APPLICATIONS

This application claims priority from U.S. Provisional Application Ser. No. 62/777,995 filed on 11 Dec. 2018, which is incorporated herein by reference in its entirety.

STATEMENT REGARDING FEDERALLY SPONSORED RESEARCH OR DEVELOPMENT

This invention was made with government support under NS076993, MH109133, HG009750, HG009986, and MH017070 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to self-reporting transposon (SRT) constructs and mapping of transposon insertions.

SUMMARY OF THE INVENTION

Among the various aspects of the present disclosure is the provision of compositions and methods for mapping transposon insertions.

An aspect of the present disclosure provides for a self-reporting transposon (SRT) construct comprised of a transposon comprising at least one promoter element wherein the promoter is capable of driving transcription of RNA through at least one transposon end after the SRT construct is inserted into genomic DNA, so that a portion of the transposon DNA, at least one transposon end, and the genomic DNA flanking the transposon end is transcribed into RNA.

Another aspect of the present disclosure provides for a method for the insertion of an SRT construct into a cellular genome wherein the SRT construct and either a (i) transposase capable of cutting or copying the transposon out of the transposon construct and pasting into genomic DNA, or (ii) a genome-associated protein (e.g. a transcription factor, a chromatin reader, writer, or eraser), hereafter referred to as GAP, operably linked to a transposase capable of cutting the transposon out of the transposon construct and pasting into genomic DNA are delivered to cells so that the transposase gene or genome-associated protein-transposase fusion is expressed, or can be induced, after delivery to the cells. The SRT construct and transposase gene can be delivered simultaneously or sequentially.

Yet another aspect of the present disclosure provides for a plasmid encoding an SRT construct as described herein.

In some embodiments, the promoter is capable of transcribing the 3' region flanking a transposon end comprising a transposon terminal repeat, resulting in an RNA transcript, wherein the RNA transcript is terminated by a cryptic poly-adenylation (poly-A) signal or picks up a poly-A stretch in the genome such that the transcript can be recovered by reverse transcription using a poly-T primer.

In some embodiments, the promoter is an inducible promoter.

In some embodiments, the inducible promoter is capable of being induced by a chemical inducer, light, or excision of a stop codon or poly-adenylation signal.

In some embodiments, the promoter is selected from the group consisting of, but not restricted to, an EF1α promoter, CAG promoter, PGK promoter, Tet-on or Tet-off promoter, a T7 promoter, or a CMV promoter.

In some embodiments, the promoter drives expression of a reporter gene incorporated in the transposon.

In some embodiments, the reporter gene is selected from the group consisting of: a gene encoding a fluorescent protein; a gene capable of use as a selectable marker by conferring resistance to a chemical agent that kills eukaryotic or prokaryotic cells; or an enzyme capable of converting a chemical substrate into a colorimetric, luminescent, or fluorescent reporter; and combinations thereof.

In some embodiments, the gene encoding a fluorescent protein is selected from, but not restricted to, the group consisting of green fluorescent protein, tdTomato, eGFP, and eCFP.

In some embodiments, the gene capable of use as a selectable marker by conferring resistance to a chemical agent that kills eukaryotic or prokaryotic cells is selected from the group consisting of, but not restricted to, puromycin N-acetyl-transferase, providing resistance to puromycin; either of two aminoglycoside 3' phosphotransferase genes encoded by Tn5 and Tn601 (i.e., a neo gene), providing resistance to G418; or hygromycin phosphotransferase, providing resistance to hygromycin.

In some embodiments, the enzyme capable of converting a chemical substrate into a colorimetric, luminescent, or fluorescent reporter selected from the group consisting of, but not restricted to, beta-galactosidase or beta-lactamase, cleaving x-gal, and GeneBLAzer, respectively.

In some embodiments, the RNA transcript produced by the promoter does not encode a splice donor site between the promoter and the transposon end.

In some embodiments, the transposon does not comprise a poly-adenylation (poly-A) termination signal between the promoter and the transposon end.

In some embodiments, the DNA comprising the transposon encodes a self-cleaving ribozyme such as, but not restricted to, the hammerhead ribozyme immediately downstream of the transposon end.

In some embodiments, the construct encodes a bacterial or eukaryotic ribosomal RNA sequence (e.g. 5S, 18S) downstream of the transposon end.

In some embodiments, the transposon encodes a Woodchuck Hepatitis Virus (WHP) Posttranscriptional Regulatory Element (WPRE).

In some embodiments, the genome-associated protein is a transcription factor, a general transcriptional mediator, or a chromatin reader, writer, or eraser.

In some embodiments, the genome-associated protein and the transposase are separated by a peptide linker.

In some embodiments, the DNA-binding protein is selected from the group consisting of, but not restricted to, Brd4, Sp1, Hb9, Olig2, Ngn2, Med1, Creb, p53, Usf1, or FoxA2.

In some embodiments, the genome comprising: (i) introducing a self-reporting transposon (SRT) into one or more cells; (ii) introducing DNA encoding a transposase into the same cells; (iii) allowing the transposase to direct the insertion of SRTs into cellular genomes; (iv) mapping the locations of SRT insertions using cellular mRNA. In some embodiments, the genomic locations of protein-genome interactions, which can include direct binders of DNA (e.g., transcription factors) or DNA-associated proteins (e.g., chromatin readers and remodelers), can be identified by: (a) introducing DNA encoding a fusion of a GAP and transposase in step (ii); (b) determining the locations of transient or stable GAP-DNA interactions from the aggregated SRT location data, after step (iv).

In some embodiments, the SRT construct and the gene encoding the transposase (or the GAP-transposase fusion) are delivered to the cell with known methods of gene delivery including, but not restricted to: (i) electroporation; (ii) lipofection; (iii) viral delivery (e.g. lentivirus, adenovirus, herpes simplex virus, adeno-associated virus, rabies virus); (iv) micro-injection; (v) sono-poration; or (vi) magnetofection.

In some embodiments, the SRT construct is encoded on plasmid DNA.

In some embodiments, the transposase gene or GAP-transposase fusion protein is encoded on plasmid DNA.

In some embodiments, the transposase or GAP-transposase fusion is delivered to the cell via mRNA or directly as a protein, using known methods for mRNA or protein delivery including, but not restricted to: (i) electroporation; (ii) lipofection; (iii) viral delivery (e.g. integration deficient lentivirus); (iv) micro-injection; (v) sono-poration; or (vi) magnetofection.

In some embodiments, the transposase is delivered to the cell by engineering its genome using known methods (e.g. homologous recombination, Cas9 mediated homologous recombination). The genome can be engineered so that the unfused transposase protein is expressed or so that one or more copies of an endogenous gene encoding a GAP fusion is fused to the transposase, optionally with a sequence encoding a peptide linker.

In some embodiments, one or more copies of the SRT is delivered to the cell by engineering its genome using known methods (e.g. pro-nuclear injection, homologous recombination, Cas9 mediated homologous recombination).

In some embodiments, (i) the transposon is selected from the DDE family of transposons (e.g., piggyBac transposon, Sleeping Beauty transposon, Ty5 transposon), the rolling circle/Y2 family of transposons (e.g., helitrons), or the TP-retrotransposon family (e.g., LINE-1 retrotransposon); (ii) the transposase used to insert the transposon into the cellular genome is selected from the DDE family of transposases (e.g., piggyBac, Sleeping Beauty, Ty5), the rolling circle/Y2 family of transposons (e.g., Helraiser), or the TP-retrotransposon family (e.g., LINE-1), or any hyperactive variants of these transposases; and (iii) the transposase employed corresponds to the chosen transposon In some embodiments, the transposase or GAP-transposase fusion is fused to a destabilized domain (DD) so that transposition of SRTs can be induced by a small molecule such as, but not restricted to: Shield-1, FK506, rapamycin, trimethoprim, or tamoxifen.

In some embodiments, the DD is selected from the group consisting of, but not restricted to, a mutant of FKBP12, $E. coli$ dihydrofolate reductase, or an estrogen receptor protein.

Yet another aspect of the present disclosure provides for a method for mapping the insertion locations of SRTs that have been transposed into the DNA of a plurality of cells (e.g., $10^2$-$10^8$ cells) by, (i) harvesting total RNA in bulk from the cells; (ii) reverse transcribing mRNA into cDNA using a poly-T primer tailed with a universal sequence (e.g., the SMART primer); (iii) PCR amplifying the cDNA using a primer specific either for the transposon end or the reporter gene and a primer (optionally biotinylated) specific to the universal sequence; (iv) tagmenting the PCR product (e.g., using a Nextera kit); (v) amplifying using the transposon end primer and tagmentation primers suitable for amplifying the PCR product encoding the junction between the inserted transposon and the genome (e.g., a Nextera primer); and (vi) sequencing the tagged DNA fragments by employing $2^{nd}$ or $3^{rd}$ generation sequencing technology (e.g., Illumina or PacBio) using sequencing primers that are designed so that the transposon-genome junction is sequenced.

In some embodiments, unwanted transposon sequence from the PCR product (e.g., as can be the case when mapping LINE-1 retrotransposons) is removed after step (iii) by, (a) capturing the biotinylated PCR product on streptavidin-coated magnetic beads; (b) optionally, tailing the ends of the PCR product with a dideoxynucleotide (ddNTP); (c) incubating the PCR products in vitro with Cas9 and guide RNAs (gRNAs) to specifically cut the unwanted transposon sequence; (d) end repairing, A-tailing, and ligating Y-adapters to the cut PCR products "on bead"; (e) amplifying by PCR with a primer specific for the Y-adapter and a primer specific to the universal sequence; (f) purifying the resulting PCR product and proceeding with step (iv). In some embodiments, (i) the cDNA is sequenced directly after step (iii) using $2^{nd}$ or $3^{rd}$ generation sequencing technology (e.g., Illumina NextSeq, Pacific Biosciences, Oxford Nanopore) with sequencing primers that are designed so that the transposon-genome junction is sequenced, and/or (ii) the reverse transcription as described herein, step (ii) is performed using short random primers of 6 to 10 nucleotides tailed with a universal sequence (e.g., the SMART primer), and/or (iii) the PCR product produced as described herein, step (vi) is sequenced using known methods for the high throughput sequencing of PCR products (e.g., shearing by sonication and the ligation of Illumina adapters).

Yet another aspect of the present disclosure provides for a method for mapping the genomic locations of SRTs that have been inserted into DNA of a plurality of cells (e.g., $10^2$-$10^8$ cells) using a bacteriophage (e.g. T7, T3, SP6) promoter, comprising: (i) introducing into cells an SRT with a bacteriophage promoter in the transposon (as opposed to a eukaryotic promoter, such as EF-1α); (ii) harvesting cellular DNA; (iii) shearing the DNA and ligating onto fragments a Y-linker comprising a universal primer, or tagmenting the DNA (e.g., using a Nextera kit); (iv) performing an in vitro transcription reaction; (v) performing first strand synthesis using a universal priming sequence; (vi) amplifying by PCR, using a universal primer (optionally biotinylated) and a primer targeting the transposon end; and (vii) optionally, removing unwanted transposon sequence from the PCR products by following the method described herein.

In some embodiments, the primers used in the final step are tailed with Illumina P5 and P7 (and optionally Illumina Seq1 and Seq2) sequences and the amplification product is loaded on an Illumina sequencer and sequenced.

Yet another aspect of the present disclosure provides for a method of mapping the locations of SRTs and simultaneously measuring mRNA abundance from a plurality of single cells in parallel, so that thousands or tens of thousands of cells can be analyzed in one experiment, composed of the following steps: (i) Converting the mRNA from single cells into cDNA that is labeled at its 3' end with a cell barcode, a unique molecular index (UMI), and a universal priming sequence using known methods for single-cell RNA-seq such as 10× Chromium, Drop-Seq, or InDrop. All of the mRNA molecules from a single cell will be tagged with the same cell barcode, but different UMIs; (ii) Separating the pooled cDNA from all cells analyzed in the experiment into two fractions; (iii) Recovering the transcriptomes of the single cells by completing the single cell RNA-seq protocol chosen in step (i) using one of the cDNA fractions; (iv) Mapping the genomic locations of SRTs and assigning the SRTs to cell barcodes by circularizing SRT cDNA to physically bring the cell barcode in apposition to the insertion site and then performing Illumina sequencing; This is achieved by (a) amplifying SRT cDNA by performing PCR with primers that bind to the universal priming sequence next to the cell barcode and the transposon end, wherein, these primers are biotinylated and carry a 5' phosphate group; (b) optionally, removing unwanted transposon sequence from the PCR products described above; (c) diluting the PCR products of this amplification and performing a self-ligation reaction; (d) shearing the self-ligated products and capturing the ligation junction and flanking sequences by pulling these fragments down with streptavidin-coated magnetic beads; (e) preparing this fragment for Illumina sequencing by performing end repair, A-tailing, and adapter ligation "on bead"; (f) performing a final PCR step to add the required Illumina sequences for high-throughput sequencing. The standard Illumina read 1 primer will anneal and read the cell barcode and UMI, while a custom read 2 primer, annealing to the end of the transposon, reads into the genome; and/or (g) analyzing the Illumina sequencing reads to collect both the location of each SRT insertion as well as the cell barcode corresponding to its cell of origin.

Yet another aspect of the present disclosure provides for a computational method for ascribing SRT insertions to specific cell types composed of the following steps: (i) identifying cell types from the scRNA-seq library as described herein, step (iii) using known methods of scRNA-seq analysis (e.g., Seurat, scanpy); (ii) isolating the sets of cell barcodes comprising each cell type; (iii) using the cell type-specific barcodes to filter the barcoded single cell SRT insertions isolated as described herein, step (iv); and (iv) optionally, determining cell type-specific locations of transient or stable GAP-DNA interactions from the aggregated barcoded SRT location data.

In some embodiments, the single-cell RNA-seq methodology used includes, but is not restricted to, the following platforms: 10× Genomics Chromium, Drop-seq, Fluidigm, InDrop, MARS-seq, SCI-seq, SPLiT-seq, Microwell-seq.

In some embodiments, the transposon system used includes, but is not restricted to, the following: DDE transposons (e.g., piggyBac transposons, Sleeping Beauty transposons), rolling circle/Y2 transposons (e.g., helitron transposons), or TP-retrotransposons (e.g., LINE-1); and the respective transposase.

Yet another aspect of the present disclosure provides for a computational method for filtering out intermolecular ligations in the analysis of single cell calling cards, comprising: (i) mapping the 5' ends (without cellular barcode information) and the 3' ends (with cellular barcode information but with imprecise information about the insertion site); and (ii) verifying that the location of the 3' end maps nearby the 5' end on the genome (e.g., less than 5 kb).

Yet another aspect of the present disclosure provides for a computational method for filtering out intermolecular ligations in the analysis of single cell calling cards by requiring that a given 5'-3' pair in the circularization data is represented by at least 2 unique molecular identifiers (UMIs).

In some embodiments, (a) if a self-cleaving ribozyme is present, the self-cleaving ribozyme degrades all mRNA produced by uninserted transposons (e.g., on donor plasmids); (b) if a ribosomal RNA (e.g., 5S, 18S) sequence is present, the ribosomal RNA sequence marks RNA transcribed from donor plasmids, and sequence contamination is removed using a bacterial or eukaryotic ribosomal RNA depletion kit; or (c) if a Woodchuck hepatitis posttranscriptional regulatory element (WPRE) is present, the WPRE stabilizes the mRNA molecule.

Yet another aspect of the present disclosure provides for a method of cellular lineage tracing, comprising: (i) introducing into one or more cells an undirected transposase that can integrate at many different locations in the genome described herein; (ii) introducing into the same cells the SRT described herein; (iii) allowing the cells to divide and/or differentiate while they express the transposase so that SRTs are inserted into different genomic locations at different times along a cellular lineage, so that each SRT insertion serves as a lineage-specific barcode; (iii) mapping the location of SRT insertions and mRNA transcriptomes from single cells as described above; and (iv) using single cell transcriptomes to ascertain, for each of a plurality of cells, information about the cell's identity and genealogical relationships between these cells using information about the number of shared SRT insertion events between cells.

In some embodiments, the method provides for identifying novel cell types and reconstructing their genealogical context.

Yet another aspect of the present disclosure provides for a method of reading out transposon mutagenesis screens, comprising: (i) introducing into cells an SRT as a mutagen as described herein; and (ii) reading out the transposon insertions as described herein.

In some embodiments, the method is capable of measuring the transcriptome, genome, methylome, chromatin accessibility, cell-surface markers, or combinations thereof.

In some embodiments, genomic locations of inserted transposons can be mapped from either mRNA, wherein the use of mRNA enables both higher efficiency and compatibility with single-cell transcriptomics.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 7A-FIG. 7F is a series of schematics, scatter plots, and graphs showing single cell calling cards (scCC) maps BRD4 binding and SP1 in single cells. (A) Schematic of the sCC library preparation strategy from scRNA-seq libraries. Self-reporting transcripts are amplified using biotinylated primers and circularized, which brings the cell barcode and unique molecular index (UMI) in close proximity to the transposon-genome junction. Circularized molecules are sheared, captured with streptavidin, and Illumina adapters are ligated. Custom sequencing yields the cell barcode and UMI with read 1 and the genomic insertion site with read 2. (B) Barnyard plot of HCT-116 and N2a cells transfected with SRTs shows clean segregation of cell types. Most cells were assigned either human insertions or mouse insertions, with a minority (7.8%) containing insertions from both species. (C) Human HCT-116 and K562 cells were transfected with PB-SRT-Puro and HyPBase and subsequently subjected to scRNA-seq. Two clear cell types emerge revealing each constituent cell population. (D) scCC deconvolves HyPBase insertions from HCT-116 and K562 cells, identifying shared and specific BRD4 binding sites. (E) scCC on HCT-116 cells transfected with SP1-HyPBase identifies SP1 binding sites. (F) SP1-HyPBase peaks from scCC data show strong central enrichment for SP1 ChIP-seq signal.

FIG. 12A-FIG. 12F is a series of graphs showing SP1 fused to hyperactive piggyBac (SP1-HyPBase) also redirects insertions to SP1 binding sites. (A) SP1-HyPBase, like SP1-PBase, can also be used to identify SP1 binding sites. (B) Insertions at SP1-HyPBase-derived peaks show high reproducibility between biological replicates. (C) Mean SP1 ChIP-seq profile at peaks shows strong central enrichment. (D) Heatmap of SP1 ChIP-seq signal across all peaks, expressed as $\log_2(FC)$ from the input control. (E) SP1-HyPBase redirects insertions to TSSs, CpG islands, and unmethylated CpGs ($p<10^{-9}$, G test of independence). (F) Motif analysis of SP1-HyPBase peaks identifies the SP1 motif. IPM: insertions per million mapped insertions; FC: fold change.

FIG. 16A-FIG. 16D is a series of plots showing filtering single cell SRTs reduces intermolecular artifacts. (A) Barnyard plot from scRNA-seq of HCT-116 and N2a cells shows clean resolution of cell types. Cells were assigned as human or mouse if at least 80% of transcripts in each cell mapped to hg38 or mm10, respectively, or a multiplet otherwise. 3.2% of cells were classified as multiplets. (B) Barnyard plot from scCC of HCT-116 and N2a cells without filtering. 25.1% of cells were called as multiplets. (C) Distribution of species purity from unfiltered scCC data. The x-axis is the proportion of transcripts mapping to the human or mouse genomes. (D) Distribution of species purity after filtering scCC data.

FIG. 17A-FIG. 17I is a series of graphs showing validation and performance of in vitro single cell calling cards. (A) Expression of three marker genes (AKAP12, PRAME, XIST) identify HCT-116 (n=12,891) and K562 (n=11,912) cells from scRNA-seq libraries. (B) Distributions of genes per cell by cell type. (C) Distributions of transcripts per cell by cell type. The numbers of genes and transcripts detected per cell were comparable between HCT-116 and K562 cells. (D) Distributions of recovered HyPBase insertions in HCT-116 and K562 cells. (E) Mean BRD4 ChIP-seq signal at HyPBase peaks in HCT-116 cells compared to randomly permuted peaks ($p<10^{-9}$, KS test). (F) Mean BRD4 ChIP-seq signal at HyPBase peaks in K562 cells compared to randomly permuted peaks ($p<10^{-9}$, KS test). (G) Distributions of recovered insertions in HCT-116 cells transfected with PB-SRT-Puro and either HyPBase or SP1-HyPBase. (H) Reproducibility of normalized insertions deposited by HyPBase and recovered by scCC at BRD4 binding sites in HCT-116 cells. (I) Reproducibility of normalized insertions deposited by SP1-HyPBase and recovered by scCC at SP1 binding sites in HCT-116 cells. KS: Kolmogorov-Smirnov.

FIG. 23 demonstrates that the L1 transposon can be controlled by a small molecule shield when a degradation domain (DD) is fused to ORF1.

FIG. 26A depicts a FACS plot of a fluorescent reporter of transcription with and without transposase, and FIG. 26B demonstrates that the rate of transposition (which is proportional to fluorescence) can be tuned by adding different amounts of a chemical inducer.

DETAILED DESCRIPTION OF THE INVENTION

Figure 1A:
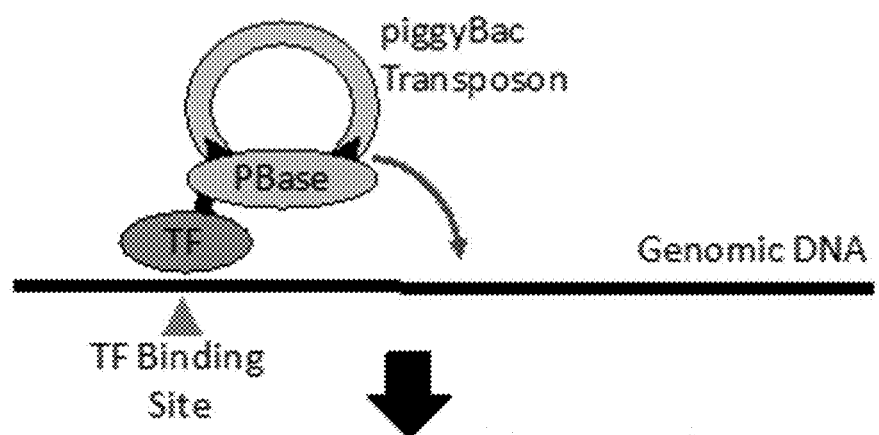
FIG. 1A-FIG. 1B is a schematic depicting self-reporting calling cards. (A) By fusing a piggyBac transposase (PBase) to a transcription factor (TF), the TF is endowed with the ability to insert transposon DNA into the genome. B) The transposon contains an EF1α promoter that drives transcription into the genome, which is eventually terminated by a cryptic or endogenous poly-adenylation signal sequence in the genome. Thus, the transposon reports its location via mRNA.

The present disclosure is based, at least in part, on the discovery of a first-of-its-kind transposon system that reports its precise location (i.e., a self-reporting transposon (SRT)). Although other (e.g., gene trap) transposons have transcribed through their long terminal repeats (LTRs), they have never reported the LTR-genome junction.

Applications can include mapping the locations of SRTs from thousands of single cells in parallel, while simultaneously measuring mRNA abundance from the same single cells; analyzing TF binding in a small number of cells in bulk, without single cell resolution, which is also useful for some applications; lineage tracing; or as an improved readout for transposon mutagenesis screens.

In situ measurements of transcription factor (TF) binding are confounded by cellular heterogeneity and represent averaged profiles in complex tissues. Single cell RNA-seq (scRNA-seq) is capable of resolving different cell types based on gene expression profiles, but no technology exists to directly link specific cell types to the binding pattern of TFs in those cell types.

Described herein are self-reporting transposons (SRTs) and their use in single cell calling cards (scCC), a novel assay for simultaneously capturing gene expression profiles and mapping TF binding sites in single cells.

First, it was shown how the genomic locations of SRTs can be recovered from mRNA. Next, it was demonstrated that SRTs deposited by the piggyBac transposase can be used to map the genome-wide localization of the TFs SP1, through a direct fusion of the two proteins, and BRD4, through its native affinity for piggyBac. The scCC method is then presented, which maps SRTs from scRNA-seq libraries, thus enabling concomitant identification of cell types and TF binding sites in those same cells. Also shown is the recovery of cell type-specific BRD4 and SP1 binding sites from cultured cells. Finally, Brd4 binding sites were mapped in the mouse cortex at single cell resolution, thus establishing a new technique for studying TF biology in situ.

The present disclosure provides for methods for the mapping of transposon insertions from single cells (providing for single cell analysis). As described herein, a new transposon reporter system is used to report sites of transcription factor (TF)-DNA interaction. The present technology provides for methods to identify TF-DNA interactions in vitro and in vivo. This technology not only maps the site of interaction but can also quantify the abundance of the transcript (i.e., a length of RNA or DNA that has been transcribed respectively from a DNA or RNA template).

As described herein, the 3' region flanking the terminal repeat is transcribed and the transcript is terminated by a cryptic poly-A signal sequence (e.g., AAUAAA sequence (SEQ ID NO: 12)) or transcriptional termination sequence in the genome allowing for quantitative single cell analysis, cell fate mapping, or transposon mutagenesis screens, among other applications.

The ability to chronicle transcription-factor binding events throughout the development of an organism can facilitate mapping of transcriptional networks that control cell-fate decisions. This method permanently records protein-DNA interactions in mammalian cells. The transcription factors are endowed with the ability to deposit a transposon into the genome near to where they bind. The transposon becomes a "calling card" that the transcription factor leaves behind to record its visit to the genome. The locations of the calling cards can be determined by massively parallel DNA sequencing.

Previously developed Transposon Calling Cards, allow transient molecular interactions to be captured non-destructively, during a controlled window in time, and then read out at a later point in time. The new self-reporting Calling Cards are transposons that have been engineered to contain a strong promoter (e.g., Ef1 alpha) that drives the transcription of a reporter gene that has no poly-A termination signal. When a self-reporting transposon is inserted into the genome, the reporter gene is transcribed, and transcription continues through the piggyBac terminal repeat and into the neighboring genomic region until a cryptic poly-A termination signal is encountered. The present disclosure provides for methods of mapping transposon insertions from single cells, in conjunction with Drop-Seq or 10× Chromium technologies. These technologies analyze RNA expression genome-wide in thousands of individual cells at once.

Self-Reporting Transposon (SRT) Construct

The self-reporting transposon construct as described herein comprises a transposon that can report its location in the cellular RNA fraction. The SRT construct can be used in conjunction with a transposase or a fusion of a transposase with a genome-associated protein (GAP; e.g., a transcription factor, a general transcriptional mediator).

Reporter

As described herein, the SRT construct can comprise a reporter. The reporter can be any reporter known in the art. For example, the reporter can be a screenable or selectable reporter gene. As another example, the reporter can be a gene capable of encoding a fluorescent protein (e.g., green fluorescent protein, tdTomato, eGFP, eCFP).

As another example, the reporter can be a gene capable of use as a selectable marker by conferring resistance to a chemical agent that kills eukaryotic or prokaryotic cells (e.g., puromycin N-acetyl-transferase, providing resistance to puromycin; either of two aminoglycoside 3' phosphotransferase genes encoded by Tn5 and Tn601 (i.e., the neo gene), providing resistance to G418; or hygromycin phosphotransferase, providing resistance to hygromycin).

As another example, the reporter can be an enzyme capable of converting a chemical substrate into a colorimetric, luminescent, or fluorescent reporter (e.g., beta-galactosidase or beta-lactamase, cleaving x-gal and GeneBLAzer, respectively).

As described herein, a reporter gene having no poly-A termination signal, enables RNA polymerase II (Pol II) to transcribe the reporter gene contained in the transposon and continue through the terminal repeat (TR) or end of the transposon insertion element into the flanking genomic sequence.

As another example, the reporter can be an interrupted reporter gene (e.g., itdTomato).

Promoter

As described herein, a promoter capable of initiating transcription can be incorporated into the SRT construct, for example in the insertion element (or donor). Any promoter capable of initiating transcription of RNA or a reporter gene can be used. Preferably a constitutive promoter or a strong promoter, such as EF1a, CMV, or CAG can be used. In some embodiments, a T7 promoter can be used. Other promoters that can be used include a ubiquitous promoter (e.g., Ubq-C) or an inducible promoter (e.g., a tet-inducible promoter). Cell-type specific promoters can be used. For example, a neuron specific promoter (e.g., Syn1) can be used in the constructs described herein.

Insertion Element (Donor)

As described herein, the transposon system comprises an insertion element capable of being inserted into a genome. An insertion element (also known as a donor, an IS, an insertion sequence element, or an IS element) is a short DNA sequence that acts as a simple transposable element (TE). The insertion element can comprise a reporter and/or a promoter. The insertion element can provide a sequence that can be read out and reported.

Transposons and Transposases

As described herein, the self-reporting transposon is inserted into a cellular genome by the corresponding transposase protein, which can be delivered to the cell separately from the transposon, or which can be encoded in the transposon DNA. Together, the transposon and transposase comprise a transposon system. The transposon system can be any transposon system known in the art (see e.g., Munoz-Lopez et al. 2010 Curr Genomics. 11(2) 115-128). A transposase is an enzyme that binds to the end of a transposon and catalyzes its movement to another part of the genome by a cut and paste mechanism or a replicative transposition mechanism. More specifically, the transposase recognizes the terminal repeats to excise the transposon DNA, which is then inserted into a new genomic location by cut and paste or copy and paste mobilization. DNA transposons can inactivate or alter the expression of genes by insertion within introns, exons, or regulatory region. But here the DNA transposons are used to express an RNA transcript identifying the location of a TR. For example, a transposon can be a DDE transposon (e.g., piggyBac transposon, hyperactive variant of piggyBac transposon, Sleeping Beauty transposon, Ty5 transposon), a rolling circle/Y2 transposon (e.g., Helitrons, such as Helraiser), or a TP-retrotransposon (e.g., LINE-1 retrotransposon).

Genome Associated Protein

As described herein, a genome-associated protein:transposase fusion can be used to insert SRT constructs into cellular genomes. Any genome-associated protein known in the art can be used.

As described herein, the genome-associated protein can be a trans-acting factor or element. Trans-acting elements can be a transcription factor (TF) or other DNA-binding protein which recognizes and binds to specific sequences in a cis-acting element to initiate, enhance, or suppress transcription. A transcription factor can regulate multiple genes or it may work in a combinatorial or complex manner to bind to the cis-regulatory elements at multiple transcription factor binding sites to generate a huge repertoire of unique and precise control patterns. It is estimated that the human genome encodes approximately 1800 transcription factors (Venter et al., 2001).

As described herein, a TF-transposase fusion can be used to deliver the SRT construct. For example, any TF known in the art can be used to deliver the SRT construct (e.g., Foxa1, Hnf4a, Sp1, Tbp, Hb9, Jun, Olig2, Ngn2, Creb, Fos, Egr1). As another example, the genome-associated protein can be any protein that interacts indirectly with genomic DNA, such as Brd4, Med1, Chd4, Chd2, Bap1, all of which bind to other genome-associated proteins.

Transcription factors (TFs) (or sequence-specific DNA-binding factors) are proteins that control the rate of transcription of genetic information from DNA to messenger RNA, by binding to a specific DNA sequence. The function of TFs is to regulate—turn on and off—genes in order to make sure that they are expressed in the right cell at the right time and in the right amount throughout the life of the cell and the organism. Groups of TFs function in a coordinated fashion to direct cell division, cell growth, and cell death throughout life; cell migration and organization (body plan) during embryonic development; and intermittently in response to signals from outside the cell, such as a hormone.

A defining feature of TFs is that they contain at least one DNA-binding domain (DBD), which attaches to a specific sequence of DNA adjacent to the genes that they regulate. TFs are grouped into classes based on their DBDs.

Other genome-associated proteins such as coactivators, chromatin remodelers, histone acetyltransferases, histone deacetylases, kinases, and methylases are also essential to gene regulation, but lack DNA-binding domains, and therefore are not considered TFs, but these can still be used to direct the insertion of SRTs into the genome.

Regulation of Transposase Activity

As described herein, the genome-associated protein-transposase fusion can be further linked to a destabilized domain (DD) to achieve temporal control over transposition. Destabilized domains are ligand binding proteins that have been mutated so that they are unstable and the DD, as well any protein fused to the DD, is degraded by the cellular machinery. However, in the presence of the corresponding ligand molecule, termed a shield, the DD domains are stabilized. There are several proteins that can act as DDs, such as mutants of FKBP12 (with rapamycin as the shield), *E. coli* dihydrofolate reductase (DHFR, with trimethoprim as the shield), and the estrogen receptor protein (ERT2, with tamoxifen as the shield).

Delivery of SRTS and Transposases

As described herein, the SRT construct can be delivered to the cell via known methods of gene delivery. The SRT construct can delivered to a cell via a gene delivery method such as electroporation, lipofection, a viral vector (e.g., lentivirus, adenovirus, herpes simplex virus, adeno-associated virus), micro-injection, sonoporation, or magnetofection. The transposase can be delivered to the cell encode on DNA or RNA, or directly as a protein, using known methods of DNA delivery (as listed above) or known methods for RNA or protein delivery, such as electroporation, lipofection, a viral vector (e.g. integration defective lentivirus), micro-injection, sonoporation, or magnetofection.

Mapping Locations of SRTS

The present disclosure provides methods for mapping the locations of SRTs from cellular RNA, which provides advantages over other methods of transposon mapping. The method, which can be used to analyze cells with SRTs transposed into their genomic DNA, can comprise the following steps:

(i) harvesting total RNA in bulk from the cells;
(ii) reverse transcribing mRNA into cDNA using a poly-T primer tailed with a universal sequence (e.g., the SMART primer);

(iii) PCR amplifying the cDNA using a primer specific either for the transposon end or the reporter gene and a primer (optionally biotinylated) specific to the universal sequence;

(iv) tagmenting the PCR product (e.g., using a Nextera kit);

(v) amplifying using the transposon end primer and tagmentation primers suitable for amplifying the PCR product encoding the junction between the inserted transposon and the genome (e.g., a Nextera primer); and (vi) sequencing the tagged DNA fragments by employing $2^{nd}$ or $3^{rd}$ generation sequencing technology (e.g., Illumina or PacBio) using sequencing primers that are designed so that the transposon-genome junction is sequenced.

Simultaneous Measurement of SRT Locations and mRNA Transcriptomes from Single Cells The present disclosure provides for methods of mapping the locations of SRTs and simultaneously measuring mRNA abundance from thousands of single cells in parallel (using a protocol combined from 10× Genomics or Drop-Seq single cell methodology and an Illumina paired end kit) (see e.g., Example 1). The method can comprise the following steps:

(i) Converting the mRNA from single cells into cDNA that is labeled at its 3' end with a cell barcode, a unique molecular index (UMI), and a universal priming sequence using known methods for single-cell RNA-seq such as 10× Chromium, Drop-Seq, or InDrop. All of the mRNA molecules from a single cell will be tagged with the same cell barcode, but different UMIs.

(ii) Separating the pooled cDNA from all cells analyzed in the experiment into two fractions.

(iii) Recovering the transcriptomes of the single cells by completing the single cell RNA-seq protocol chosen in step (i) using one of the cDNA fractions.

(iv) Mapping the genomic locations of SRTs and assigning the SRTs to cell barcodes by circularizing SRT cDNA to physically bring the cell barcode in apposition to the insertion site and then performing Illumina sequencing. This is achieved by (a) amplifying SRT cDNA by performing PCR with primers that bind to the universal priming sequence next to the cell barcode and the transposon end. These primers are biotinylated and carry a 5' phosphate group.

(b) optionally, removing unwanted transposon sequence from the PCR products as described herein (c) diluting the PCR products of this amplification and performing a self-ligation reaction.

(d) shearing the self-ligated products and capturing the ligation junction and flanking sequences by pulling these fragments down with streptavidin-coated magnetic beads.

(e) preparing this fragment for Illumina sequencing by performing end repair, A-tailing, and adapter ligation "on bead".

(f) performing a final PCR step to add the required Illumina sequences for high-throughput sequencing. The standard Illumina read 1 primer will anneal and read the cell barcode and UMI, while a custom read 2 primer, annealing to the end of the transposon, reads into the genome.

(g) analyzing the Illumina sequencing reads to collect both the location of each SRT insertion as well as the cell barcode corresponding to its cell of origin.

Computational

Described herein are computational methods to filter out intermolecular ligations and software to (i) identify single cell calling card insertions; (ii) to simulate single cell calling card insertions across a monoclonal population; and (iii) analyze self-reporting Calling Cards.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a composition comprising a GAP, a transcription factor, a transposon, a reporter, or a transposon base. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Methods for the Mapping of Transposon Insertions from Single Cells

Figure 1B:
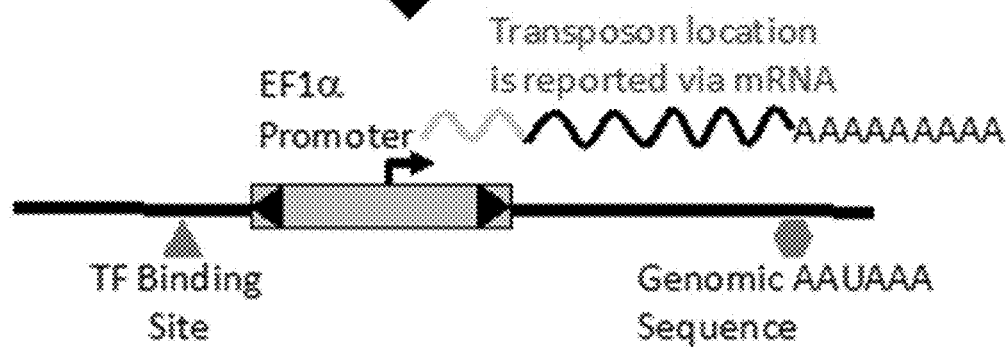

This example describes a technology to reliably measure TF binding from single cells. The inventors have previously developed transposon 'Calling Cards', a method whereby transcription factor (TF) binding is mapped by fusing the transcription factor to the transposase of a transposon, endowing the TF with the ability to deposit transposon DNA near to where it binds. Here is designed a new type of transposon, a self-reporting transposon (SRT), that reports its location in the genome in RNA. Described herein are methods for mapping the locations of SRTs from thousands of single cells in parallel, while simultaneously measuring mRNA abundance from the same single cells. Using these methods, transcription factor binding and mRNA abundance can be mapped from thousands of single cells obtained from a heterogeneous mixture (e.g., brain tissue). Also described here are methods for analyzing TF binding in a small number of cells in bulk (e.g., 100-10000 cells), without single cell resolution, which is also useful for some applications. Finally, this methodology and how it could be used for other applications such as lineage tracing or as an improved readout for transposon mutagenesis screens is described. These methods are described in detail, herein, but briefly described here to point out the features that make the presently disclosed methods new and different.
Self-Reporting Calling Cards Self-reporting Calling Cards builds on the inventors' previous transposon Calling Card method, but represents a significant paradigm shift. Transposon Calling Cards allow transient molecular interactions to be captured non-destructively, during a controlled window in time, and then read out at a later point in time. This is achieved by fusing any TF to the piggyBac transposase, which bestows on the TF the ability to direct transposon insertion into the genome near to where it binds (see e.g., FIG. 1A). This transposon sequence then acts as a "Calling Card" that permanently tags a transient TF-DNA interaction. By sequencing the tags from the genomes of the cells at a later time (e.g., after reprogramming), the molecular events that occurred earlier can be read out. Self-reporting Calling Cards are transposons that have been engineered to contain a strong promoter (e.g., Ef1 alpha) that drives the transcription of a reporter gene that has no poly-A termination signal (see e.g., FIG. 1B). When a self-reporting transposon is inserted into the genome, the reporter gene is transcribed, and transcription continues through the piggyBac terminal repeat and into the neighboring genomic region until a cryptic poly-A termination signal is encountered. Since poly-A termination is governed largely by the pentamer AAUAAA (SEQ ID NO: 12), transcription terminates, on average, $4^6$ or 4096 bp into the genome. Because the EF1α promoter drives transcription in nearly all chromatin states that are capable of being bound by a TF, these transposons "report" their genomic positions via mRNA transcription (H3K9Me2/3-marked heterochromatin, for example, is likely to silence EF1a, but this type of chromatin is not bound by pioneer TFs). The locations of these self-reporting transposons can be read out in single cells by making minor modifications to existing high-throughput single cell RNA-Seq protocols such as Drop-Seq. Some transcripts from inserted transposons either (1) do not acquire a poly-A tail or (2) acquire a poly-A tail far from the insertion site and are primed off of genomic poly-A homopolymers in the transcript (there is evidence that this happens).

Although transposons have been engineered with promoters to initiate transcription, they either transcribe a reporter gene with a poly-A signal, or they transcribe an artificial exon with a splice donor site so that, after the transposon is inserted into the genome the artificial exon is spliced onto nearby genomic exons. What is unique here is 1) the region immediately flanking the transposon terminal repeat is transcribed and reported in cellular mRNA and 2) the transcript is terminated by a cryptic poly-adenylation signal or picks up a poly-A stretch in the genome so that the transcript can be recovered by reverse transcription using a poly-T primer.
Use of a Hammerhead Ribozyme to Prevent Unwanted Donor Recovery One problem that was frequently encountered when performing the Calling Card protocol was unwanted donor transposon recovery. When a calling card experiment was read out, the locations of inserted transposons were mapped by next-generation sequencing. However, unless special methods are used, both transposons inserted into the genome by the TF-transposase fusion as well as un-inserted donor transposons are recovered. These donor transposons are usually delivered to the cell on a plasmid via electroporation, or in an AAV virus via infection, although they can also be engineered to reside in the cellular genome. The method that works well for SRT recovery is to use a hammerhead ribozyme to prevent unwanted donor recovery. Describe herein is how this works when a piggyBac donor transposon is delivered to the cell via plasmid electroporation, but the same principles apply when donor transposons are delivered via AAV or engineered into the cellular genome. The donor plasmid is designed so that a strong promoter inside of the piggyBac transposon drives expression of a reporter gene that has no poly-A termination signal, as previously shown in FIG. 1B. However, in the donor plasmid, a sequence encoding a hammerhead ribozyme is placed immediately downstream of the piggyBac terminal repeat (see e.g., FIG. 2A). Thus, when RNA is transcribed from the donor transposon, it is immediately cleaved due to the action of the hammerhead ribozyme. These transcripts, which lack a poly-A tail, are degraded by the cellular machinery, and those that are not degraded are not reverse transcribed, because they have no binding site for the poly-T primer, and thus are still not recovered. However, when a self-reporting transposon is inserted into the genome, the transposon is no longer adjacent to the hammerhead ribozyme, so transcription continues through the piggyBac terminal repeat and into the neighboring genomic region until a cryptic poly-A termination signal is encountered (see e.g., FIG. 2B). An additional feature of this invention is that because transcripts that are not poly-adenylated are efficiently degraded, the reporter gene effectively reports on whether a transposition event has occurred or not in the cell. For example, if the reporter is the tdtomato gene, red cells correspond to those in which a transposition event has occurred.

It is believed that this method has never been previously described. It was discovered here that it is extremely efficient at removing unwanted donor recovery.

Methods for Mapping TF Binding and mRNA Content from Thousands of Single Cells in Parallel Recently, two methods, Drop-Seq and In-Drops, have been developed that can analyze the mRNA content from thousands of single cells in parallel. 10× genomics has also developed a commercially available platform called Chromium that works in essentially the same way as these two methods. Methods are described herein for mapping transcription factor binding and mRNA content from thousands of single cells in parallel with a novel calling card protocol that uses the presently disclosed SRTs. Here is also described how this protocol is performed using the Drop-Seq platform, but it is well within the skill in the art to modify the protocol for In-Drops or the 10× genomics platform (the platform currently preferred).

Figures 2A, 2B:
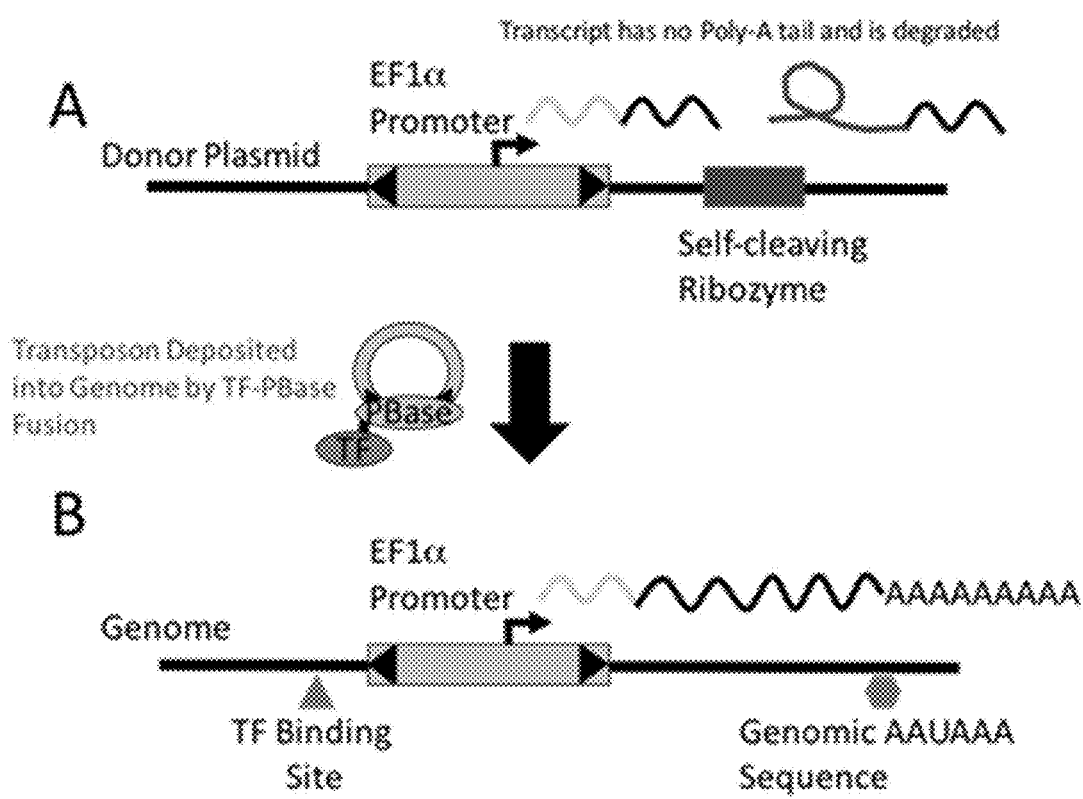
FIG. 2A-FIG. 2B is a schematic depicting how the ribozyme prevents unwanted donor recovery. (A) A self-cleaving ribozyme adjacent to the transposon TR causes transcripts generated from the donor plasmid to be degraded. Also, the lack of a poly-A tail prevents recovery by reverse transcription. (B) After insertion into the genome, transcripts are stable and are poly-A tailed or contain genomic poly-A sequences.

Drop-Seq is a method which can analyze the genome-wide mRNA levels of tens of thousands of cells per day at a cost 5-7 cents per cell. Drop-Seq uses microparticle beads that are coated with oligonucleotides encoding a stretch of 30 poly-Ts at their 3' ends. Each oligonucleotide also possesses a 12-base pair (bp) cell barcode, shared across all sequences on the same bead, and an 8-bp molecular identifier which is unique to each sequence (see e.g., FIG. 2A). Using a microfluidic device, beads in lysis buffer intersect with a flow of single cells in suspension. An oil stream splits this aqueous stream into droplets, where a proportion of these droplets contain one cell and one bead. Once combined, the cell lyses and polyadenylated transcripts are captured on the polythymidine portion of the bead oligonucleotides. Following recovery of the transcriptome-loaded beads (STAMPS: single-cell transcriptomes attached to microparticles) from this emulsion, library preparation is performed in bulk where single-cell resolution is retained as a result of incorporation of the STAMP barcode into the cDNA. cDNA amplification is followed by tagmentation, producing a library of 3' transcript ends tagged with a barcode denoting cell-of-origin (see e.g., FIG. 2A). The Drop-Seq workflow can process a remarkably large number of cells each day; for example, in the seminal publication describing this technology, over 44,000 cells were analyzed. FIG. 2B demonstrates this technology's ability to fully resolve a mixture of human embryonic kidney cells and mouse embryonic fibroblasts at the single-cell level.

Figure 3A:
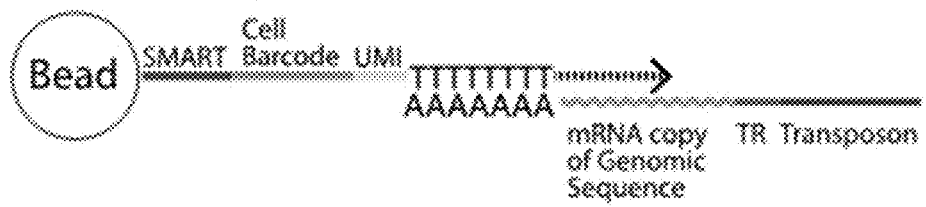
FIG. 3A-FIG. 3I is a schematic depicting the process of reading out self-reporting calling cards in a Drop-seq experiment.

The main technical challenge in this aim is developing a protocol by which self-reporting Calling Cards can be read out by a bead-based single cell methodology such as Drop-Seq. Self-reporting transposons contain a strong EF1α promoter that drives the transcription of mRNA molecules that extend through the terminal repeat of the transposon and into the genome (see e.g., FIG. 1), so that the location of the Calling Card is reported in mRNA. To map a transposon location and assign it to a cell, the STAMP, which is on the 3' end of the cDNA molecule, must be associated with the junction between the transposon and the genome, which is on the 5' end of the cDNA molecule. To do so, the following workflow was developed:

1. mRNA molecules from a single cell are captured on a STAMP-encoded bead in a Drop-Seq droplet as per the standard Drop-Seq protocol (see e.g., FIG. 3A).

Figure 3B:
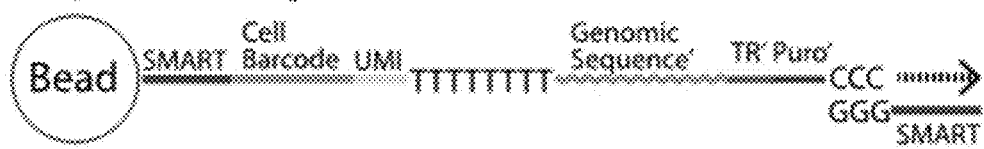
Figure 3C:
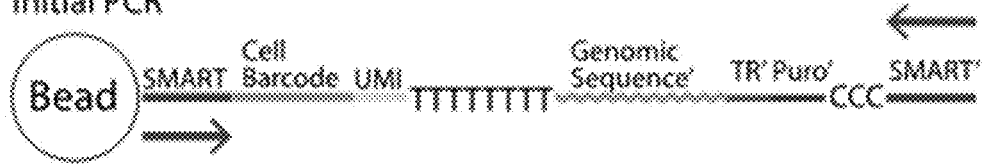

2. All beads are pooled and reverse transcription and template switching is performed (see e.g., FIG. 3B). Each cDNA molecule has a SMART primer on the 5' end and a SMARTer primer on the 3' end (see e.g., FIG. 3B). These primers differ only by 3 base pairs at their 3' terminal ends.

3. All transcripts are PCR amplified using primers that bind the SMART and SMARTer regions.

4. The post-amplified PCR reaction is split in two. Half of the reaction is carried through the standard Drop-Seq protocol to obtain mRNA levels for thousands of single cells.

Figure 3D:
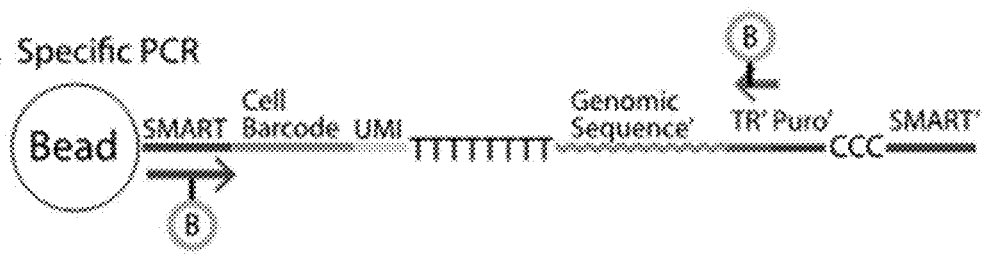

5. Calling Card-generated cDNA is amplified using a biotinylated SMART primer and a biotinylated primer specific for the transposon terminal repeat (see e.g., FIG. 3D). From here on, the protocol used follows the standard Illumina mate pair workflow unless otherwise noted.

Figure 3E:
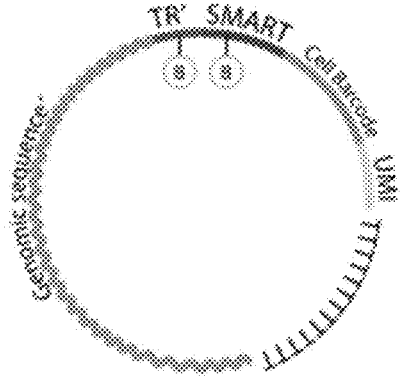
Figure 3F:
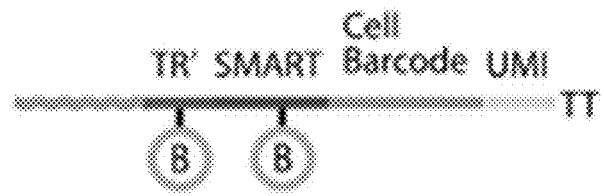
Figure 3G:
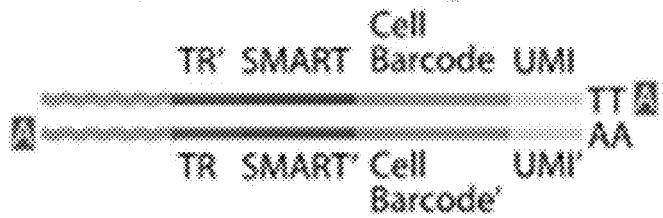

6. This product is circularized by ligation, sheared via sonication, and the biotinylated fragments are pulled down with streptavidin beads (see e.g., FIG. 3E-FIG. 3E).

Figure 3H:
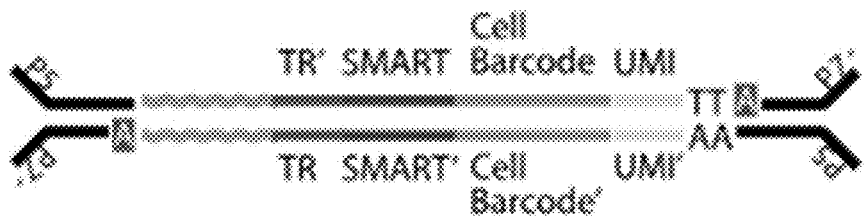
Figure 3I:
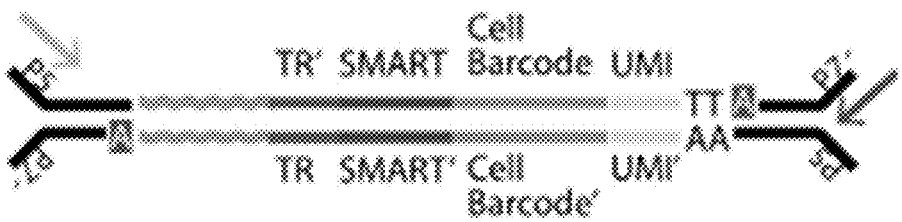

7. Illumina Y-adapters are ligated onto the fragments, an amplification PCR is performed, and the product is loaded on an Illumina NextSeq sequencer (see e.g., FIG. 3H-FIG. 3I).

After sequencing, all mRNA transcripts and Calling Card derived transcripts are mapped to the genome and assigned to a STAMP. STAMPs are clustered by mRNA expression and Calling Card insertions from similar cell types are analyzed together to increase statistical power.

Methods for Recovering SRTs and mRNA Content from Thousands of Single Cells in Parallel The circularization protocol described above is an extension of the illumina paired end kit used to generate paired end reads for genomic sequencing. But the application of this methodology to the problem at hand is highly novel. No other method has been described for Drop-Seq/InDrops/10× that connects the cellular barcode at the 3' end of the cDNA molecule to the 5' end of the molecule.

Molecular Triangulation

Molecular triangulation is a computational method to filter out intermolecular ligations in the analysis of single cell calling cards. One problem with the method described above is that sometimes intermolecular ligations occur, rather than the desired intramolecular ligation. When this happens, an insertion can be assigned to the wrong cell. Here is described a method to filter out intermolecular ligations. To do so, first the circularization protocol described above was performed. From the same sample, the 5' ends (without cellular barcode information) and the 3' ends (with cellular barcode information but with imprecise information about the insertion site) were mapped. Then the 5' and 3' end pairs identified by the circularization protocol were filtered for valid pairs. A valid circularization pair is a 5' and 3' pair for which the transposon insertion site (in the 5' part of the pair) is found in the 5' end mapping data, and the cellular barcode is found in the 3' mapping data and location of the 3' end maps nearby the 5' end on the genome (e.g., less than 5 kb). Another error correction scheme is to require that a given 5'-3' pair in the circularization data is supported by at least N UMIs, where N is at least 2.

It is believed that no similar methods have been described.

Recovering SRTs from Bulk Samples

Small modifications to the protocol can be used to recover transposons in bulk from small numbers of cells. Briefly, RNA is harvested from cells, and reverse transcribed using a poly-T primer tailed with a universal sequence (e.g., the SMART primer). The cDNA is then amplified by PCR using a primer specific for the transposon LTR and the universal sequence, tagmented using the Nextera kit, and amplified using the LTR primer and the Nextera primer and then sequenced. This is identical to the 5' end recovery protocol used in the triangulation method. This method allows for the Calling Card protocol to be performed with fewer cells and also greatly reduces unwanted donor recovery.

SRT Methods for Other Transposons

This technology can be used to map other transposons including the L1 retrotransposon, the Sleeping Beauty transposon, and the Helitron. Constructs were generated for all three of these transposons. The calling card protocol was demonstrated with the Sleeping Beauty transposon system. This may be useful because the unfused Sleeping Beauty transposase inserts transposons into the genome in a more random fashion that does the piggyBac transposase.

Modification—Recovering Transposon Insertion Locations Using a T7 Promoter

For some applications, it may not be desirable to have an active promoter generate the mRNA transcripts that span the transposon genome junction. For example, in some cell types, a given promoter may not be active. Also, there may be some locations in the genome that silence promoters. An alternative strategy is to include a bacteriophage T7 promoter in the transposon, perform the experiment, collect cellular DNA, and then generate the RNA that spans the transposon-genome junction via an in vitro transcription reaction. For example, one could harvest cellular DNA, shear, ligate on a Y-linker with a universal primer, perform an in vitro transcription reaction, perform first strand synthesis using the universal priming sequence, and PCR amplify using a universal primer and a primer targeting the transposon terminal repeat. If these primers are tailed with the Illumina P5 and P7 (and optionally Seq1 and Seq2) sequences, they could be directly loaded on an Illumina sequencer and sequenced.

16s Ribosomal RNA

An alternative method to the ribozyme for removing unwanted donor recover is to insert a 16s ribosomal RNA sequence in the donor construct immediately adjacent to the piggyBac terminal repeat. Bacterial RNA-Seq kits routinely and efficiently remove 16s ribosomal RNA from other bacterial transcripts, so these kits can be used to remove RNA transcripts that are generated by "unhoped" donor molecules.

WPRE Element

The Woodchuck Hepatitis Virus (WHP) Posttranscriptional Regulatory Element (WPRE) is a DNA sequence that when transcribed produces an RNA tertiary structure that causes the mRNA molecule to be extremely stable. By including a WPRE element in the SRT, the RNA molecules produced upon genomic insertion will be stabilized.

Single Cell Lineage Tracing

Natural transposition events are already used to infer phylogenetic relationships between species. The methods described above can be used to perform a similar kind of analysis but at cellular, instead of geologic, time scales. The single cell calling cards protocol described above can be used with only minor modifications to perform lineage tracing. Rather than using TF-directed piggyBac transposases, wild-type, undirected transposases that can integrate anywhere in the genome can be used. Each insertion event can be thought of as a lineage-specific barcode; the content and distribution of lineage barcodes can be used to infer somatic phylogenies. By performing single cell calling cards on a heterogeneous population of cells, novel cell types can be identified and their genealogical context can be reconstructed at the same time.

Reading Out Transposon Mutagenesis Screens

The methods described herein can be used for any application in which it is useful to map the locations of engineered transposons. For example, transposon mutagenesis is a widely used technique, and the methods described here can be applied to this problem.

Figure 4:
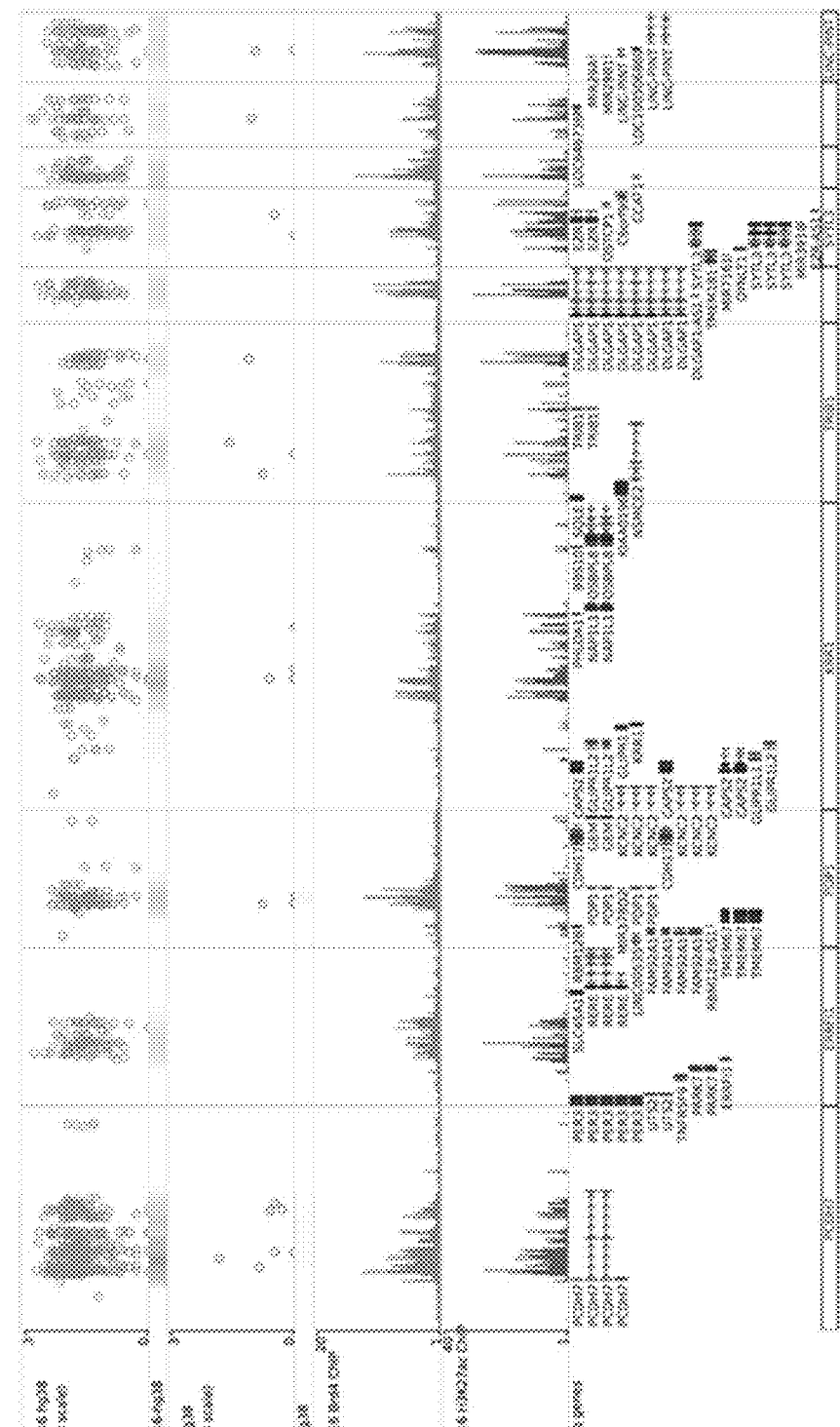
FIG. 4 describes single cell calling cards accurately mapping bromodomain binding. Calling Cards collected from a mixture of human Hct-116 and mouse N2a cells accurately map Brd4 binding. The top four panels show Hct116 calling cards and insertion density and N2a calling cards and insertion density. Below that is Brd4 binding and H3K27ac as determined by ChIP-Seq in bulk.
Figure 7A:
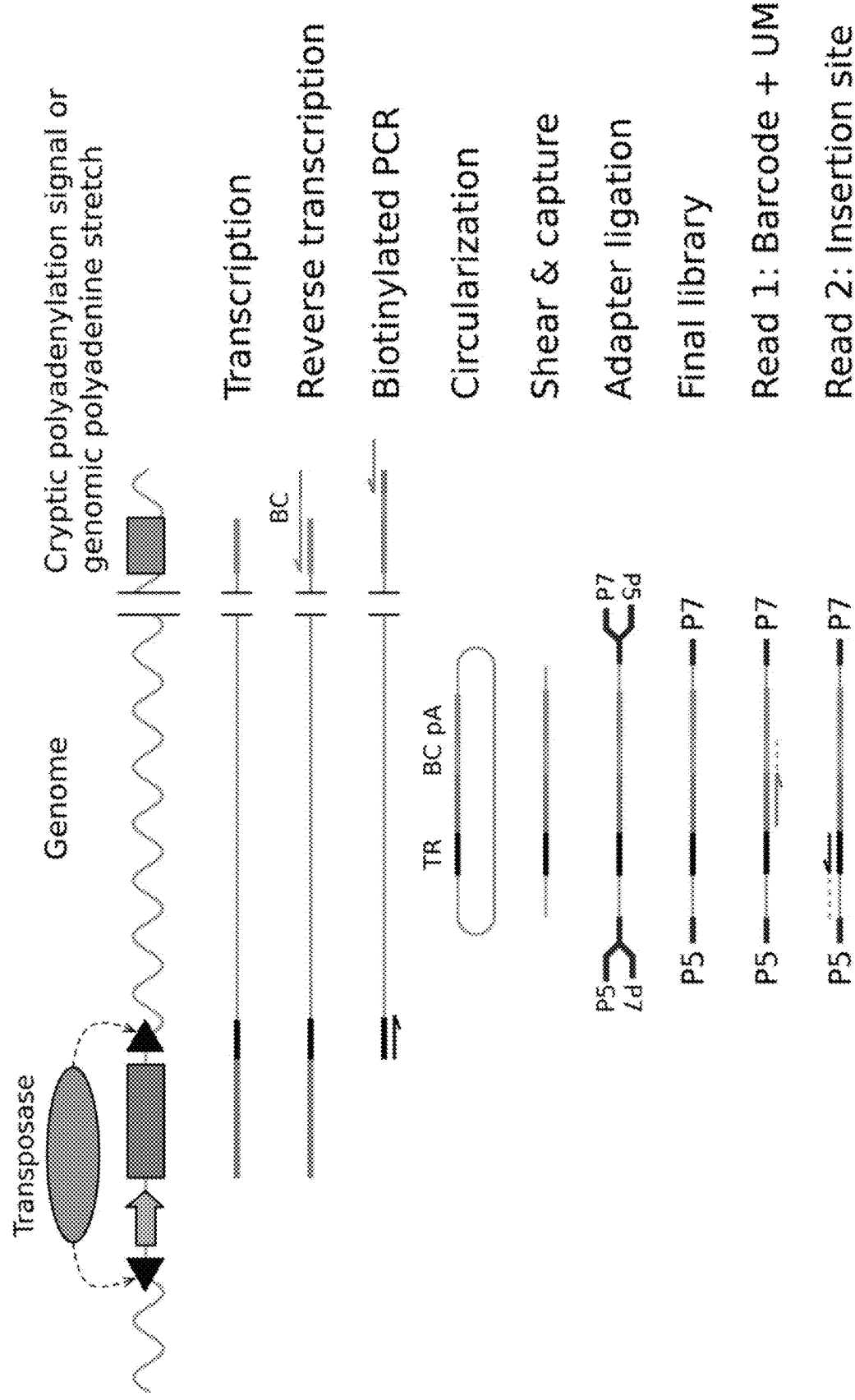
Figure 7C:
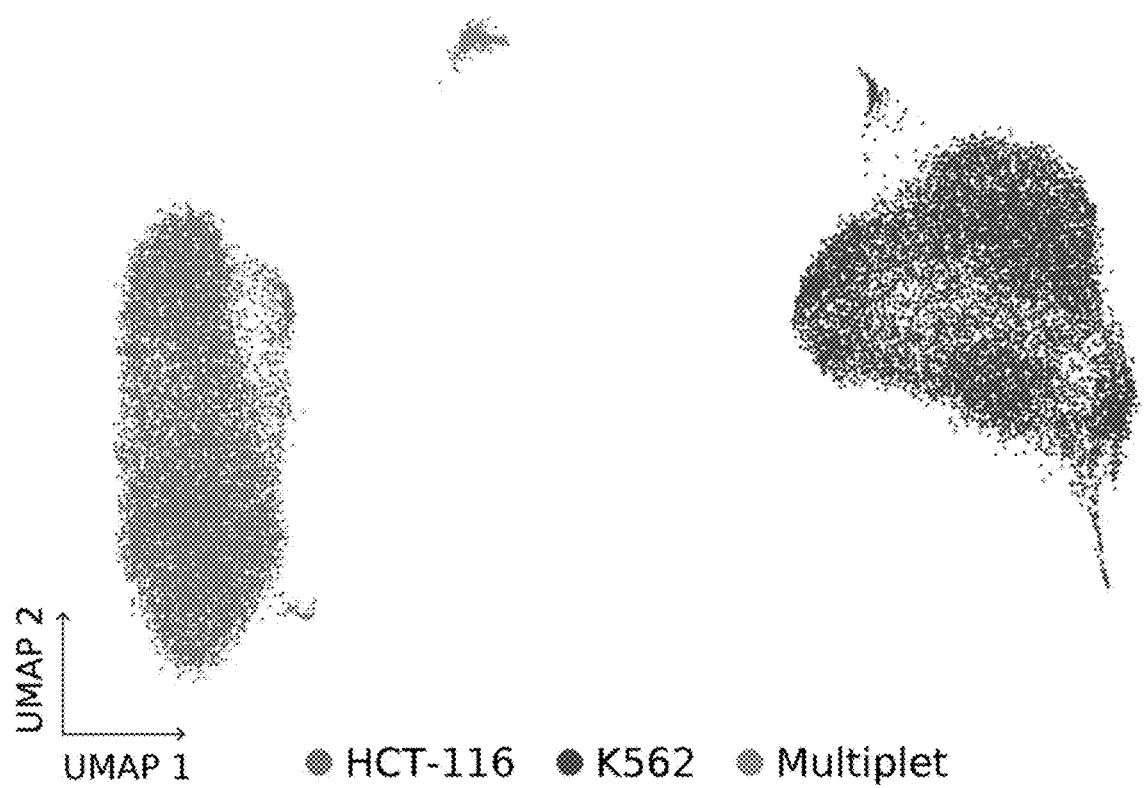

The benchmark for any single cell genomic technology is to take two cell types from different species, mix them together, perform the assay, and assign mapped reads to single cells. If successful, each cell will show reads mapping to either one or the other species, but not both. As described herein, near-perfect species separation of single cell calling card data has been achieved (see e.g., FIG. 7C). Furthermore, the locations of these insertions in HEK293 and mouse N2a cells were mapped. There is excellent concordance with previously measured Brd4 binding and H3K27ac (see e.g., FIG. 4). Together, these results demonstrate that this technology works.

Example 2: Self-Reporting Transposons Enable Simultaneous Readout of Gene Expression and Transcription Factor Binding in Single Cells The following example describes self-reporting transposons (SRTs) and their use in single cell calling cards (scCC), a novel assay for simultaneously capturing gene expression profiles and mapping TF binding sites in single cells.

First, how the genomic locations of SRTs can be recovered from mRNA is demonstrated. Next, it is shown how SRTs deposited by the piggyBac transposase can be used to map the genome-wide localization of the TFs SP1, through a direct fusion of the two proteins, and BRD4, through its native affinity for piggyBac. Then, the scCC method is presented, which maps SRTs from scRNA-seq libraries, thus enabling concomitant identification of cell types and TF binding sites in those same cells. As a proof-of-concept, the recovery of cell type specific BRD4 and SP1 binding sites from cultured cells was demonstrated. Finally, Brd4 binding sites in the mouse cortex at single cell resolution were mapped, thus establishing a new technique for studying TF biology in situ.

Introduction

Transcription factors (TFs) regulate gene expression during the most critical junctures in the specification of cell fate. They are central to the maintenance of stem cell pluripotency and required for normal organogenesis during development. Overexpression of certain TFs can transdifferentiate one cell type into another, while abolishing TF binding sites can result in striking global phenotypes. Furthermore, the pattern of TF binding is often dysregulated during disease states. A better understanding of TF binding during tissue development and homeostasis would provide important insights into how cellular diversity arises and is maintained under normal and abnormal biological conditions.

In the past few years, single cell RNA-seq (scRNA-seq) techniques have emerged as the de facto methods for characterizing cellular diversity in complex tissues and organisms. More recently, multi-modal scRNA-seq technologies have been developed that combine transcriptional information with other genomic assays. These technologies are motivated by the realization that while scRNA-seq can describe the current state of a biological system, it alone cannot explain how that state arose. Thus, for a given population of cells, one can now simultaneously measure transcriptome and genome, or methylome, or chromatin accessibility, or cell-surface markers. These methods enable greater insight into the regulatory elements driving individual transcriptional programs.

A notable lacuna in the single cell repertoire is a method for simultaneously assaying transcriptome and TF binding. Such a method would allow for the genome-wide identification of TF binding sites across multiple cell types in complex tissues. ChIP-seq is the most popular technique for studying TF binding, and while single cell ChIP-seq has been previously described, this technique has only been employed to map highly abundant proteins such as methylated histones. DamID can recover TF binding sites by identifying nearby exogenously methylated adenines, but in single cells it has only been used to study laminin-associated domains. Importantly, both methods yield sparse data and neither technique simultaneously captures mRNA. Thus, each can only be used in a cell type specific manner if the cell type is known a priori and if sufficient numbers of cells are obtained by selection or sorting to overcome sparsity. In contrast, a single cell assay for transposase-accessible chromatin (scATAC-seq) can be used to identify nucleosome-free regions that may be bound by TFs across large numbers of mixed cells. However, it can only suggest potential DNA binding proteins by motif inference. It is therefore not a direct measurement of TF occupancy, and moreover it cannot be used to study transcriptional regulators that bind DNA indirectly or non-specifically, such as chromatin remodelers.

Transposon calling cards have been previously developed by the inventors as an alternative method to study TF binding. This system relies on two components: a fusion between a GAP, such as a TF and a transposase, and a transposon carrying a reporter gene. The fusion transposase deposits transposons near TF binding sites; these insertions are subsequently amplified from genomic DNA and subjected to high-throughput sequencing. Thus, the redirected transposase leaves "calling cards" at the genomic locations it has visited, which can then be identified later in time. The result is a genome-wide assay of all binding sites for that particular TF. In mammalian cells, piggyBac transposase fused to the TF SP1 has been heterologously expressed and the resulting pattern of insertions reflects SP1's DNA binding preferences. However, the method as described above was only feasible in bulk preparations.

Here is presented single cell calling cards (scCC), an extension of transposon calling cards that simultaneously profiles mRNA abundance and TF binding at single cell resolution. The key component of this work is a novel construct called the self-reporting transposon (SRT). Using SRTs, the genomic locations of inserted transposons can be mapped from either mRNA or DNA, but the use of mRNA enables both higher efficiency and compatibility with single-cell transcriptomics.

Here, it was established that TF-directed SRTs, in bulk, retain the ability to accurately identify TF binding sites. Next, it was demonstrated that the unfused piggyBac transposase, through its native affinity for the bromodomain TF BRD4, can be used to identify BRD4-bound super-enhancers (SEs). Also presented is the scCC method, which allows cell-specific mapping of SRTs from scRNA-seq libraries. This enables, in one experiment, concomitant assignment of cell types and identification of TF binding sites within those cells. In an experiment, scCC was used to map BRD4 and SP1 sites in mixtures of cultured human cells. This work concludes by identifying cell type-specific Brd4 binding sites in vivo in the postnatal mouse cortex. These results demonstrate that scCC can be a broadly applicable tool for the study of specific TF binding interactions across all cell types within a complex, multi-cellular tissue.

Results
Self-Reporting Transposons can be Mapped from mRNA Instead of Genomic DNA In order to combine scRNA-seq with calling cards, a transposon was developed whose genomic position could be determined from mRNA. A piggyBac self-reporting transposon (SRT) was created by removing the polyadenylation signal from the standard DNA-based calling card vector (see e.g., FIG. 5A). This enables RNA polymerase II (Pol II) to transcribe the reporter gene contained in the transposon and continue through the terminal repeat (TR) into the flanking genomic sequence. Thus, SRTs "self-report" their locations through the unique genomic sequence found within the 3' untranslated regions (UTRs) of these reporter gene transcripts. Although previously published gene- or enhancer-trap transposons could, in principle, also capture positional local information via RNA, they are resolution-limited to the nearest gene or enhancer, respectively. In contrast, the 3' UTRs of SRT-derived transcripts contain the transposon-genome junction in the mRNA sequence, so insertions can be mapped with base pair precision.

Figure 9A:
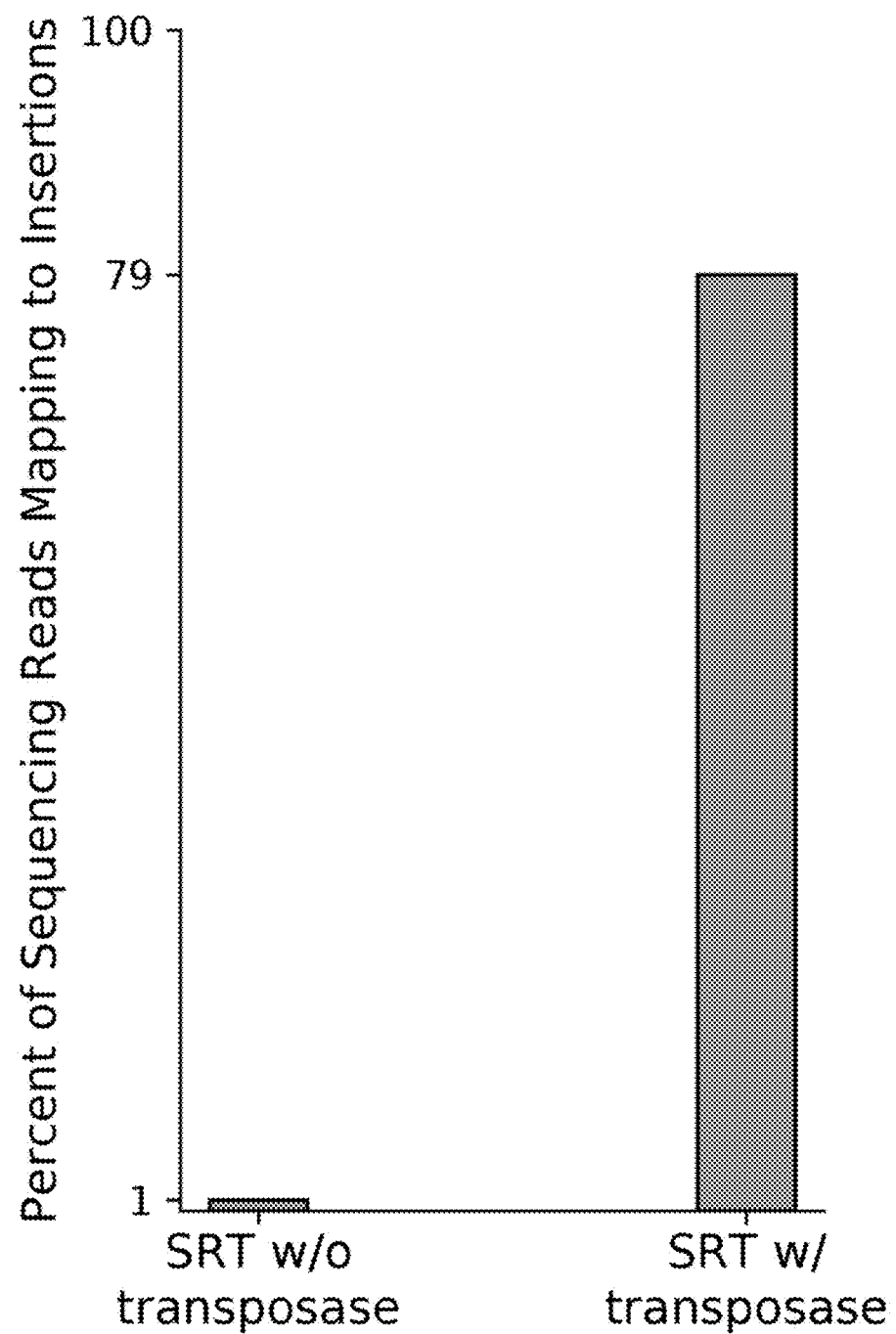
FIG. 9A-FIG. 9D is a series of schemes and graphs showing properties of self-reporting transposons. (A) Analysis of bulk RNA calling card libraries prepared from HEK293T cells transfected with PB-SRT-tdTomato with and without HyPBase transposase. The transposase is required for efficient and complex library generation. (B) Technical replication of bulk RNA calling cards from HCT-116 cells transfected with PB-SRT-Puro and SP1-PBase. Over 80% of insertions in each trial were shared between both replicates. (C) No significant differences were observed between DNA- and RNA-based recovery of SP1-directed insertions with respect to chromatin state in HCT-116 cells. (D) The self-cleaving ribozyme eliminates recovery of un-excised transposons when calling card libraries are prepared from RNA but not DNA.

SRTs are mapped following reverse transcription (RT) and PCR amplification of self-reporting transcripts. These transcripts contain stretches of adenines that are derived from either cryptic polyadenylation signals (PAS) or poly-adenine tracts encoded in genomic DNA downstream of the SRT insertion point (see e.g., FIG. 1B). A poly(T) RT primer hybridizes with these transcripts and introduces a universal priming site at one end of the transcripts. A pair of nested PCRs with an intermediate tagmentation step enable recovery of the transposon-genome junction. After adapter trimming and alignment, the 5' coordinates of these reads identify the genomic locations of insertions in the library. Libraries generated without transposase produce very few genomically mapped reads but the protocol is highly efficient when transposase is added (see e.g., FIG. 9A).

Figure 5A:
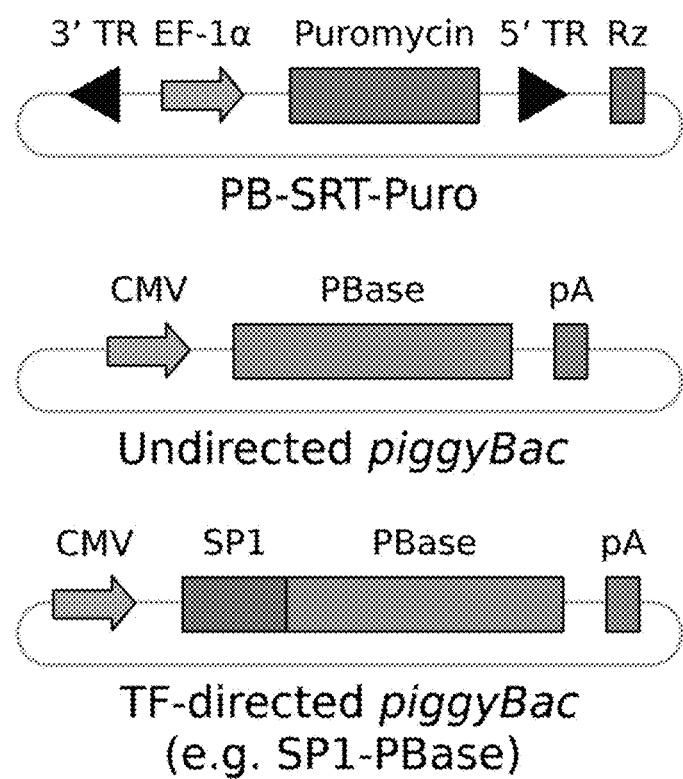
FIG. 5A-FIG. 5E is a series of schematics and graphs showing that self-reporting transposons (SRTs) are mapped more efficiently from RNA over DNA and, when directed SP1-PBase, identify SP1 binding sites. (A) Schematic of a self-reporting piggyBac transposon with puromycin marker (PB-SRT-Puro) and undirected (PBase) and SP1-directed (SP1-PBase) piggyBac transposases. SRTs are constructed by removing the polyadenylation signal sequence between the end of the marker gene and the 5' terminal repeat (TR). A self-cleaving ribozyme (Rz) on the delivery vector, downstream of the SRT, prevents recovery of plasmid transposons. (B) SRTs are mapped by reverse transcribing RNA with a poly(T) primer followed by a series of nested PCRs and tagmentation. This final library is enriched for the junction between the transposon and the genome. (C) RNA-based recovery of SP1-directed SRTs in HCT-116 cells is more efficient than DNA-based recovery. The RNA protocol recovers 80% of the same insertions as the DNA protocol and recovers twice as many insertions overall. (D) The distribution of insertions with respect gene annotation is identical between transposons recovered by DNA and by RNA. (E) Insertions deposited by SP1-PBase show pronounced and specific clustering at SP1 ChIP-seq peaks over insertions left by undirected PBase. In the calling card track, each circle represents an independent insertion. Genomic position is on the x-axis and the number of reads supporting that insertion is on the y-axis on a $\log_{10}$-transformed scale. The density tracks show the local density of insertions in each experiment, normalized for library size.
Figure 5B:
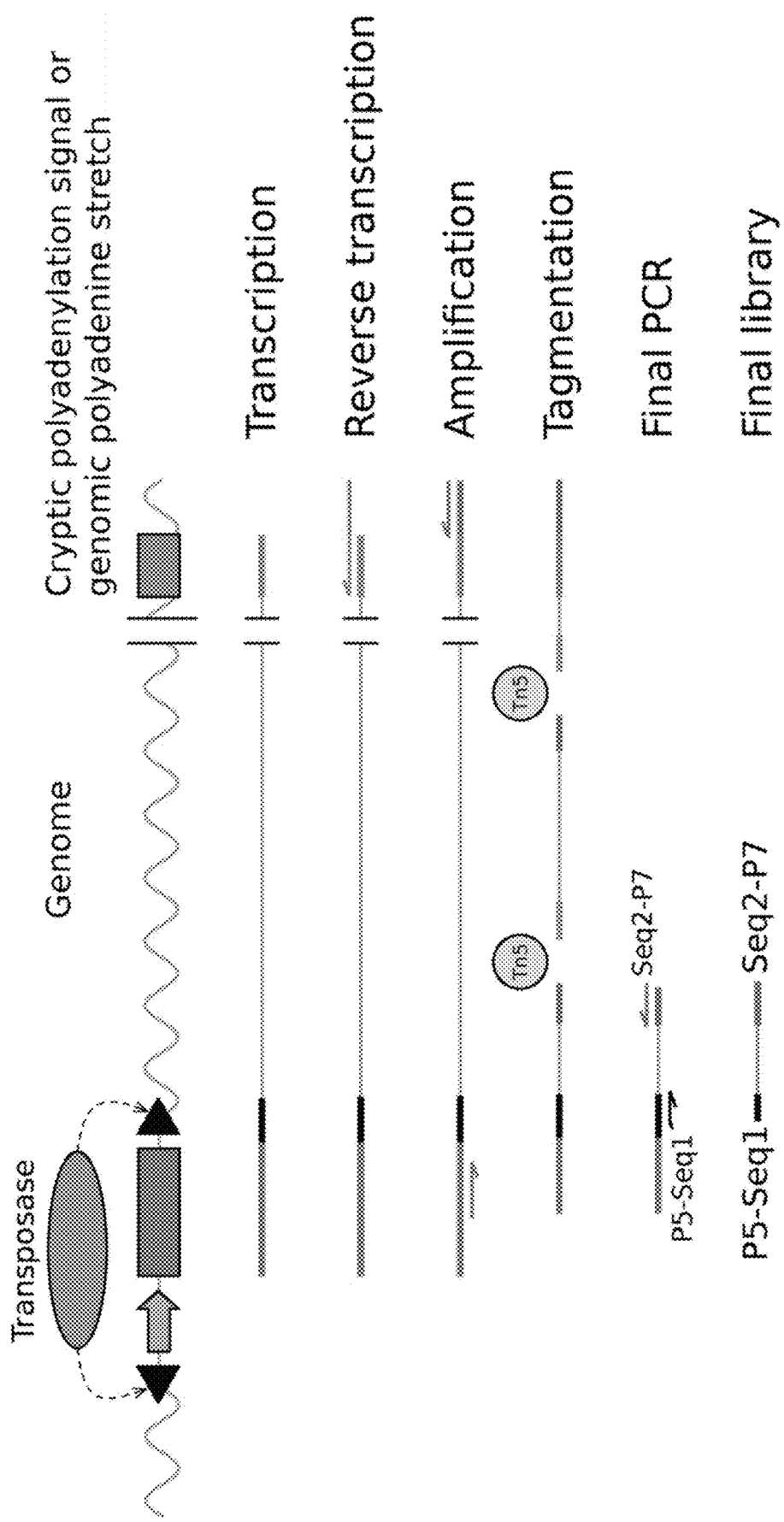
Figure 5C:
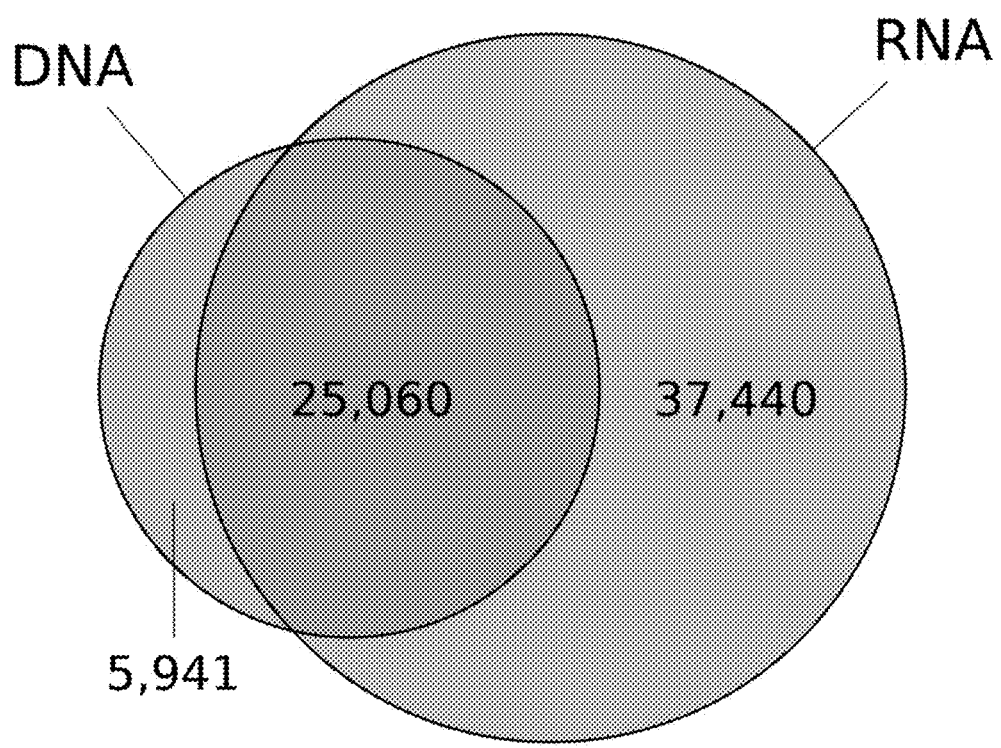
Figure 5D:
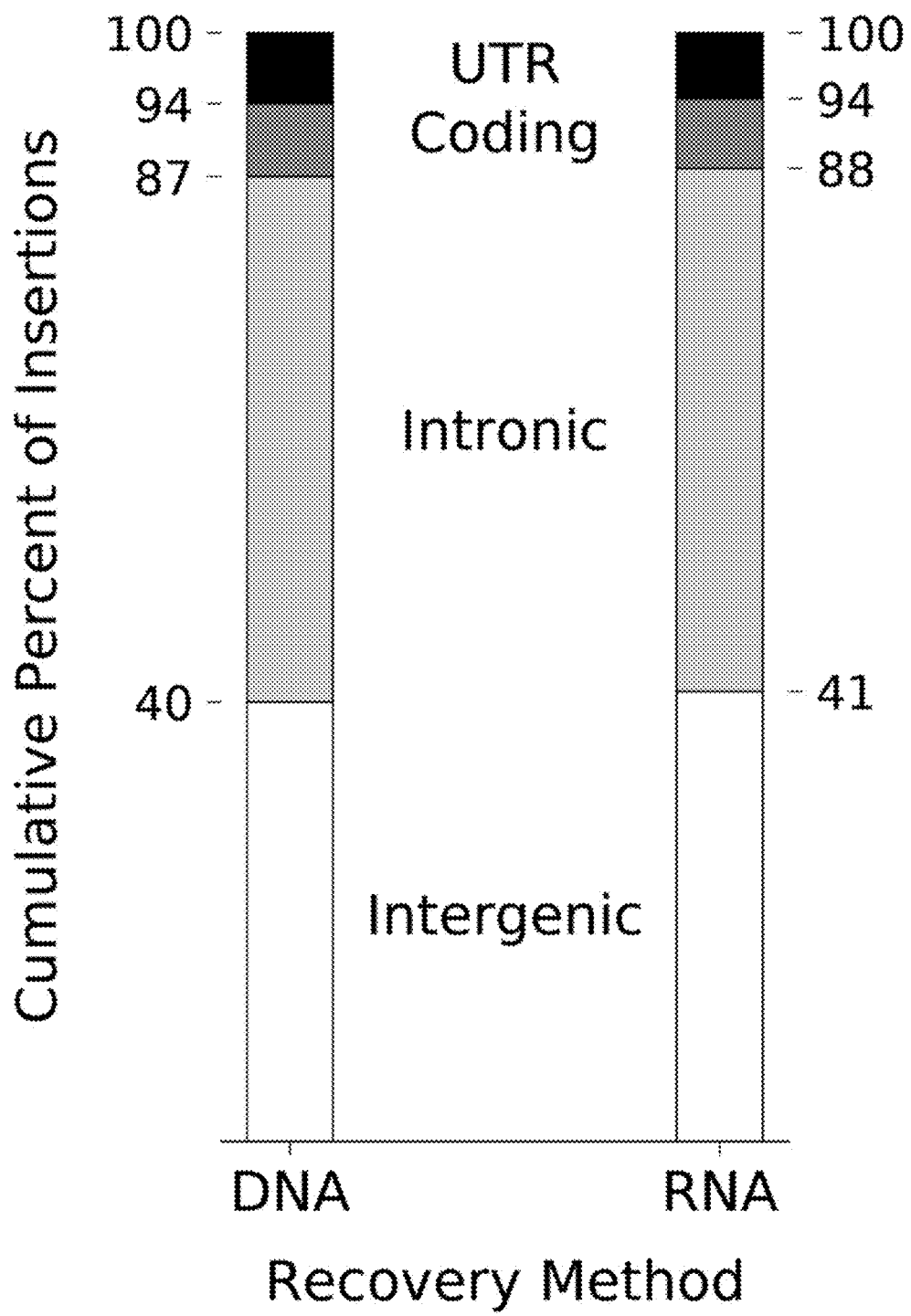
Figure 9B:
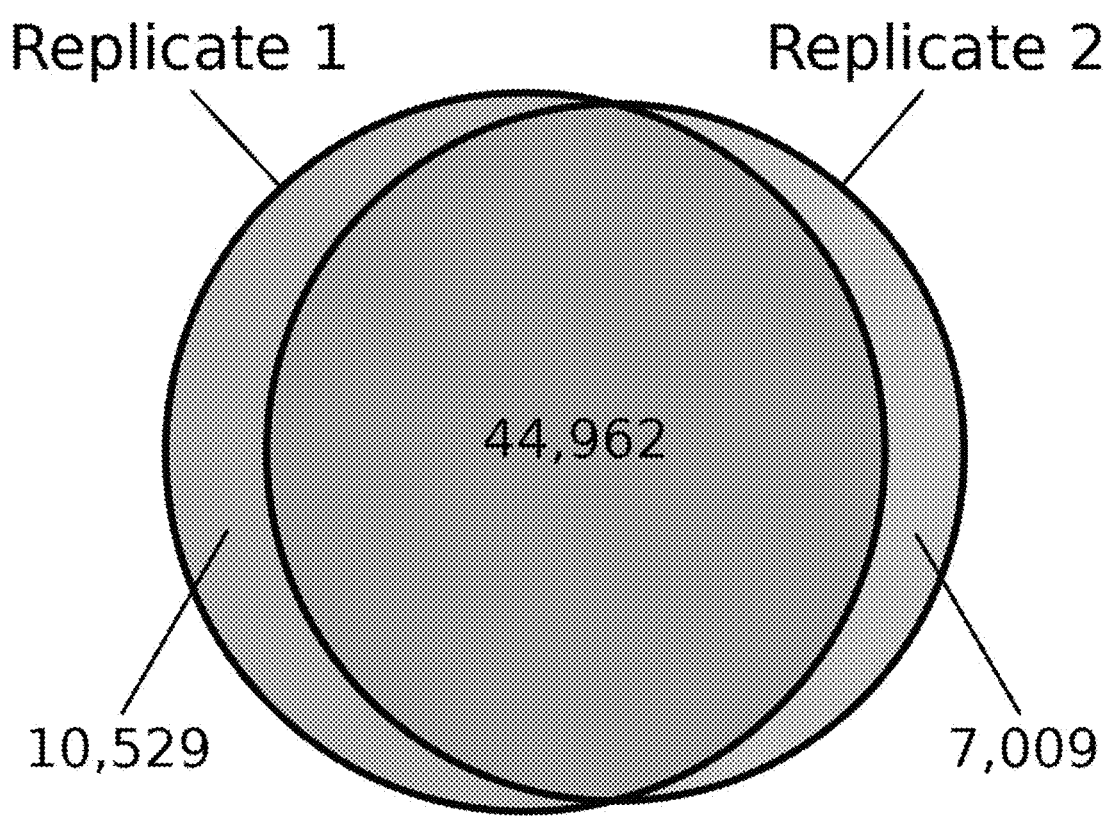
Figure 9C:
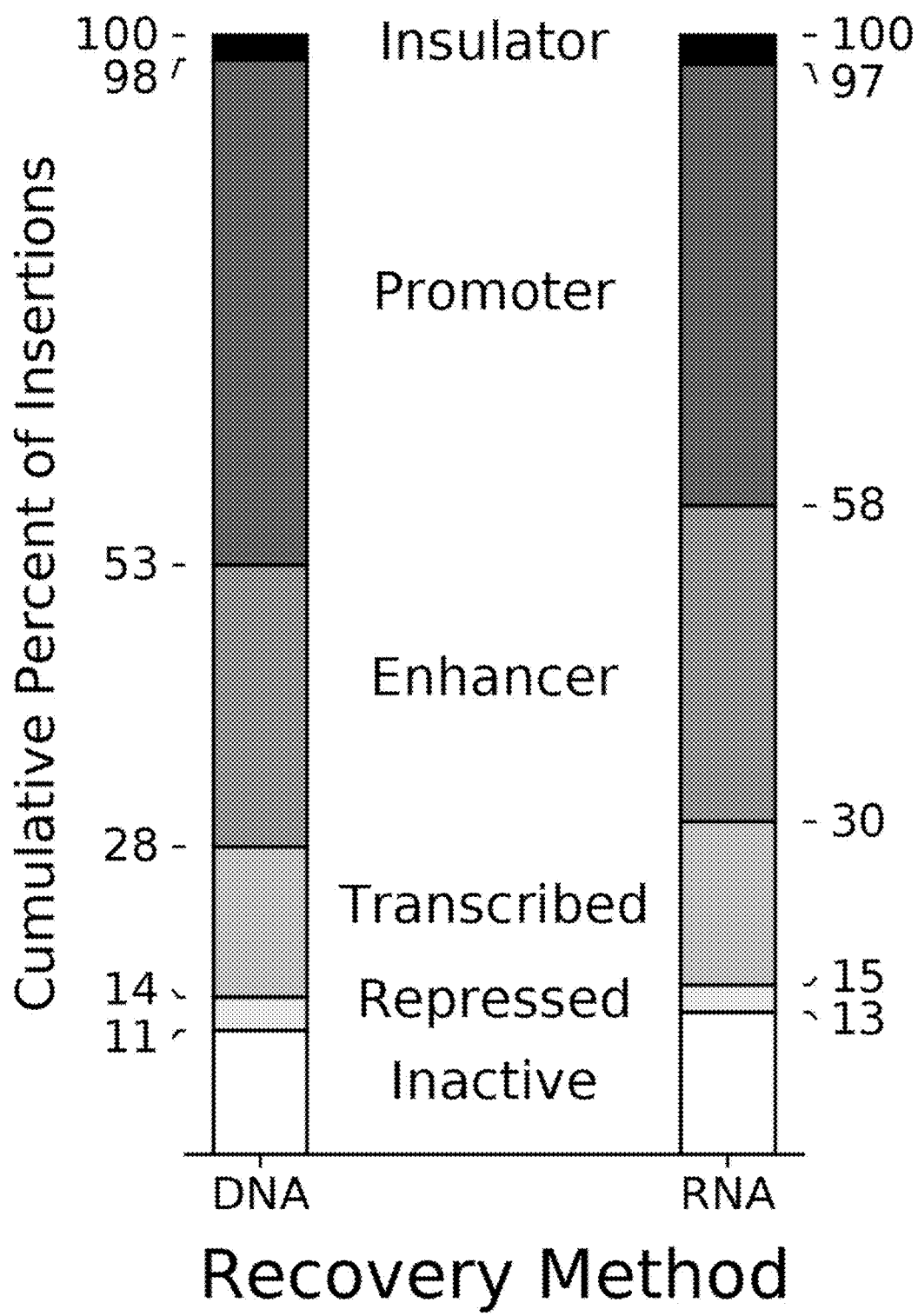
Figure 20:
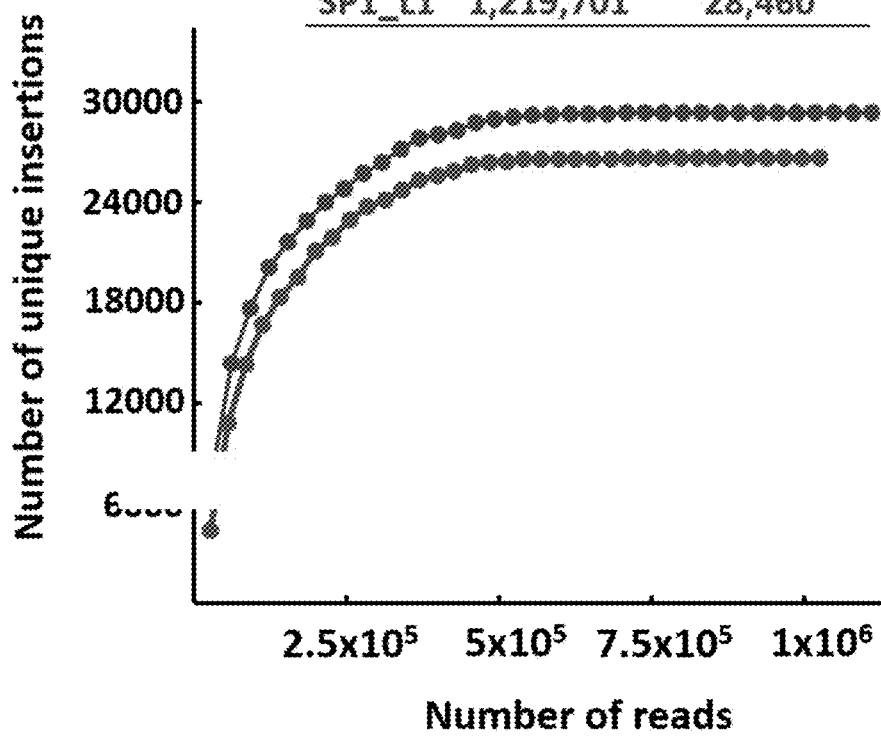
FIG. 20 (top panel) demonstrates that the we recovered as many insertions from the Sp1-retrotransposase fusion as with the unfused retrotransposase, demonstrating that the fusion does not significantly impair retrotransposase activity. (bottom panel) The Sp1-retrotranspose fusion deposits significantly more transposons into promoters, 5' UTRs and CpG islands, consistent with Sp1's known binding preferences for these regions of the genome. These data demonstrate that retrotransposon insertions are significantly enriched near Sp1 binding sites.
Figure 21:
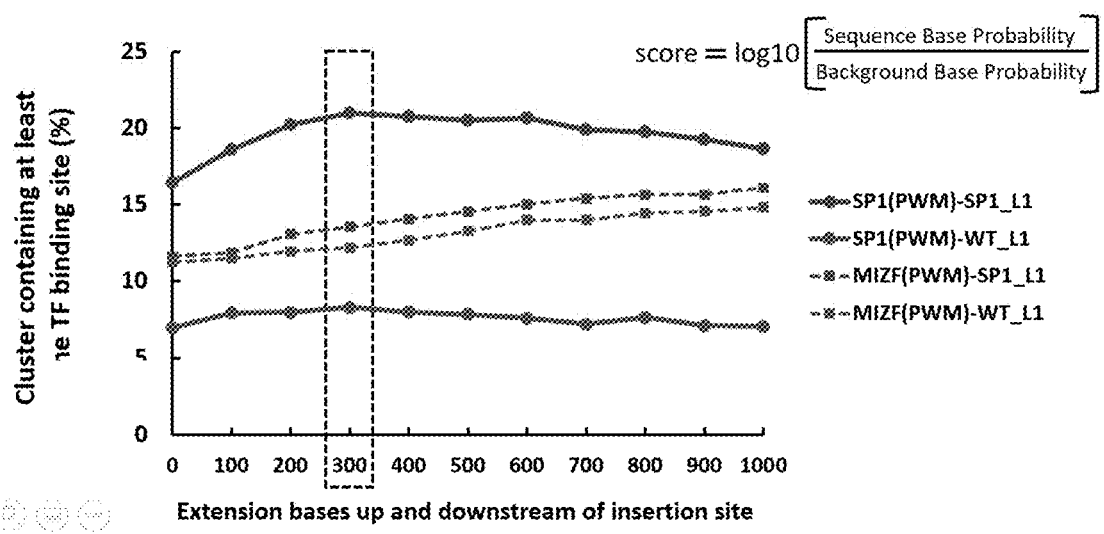
FIG. 21 is a table and graph demonstrating that the Sp1 transcription factor can redirect insertions of the L1 transposon, as Sp1 directed insertions are enriched near Sp1 motifs.

To compare transposon recovery between the new RNA-based protocol and the standard DNA-based inverse PCR protocol, HCT-116 cells were transfected with a plasmid carrying a piggyBac SRT (PB-SRT-Puro) and a plasmid encoding a fusion of the TF SP1 and piggyBac transposase (SP1-PBase; see e.g., FIG. 5A). After two weeks of selection, approximately 2,300 puromycin-resistant clones were obtained. These cells were split in half: one half underwent inverse PCR while the other half were processed with the new RNA workflow. With inverse PCR, 31,001 insertions were obtained (mean coverage: 709 reads per insertion), while the RNA-based protocol recovered 62,500 insertions (mean coverage: 240 reads per insertion). About 80% of insertions recovered by DNA calling cards were also recovered in the RNA-based library (25,060 insertions; see e.g., FIG. 5C), an overlap comparable to that between technical replicates of RNA recovery (see e.g., FIG. 9B). However, the RNA protocol recovered a further 37,440 insertions that were not found in the DNA-based library. To determine if these extra insertions were genuine, the distribution of insertions was analyzed by genetic annotation (see e.g., FIG. 5D) or chromatin state (see e.g., FIG. 9C and FIG. 20). Transposons mapped from either the DNA or the RNA libraries showed comparable distribution into annotated domains of particular functional or chromatin states, indicating that RNA recovery of transposons appears to be unbiased with respect to the presently described established, DNA-based protocol.

Figure 10A:
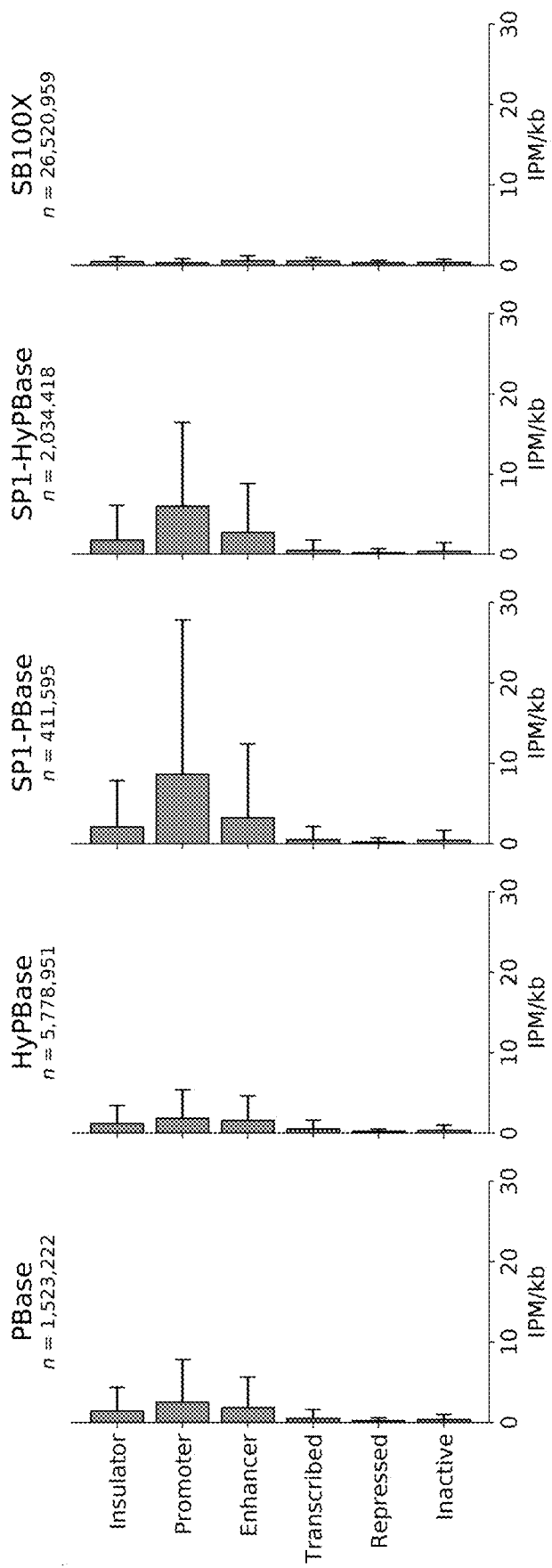
FIG. 10A-FIG. 10B is a series of graphs showing piggyBac, SP1-piggyBac fusions, and Sleeping Beauty display different local transposition rates depending on chromatin state. (A) Chromatin state analysis on local rates of transposition. Undirected and SP1-directed piggyBac transposases show different preferences for chromatin states. Undirected piggyBac favors promoters and enhancers, while SP1-piggyBac fusions show marked preference for promoters. Sleeping Beauty shows uniform distribution of insertions across all chromatin states. (B) Same data as (A) but with different x-axes for each graph. IPM: insertions per million mapped insertions; kb: kilobase.
Figure 10B:
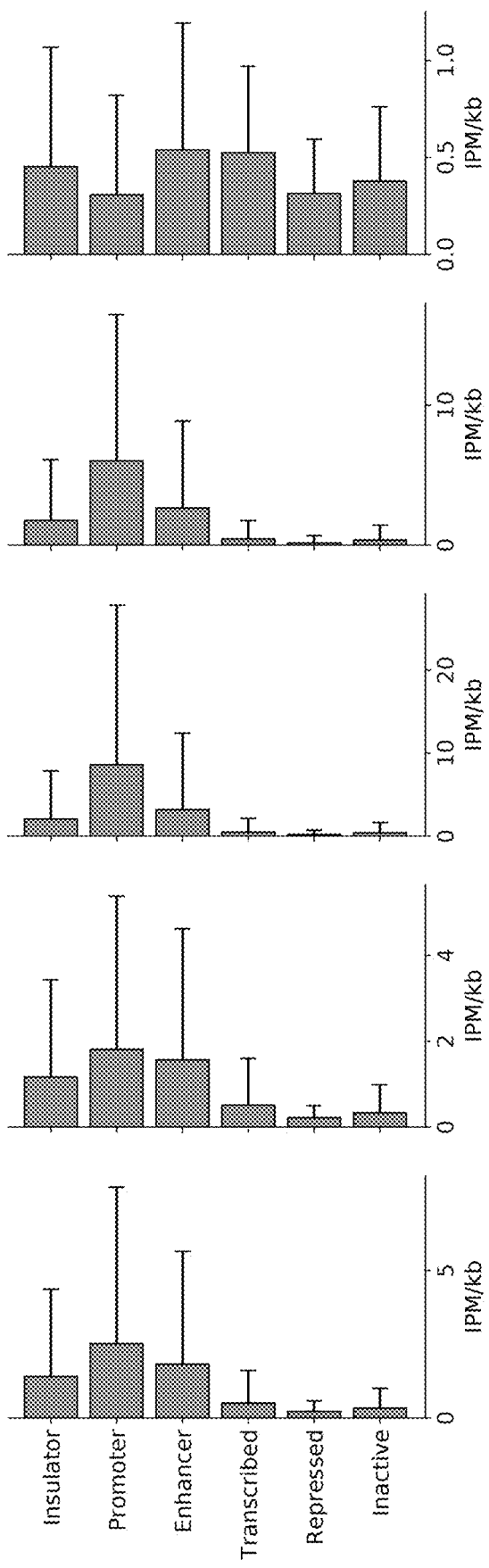

Because piggyBac is known to preferentially insert near active chromatin, SRT recovery may be biased towards euchromatic regions. Previous reports have shown that the Sleeping Beauty transposase has very little preference for chromatin state. A self-reporting Sleeping Beauty transposon was created and its genome-wide distribution compared to that of SRTs deposited by wild-type piggyBac (see e.g., FIG. 10A and FIG. 10B). Undirected piggyBac transposases appeared to modestly prefer transposing into promoter and enhancers, which is consistent with previous reports (see e.g., FIG. 20). By contrast, Sleeping Beauty showed largely uniform rates of insertions across all chromatin states, including repressed and inactive chromatin (see e.g., FIG. 10B). These results affirm that while RNA-based recovery is more efficient, it still preserves the underlying genomic distributions of insertions. Furthermore, because SRTs can be recovered from virtually any chromatin state, RNA-based calling card recovery can be employed to analyze a variety of TFs with broad chromatin-binding preferences.

Figure 9D:
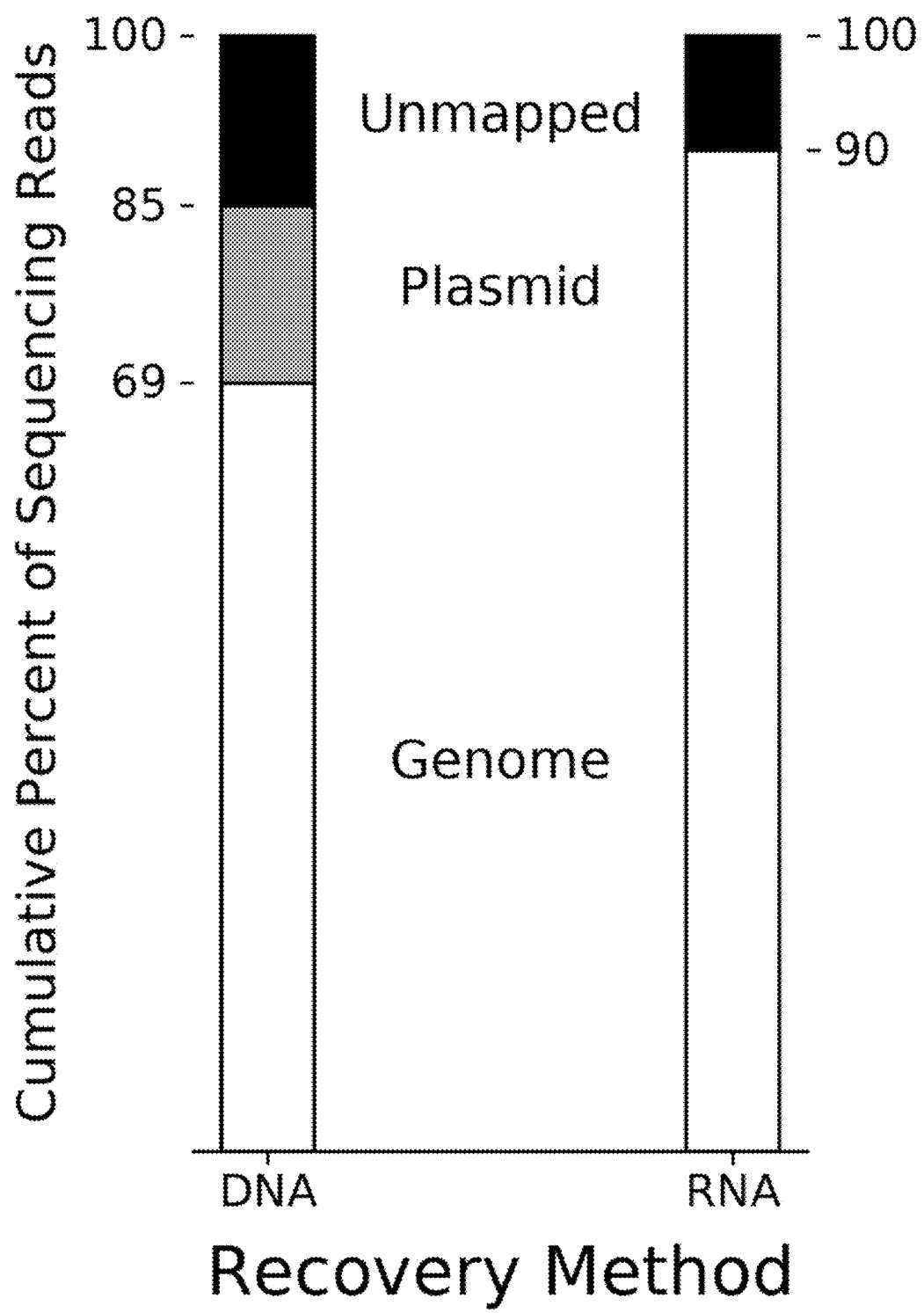

A common artifact observed in DNA-based transposon recovery is a large fraction of reads mapping back to the donor transposon plasmid instead of the genome. Although this can be mitigated by long selection times or by digestion with the methyladenine-sensitive enzyme DpnI, these methods do not completely eliminate background and are not compatible with all experimental paradigms, in particular viral transduction. To reduce this artifact, a hammerhead ribozyme was included in the SRT plasmid downstream of the 5' TR. Before transposition, the ribozyme will cleave the nascent transcript originating from the marker gene, thus preventing RT. Transposition allows the SRT to escape the downstream ribozyme, leading to recovery of the self-reporting transcript. In a comparison of DNA- and RNA-based recovery, about 15% of reads from the SP1-PBase DNA library aligned to the plasmid, compared to fewer than 1% of reads from the RNA library (see e.g., FIG. 9D). Thus, the inclusion of a self-cleaving ribozyme virtually eliminates recovery of un-excised transposons.

SP1 Fused to piggyBac Directs SRT Insertions to SP1 Binding Sites

Next, it was confirmed that RNA calling cards, in bulk, can still be used to identify TF binding sites. 10-12 replicates of HCT-116 cells were transfected with plasmids containing the PB-SRT-Puro donor transposon and SP1 fused to either piggyBac (SP1-PBase) or a hyperactive variant of piggyBac (SP1-HyPBase). As controls, a similar number of replicates was also transfected with undirected PBase or HyPBase, respectively. 411,287 insertions from SP1-PBase and 1,523, 169 insertions from PBase were obtained. Similarly, 2,033, 229 SP1-HyPBase insertions and 5,779,101 insertions from HyPBase were obtained.

Figure 5E:
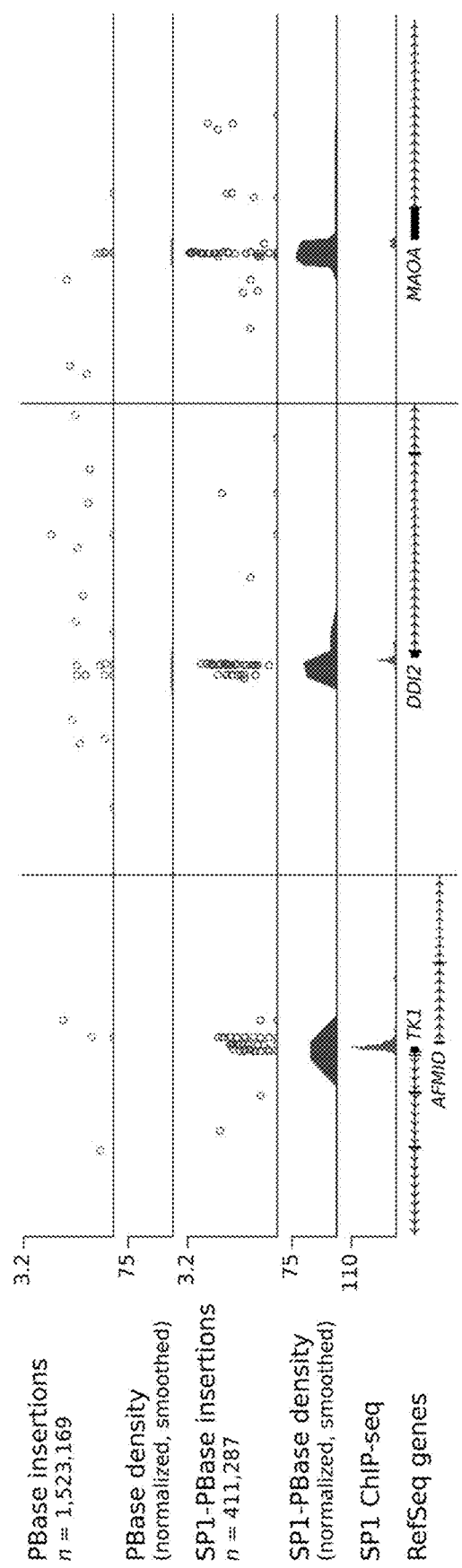
Figure 11A:
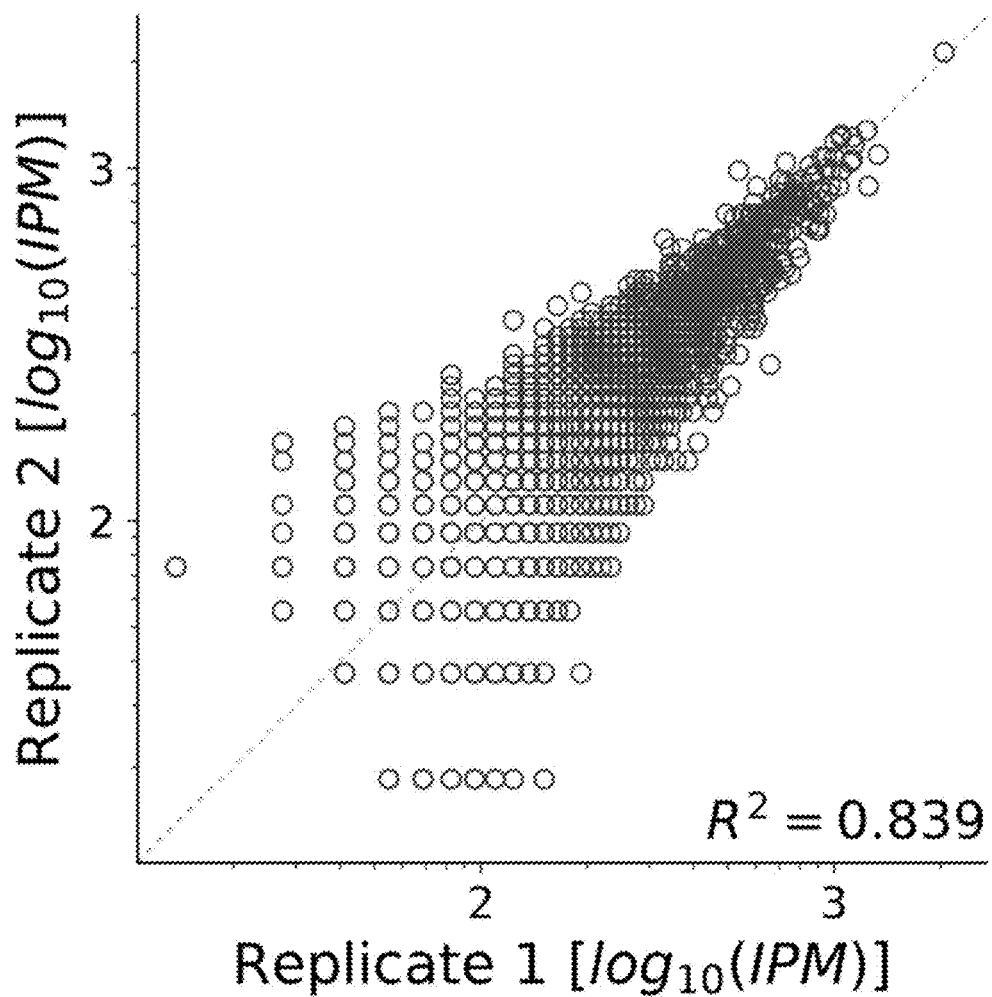
FIG. 11A-FIG. 11E is a series of graphs showing SP1 fused to piggyBac redirects insertions to SP1 binding sites. (A) SP1 peaks show high reproducibility between biological replicates. Each circle represents a peak; x and y coordinates represent normalized insertions in each biological replicate. (B) Mean SP1 ChIIP-seq profile across all SP1 peaks shows strong central enrichment. (C) Heatmap of SP1 ChIP-seq signal across all SP1 peaks, expressed as $\log_2$ (FC) over the input control. (D) SP1-PBase shows enrichment of insertions to transcription start sites (TSSs), CpG islands, and unmethylated CpGs, all known biological targets of SP1. Each enrichment was statistically significant at $p<10^{-9}$ (G test of independence). (E) Motif discovery performed on SP1 peaks shows good concordance with an orthogonally-derived SP1 motif. IPM: insertions per million mapped insertions. FC: fold change.
Figure 11B:
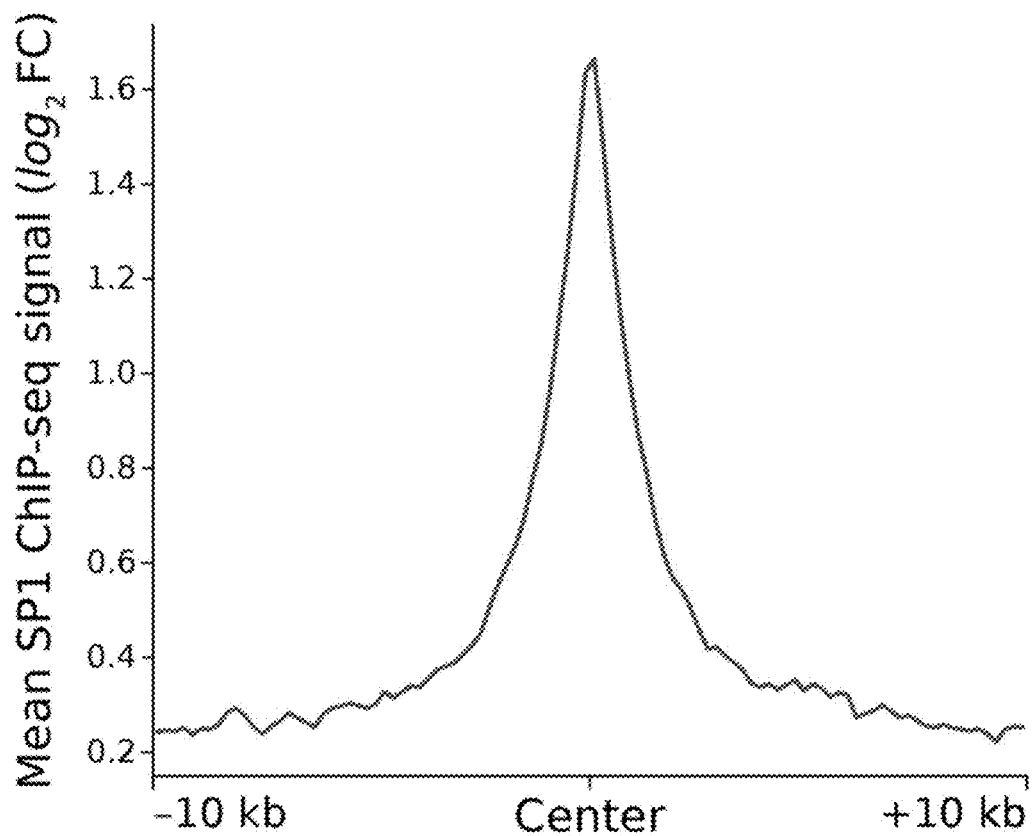
Figure 11C:
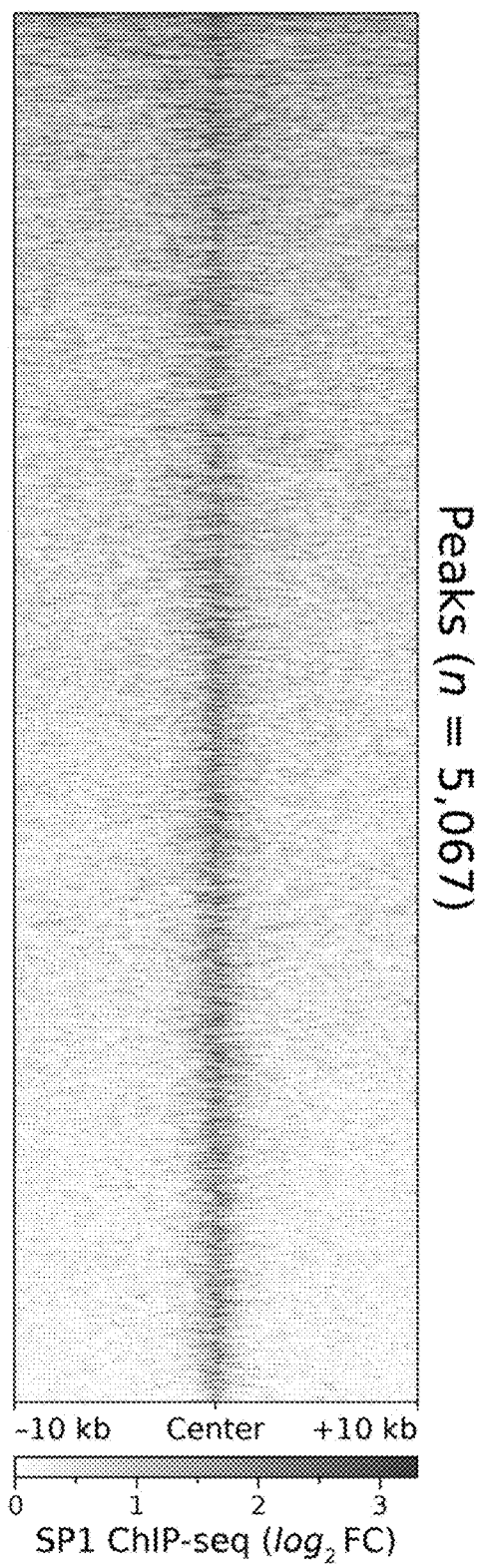
Figure 11D:
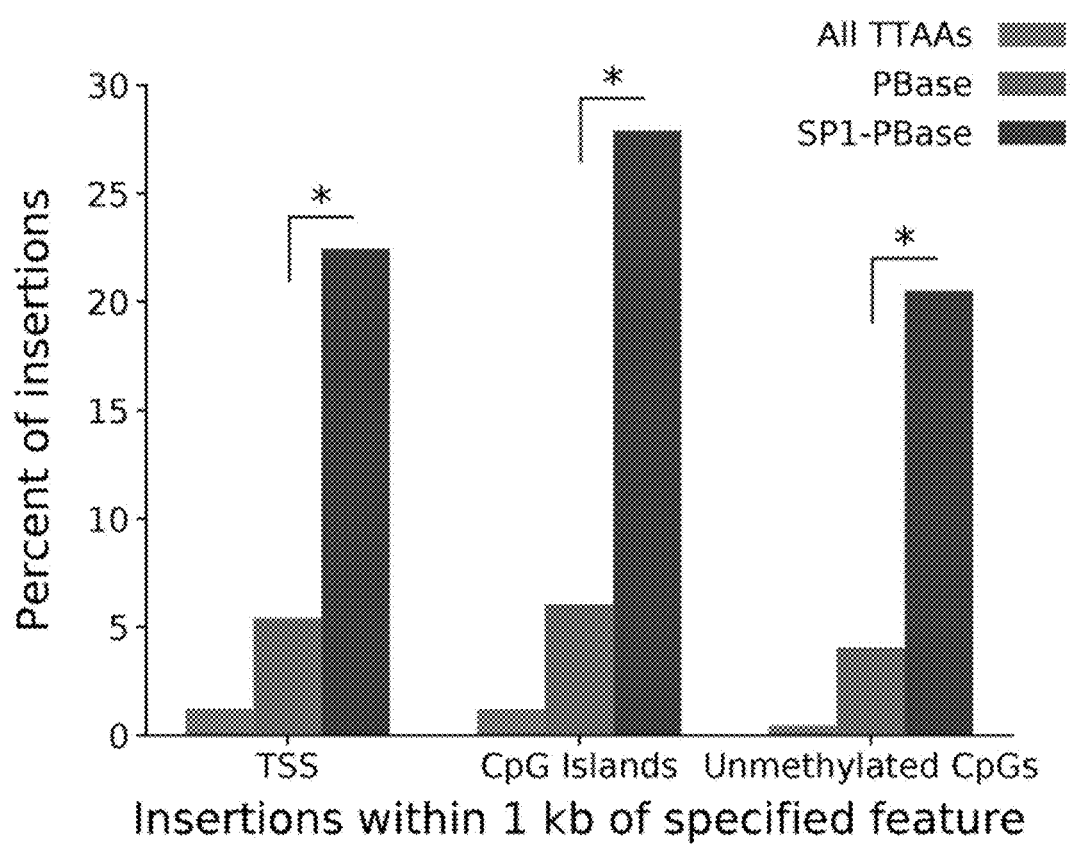
Figure 11E:
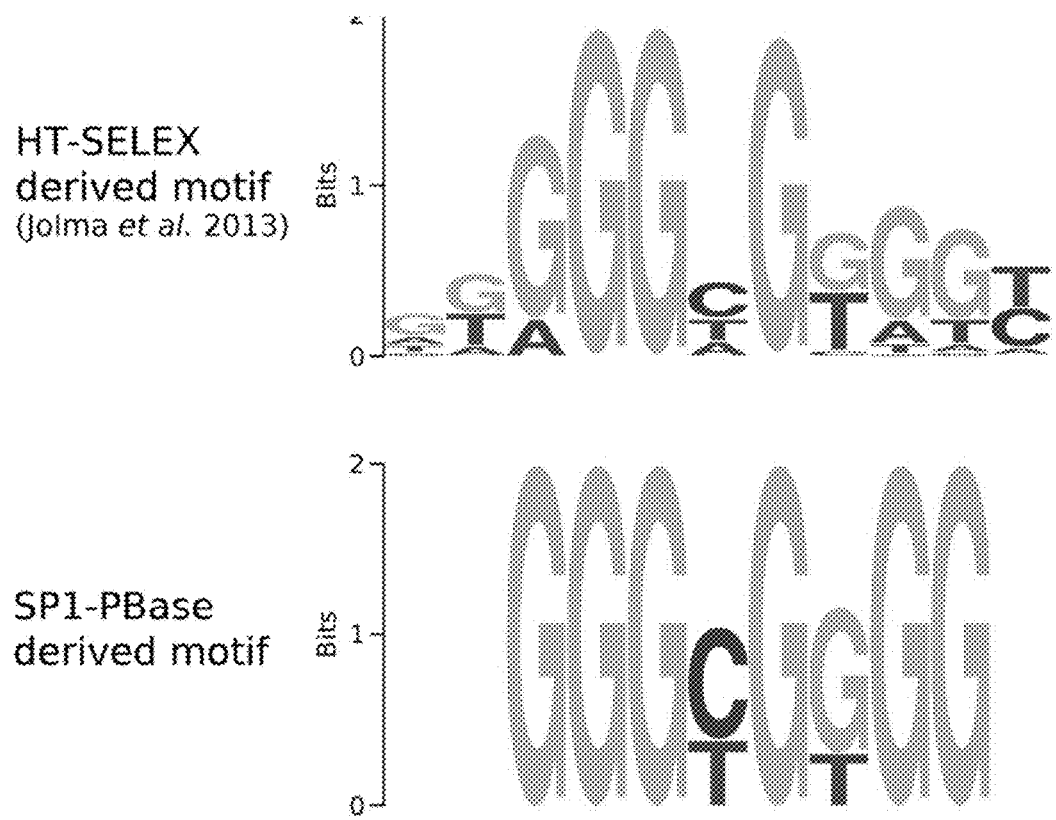
Figure 12B:
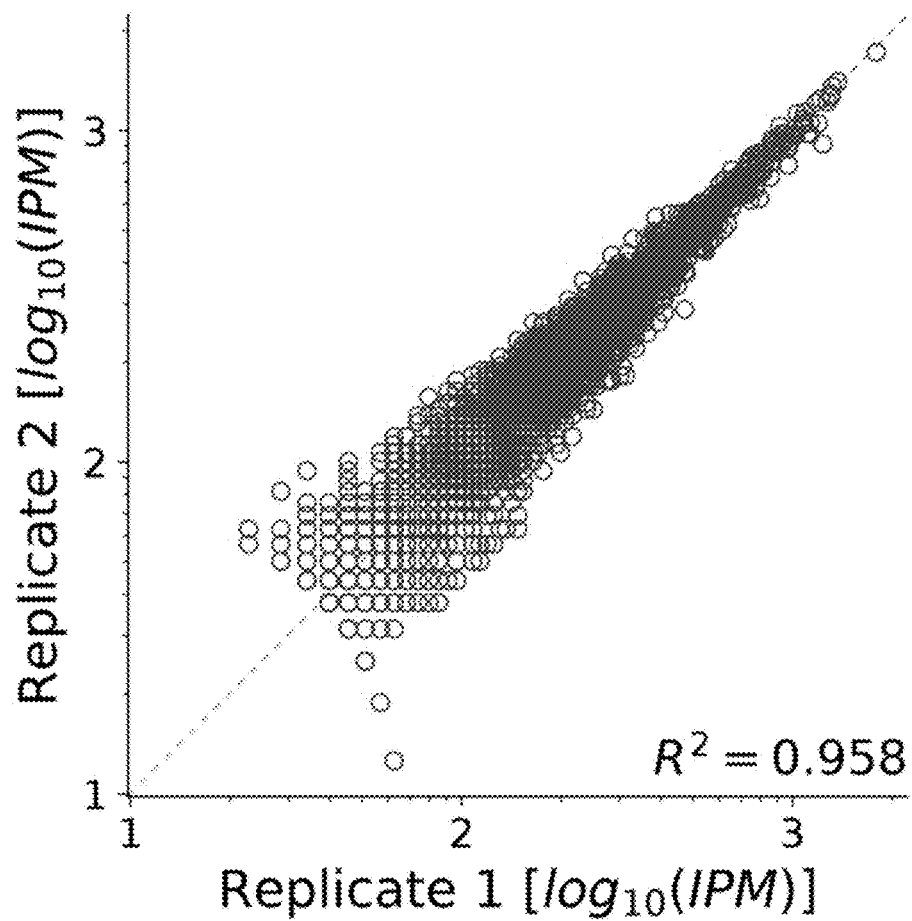
Figure 12C:
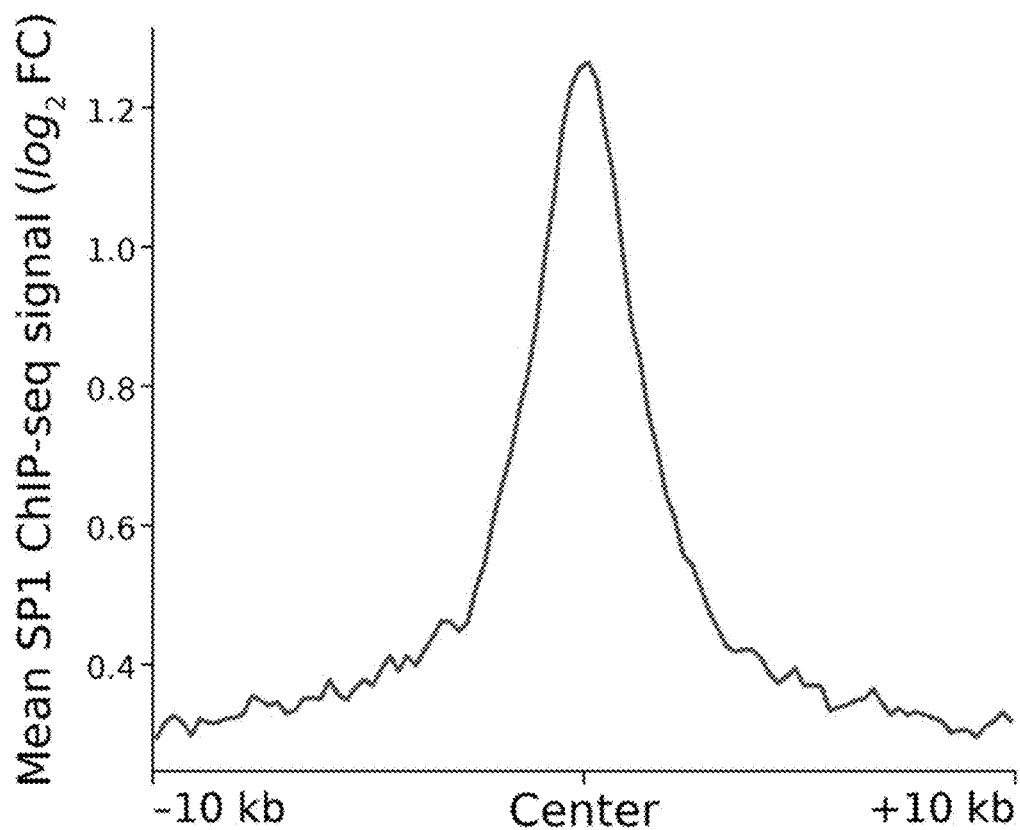
Figure 12D:
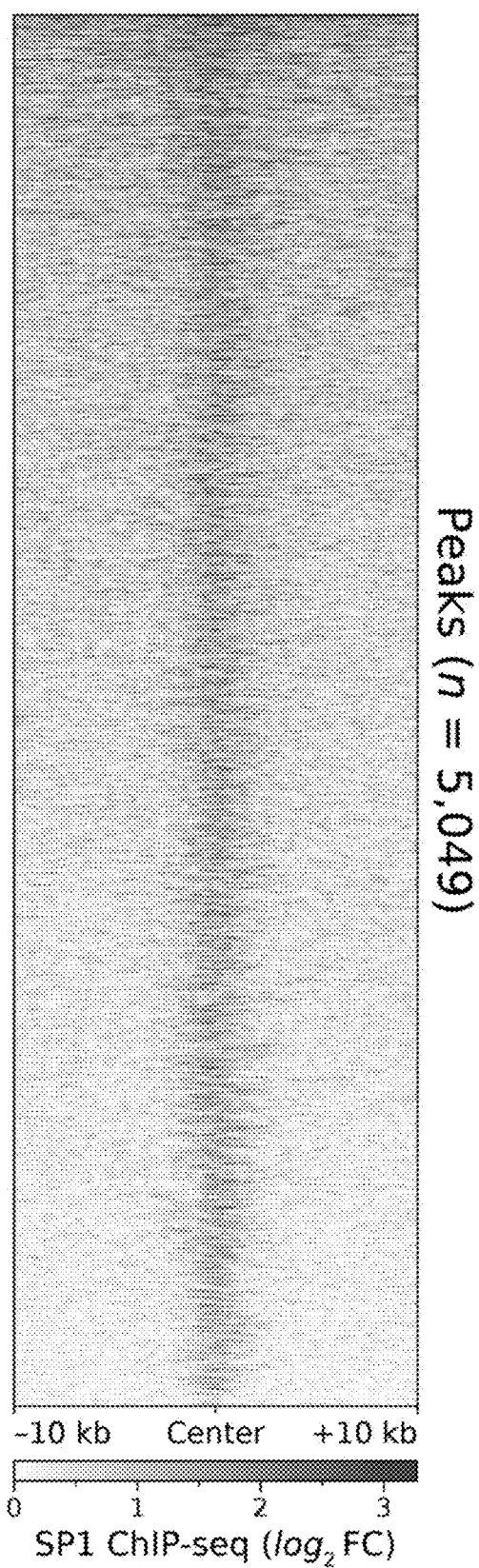
Figure 12E:
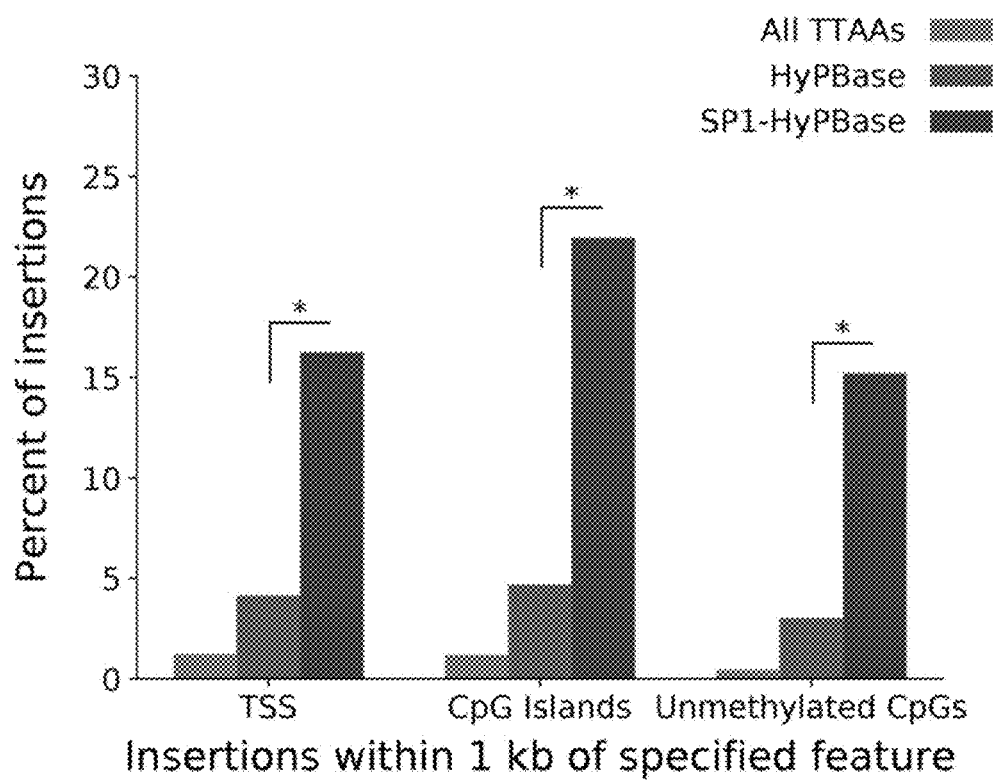

FIG. 5E and FIG. 12A show the redirection of SRT calling cards by SP1-PBase and SP1-HyPBase, respectively, to three representative SP1-bound regions of the genome. Each circle in the insertions track represents an individual transposition event whose genomic position is on the x-axis. The y-axis is the number of reads supporting each insertion on a $\log_{10}$ scale. To better compare transposition rates across libraries with different numbers of insertions, the normalized local insertion rate was calculated and plotted as a density track. All three of the loci depicted in FIG. 5E and FIG. 12A show a specific enrichment of calling card insertions in the SP1 fusion experiments that is not observed in the undirected control libraries. Next, peaks were called at all genomic regions enriched for SP1-directed transposition. The number of insertions observed at significant peaks for both SP1-PBase and SP1—HyPBase was highly reproducible between biological replicates ($R^2$=0.84 and 0.96, respectively; see e.g., FIG. 11A and FIG. 12B). Furthermore, calling card peaks were highly enriched for SP1 ChIP-seq signal at their centers, both on average (see e.g., FIG. 11B and FIG. 12C) and in aggregate (see e.g., FIG. 11C and FIG. 12D). SP1 is known to preferentially bind near TSSs and is also thought to play a role in demethylating CpG islands. Therefore, it was confirmed that the SP1-directed transposases preferentially inserted SRT calling cards near TSSs, CpG islands, and unmethylated CpGs at statistically significant frequencies ($p<10^{-9}$ in each instance, G test of independence; see e.g., FIG. 12D and FIG. 12E). Moreover, compared to undirected piggyBac, SP1-directed piggyBac showed a striking preference for depositing insertions into promoters (see e.g., FIG. 10A and FIG. 10B). Lastly, regions targeted by SP1-PBase and SP1-HyPBase were enriched for the canonical SP1 DNA binding motif (p<10-70 in each instance; see e.g., FIG. 11E and FIG. 12F). Taken together, these results indicate that SP1 can redirect piggyBac SRTs near SP1 binding sites.

Clustering of Undirected piggyBac Insertions Identifies BRD4-Bound Super-Enhancers Previous studies have shown that the undirected piggyBac transposase preferentially inserts transposons near super-enhancers (SEs), a unique regulatory element that is thought to play a critical role in regulating cell identity. SEs are often enriched for the histone modification H3K27ac as well as RNA polymerase II and general transcription factors like the mediator element MED1 and the bromodomain protein BRD4. Moreover, the piggyBac transposase has a strong biophysical affinity for BRD4, as these proteins can be co-immunoprecipitated. Given the millions of insertions assayed from the undirected PBase and HyPBase controls in the SP1-directed experiments (see e.g., FIG. 5E and FIG. 12A), it may be possible to identify BRD4-bound SEs simply from the localization of undirected piggyBac transpositions.

Figure 6A:
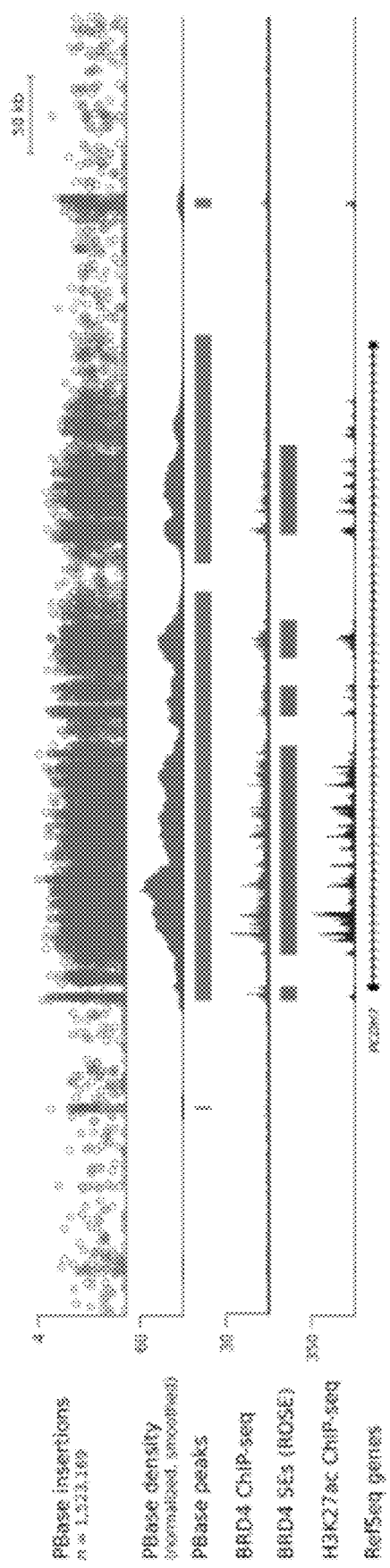
FIG. 6A-FIG. 6F is a series of graphs, scatter plots, and a heat map showing undirected piggyBac (PBase) insertions mark BRD4-bound super-enhancers. (A) Undirected PBase insertions are distributed non-randomly, with increased density overlapping BRD4-bound chromatin and H3K27 acetylated histones. Also shown are BRD4-bound super-enhancers (SEs). (B) PBase peak calls are highly replicable, with biological replicates showing high concordance of normalized insertions at peaks. (C) PBase peaks show central enrichment for BRD4 ChIP-seq signal. These findings are statistically significant when compared to a genome-wide permutation of PBase peaks ($p<10^{-9}$, KS test). (D) PBase peaks are centrally enriched for the histone modifications H3K27ac and H3K4me1, marks associated with enhancers. These same peaks show mild depletion for H3K9me and H3K27me, marks canonically associated with repressed chromatin. (E) Receiver-operator characteristic curve for SE detection using PBase insertions. (F) Precision-recall curve for SE detection using PBase insertions. IPM: insertions per million mapped insertions; AUROC: area under receiver-operator curve; AUPRC: area under precision-recall curve; KS: Kolmogorov-Smirnov; FC: fold change.
Figure 6B:
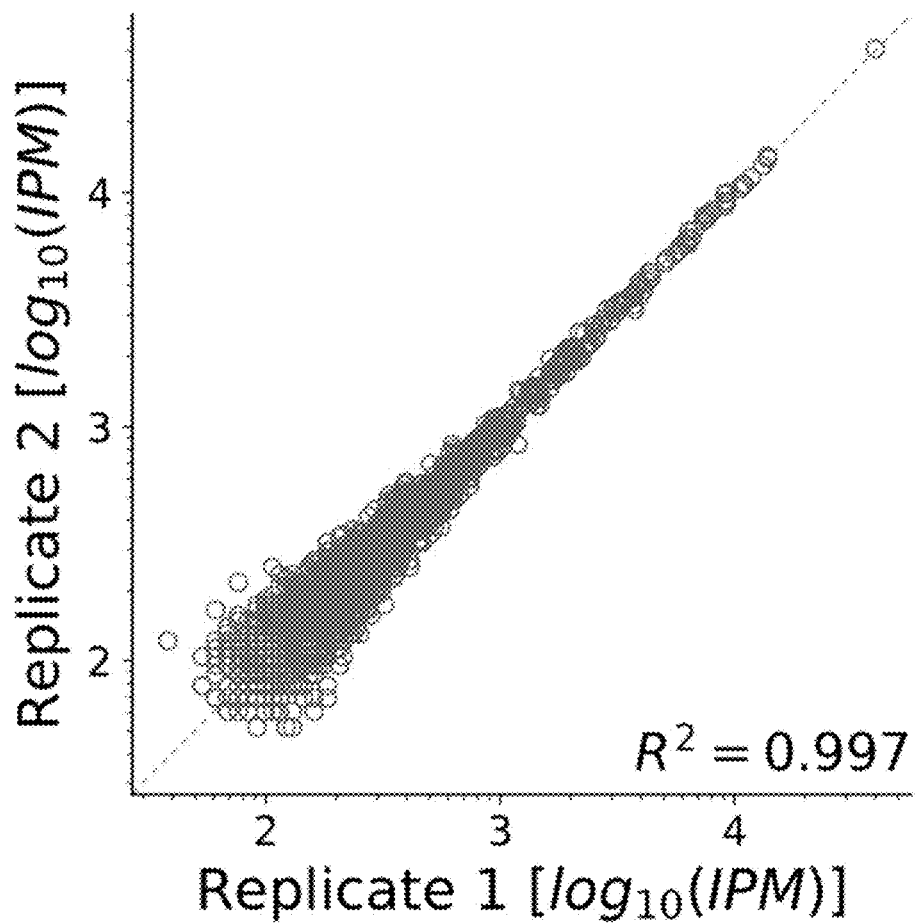
Figure 6C:
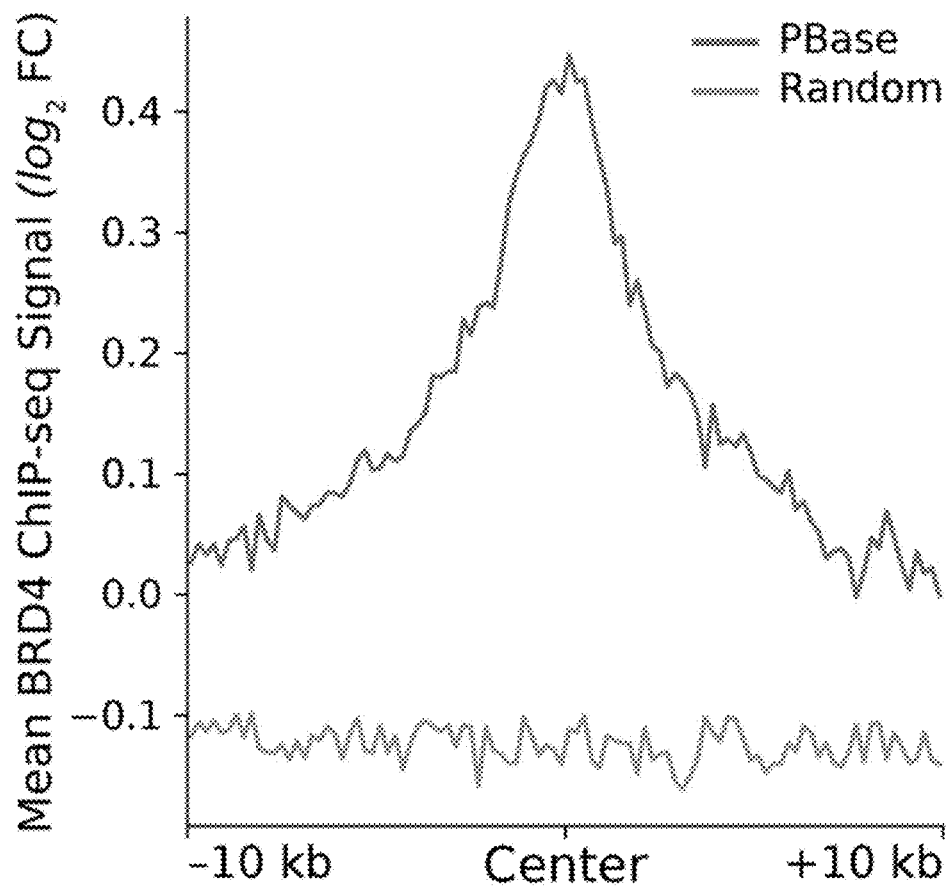
Figure 6D:
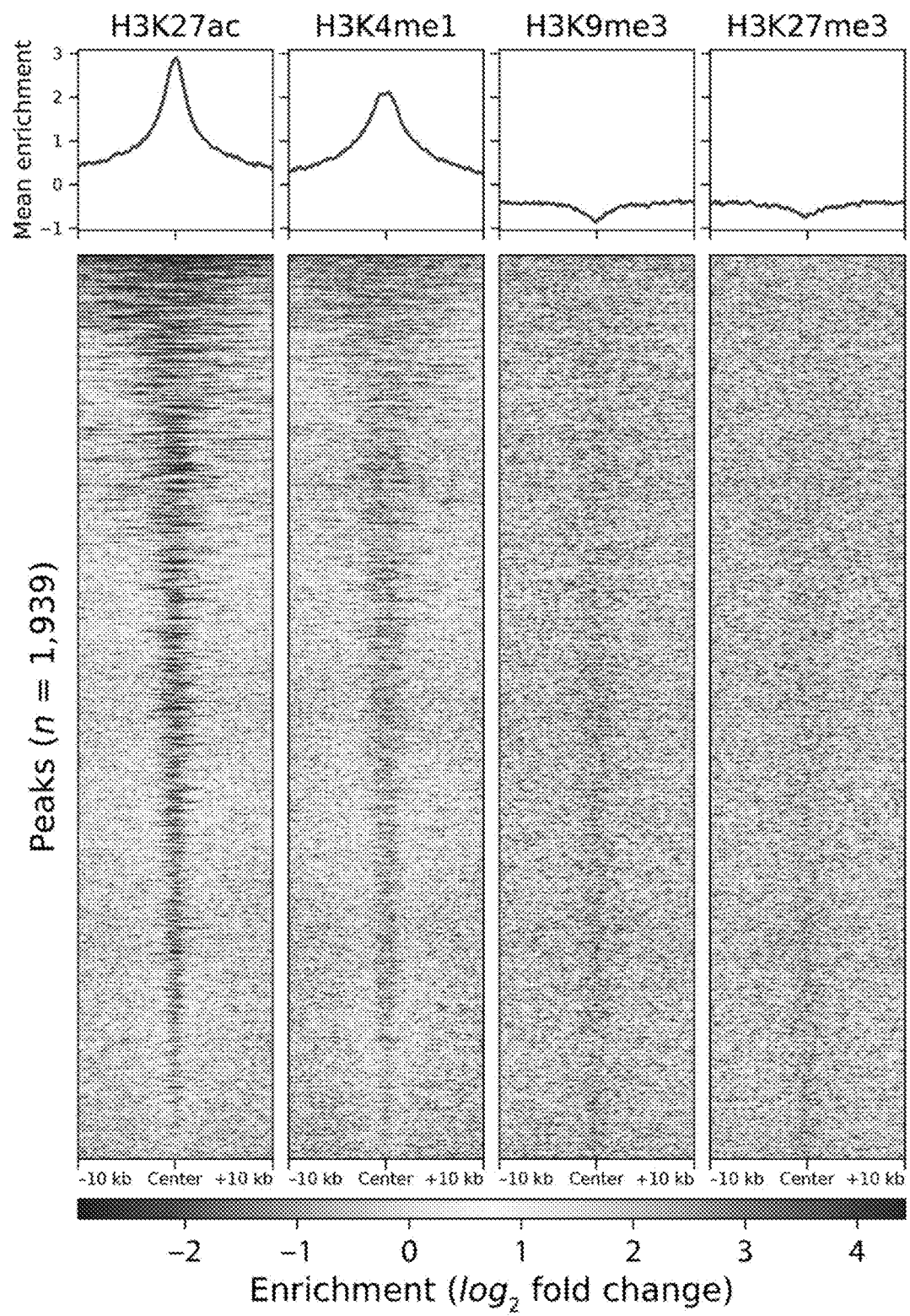
Figure 13A:
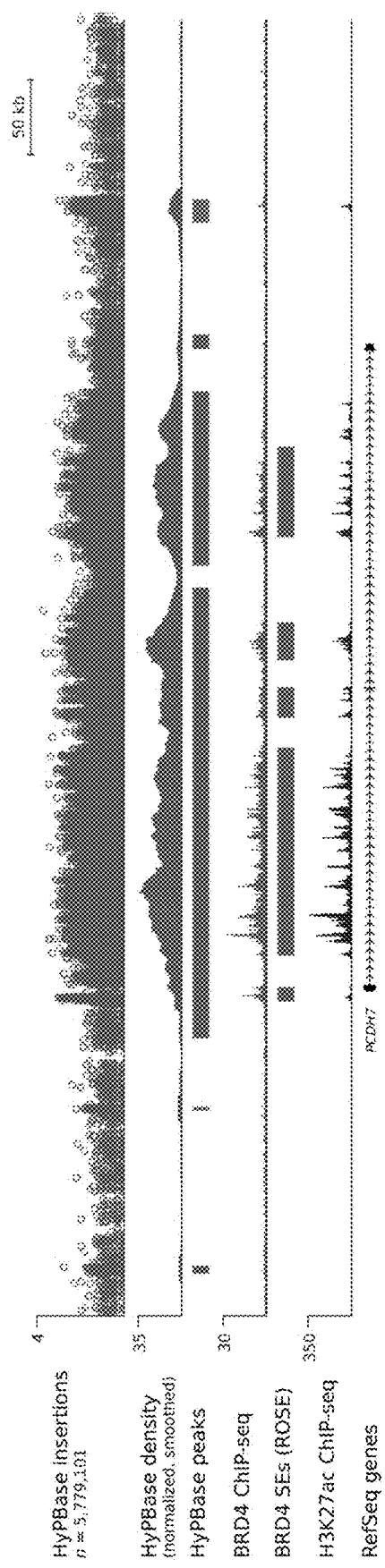
FIG. 13A-FIG. 13F is a series of graphs showing undirected hyperactive piggyBac (HyPBase) insertions also mark Brd4-bound super-enhancers. (A) Undirected HyPBase, like PBase, shows non-uniform densities of insertions in BRD4-bound regions. (B) Densities of insertions are reproducible at HyPBase peaks. (C) Mean BRD4 ChIP-seq profile at HyPBase peaks compared to randomly chosen peaks. The BRD4 enrichment is significant with $p<10^{-9}$ (KS test). (D) Undirected HyPBase peaks are strongly correlated with H3K27ac and H3K4me1 and mildly anti-correlated with H3K9me and H3K27me3, consistent with these regions being enhancers. (E) Receiver-operator characteristic curve for detecting BRD4-bound SEs with undirected HyPBase peaks. (F) Precision-recall curve for detecting SEs with undirected HyPBase peaks. KS: Kolmogorov-Smirnov; FC: fold change.
Figure 13B:
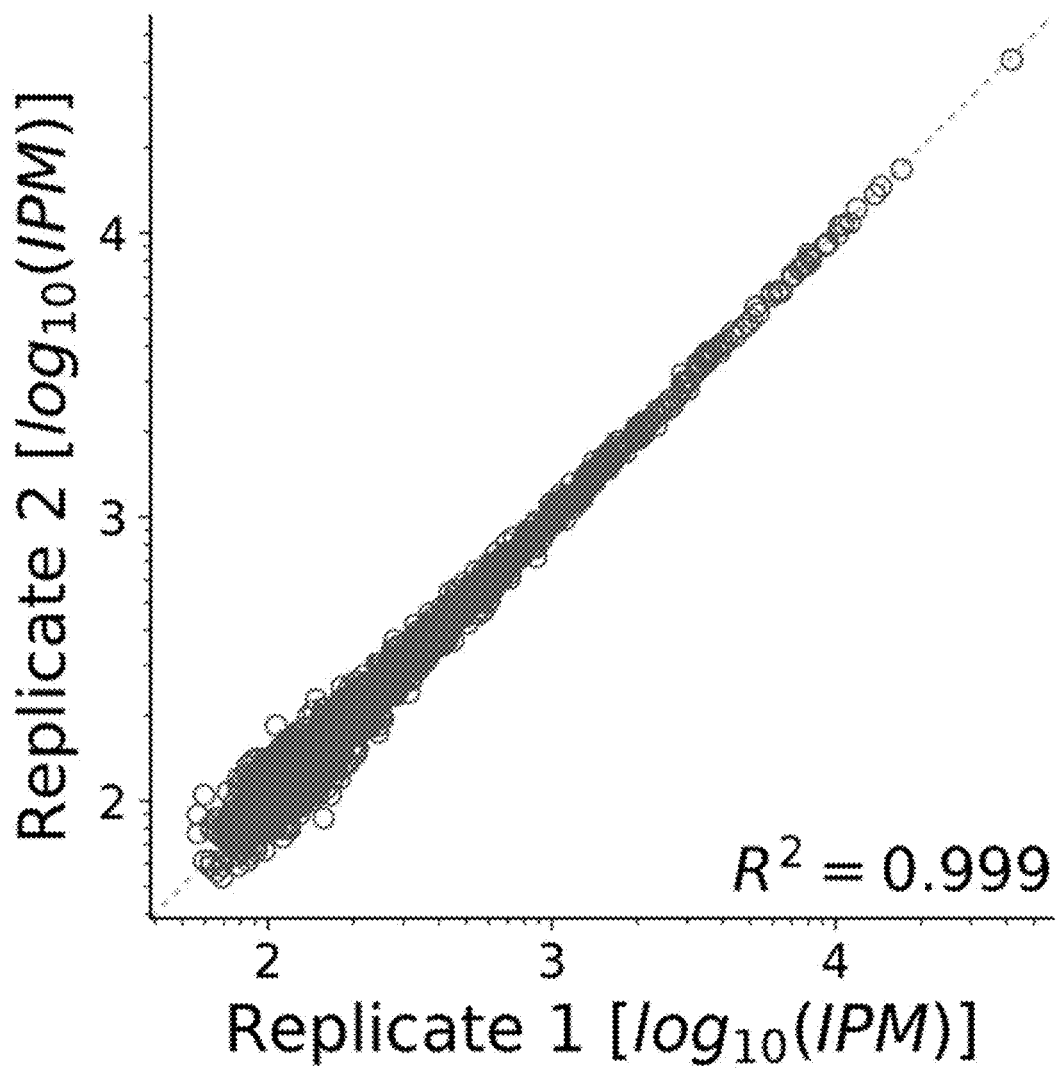
Figure 13C:
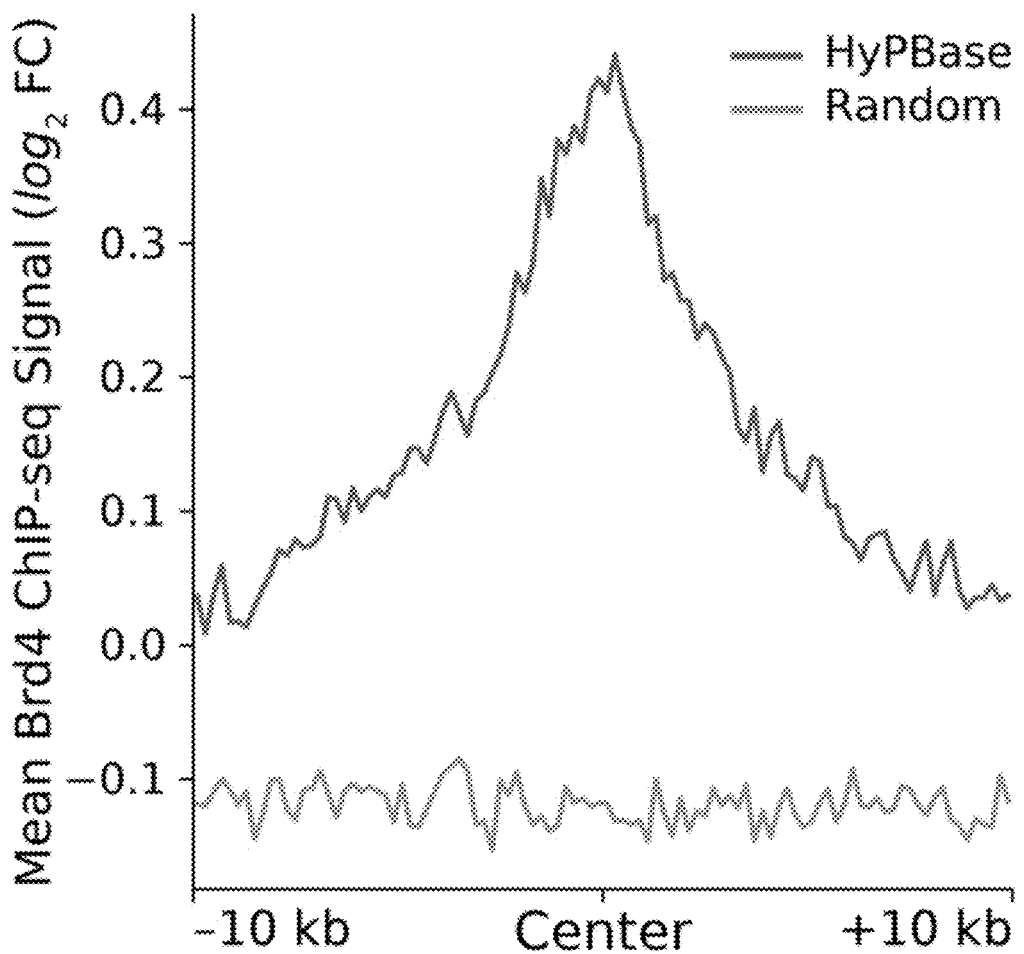
Figure 13D:
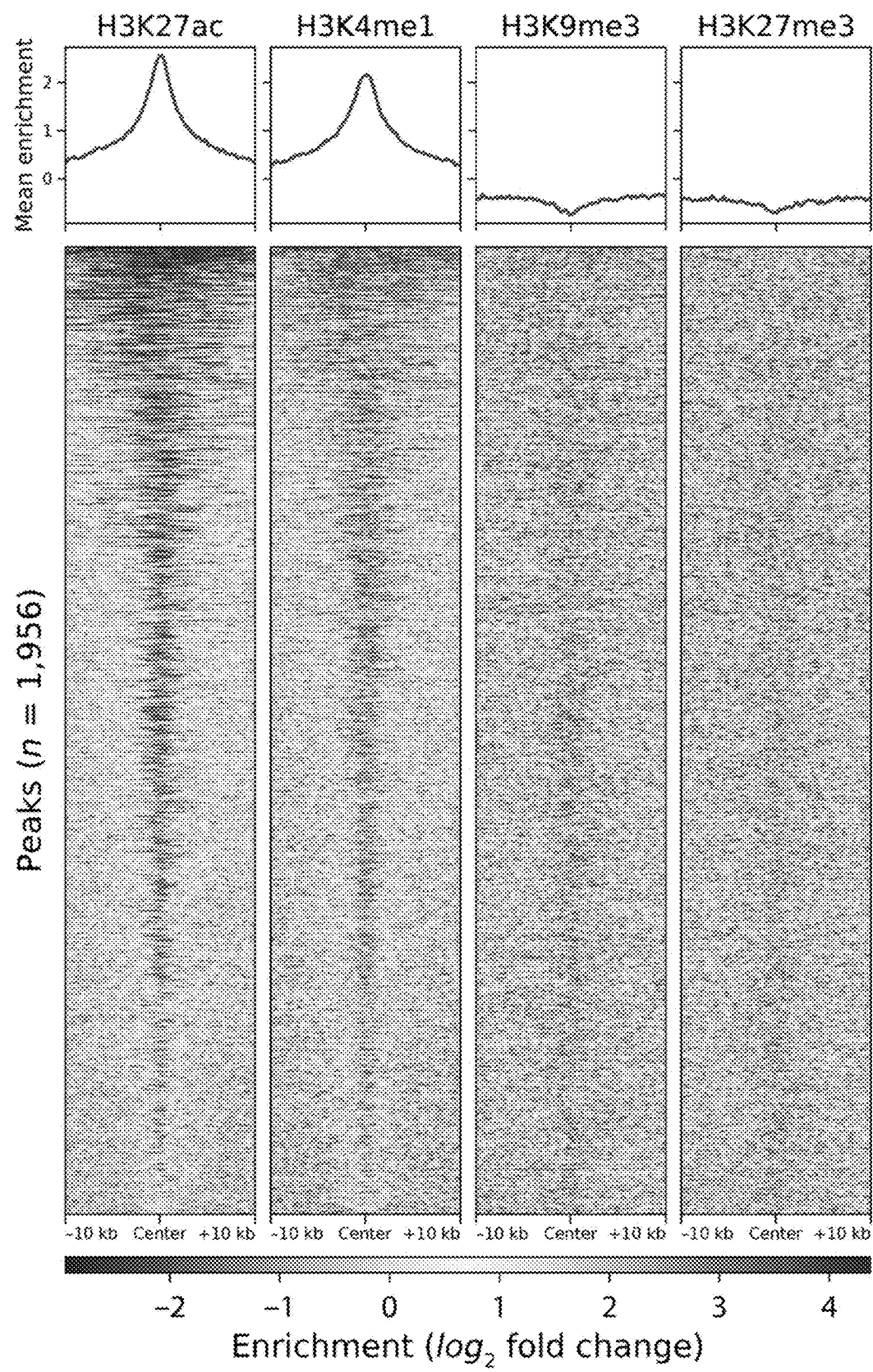
Figure 15:
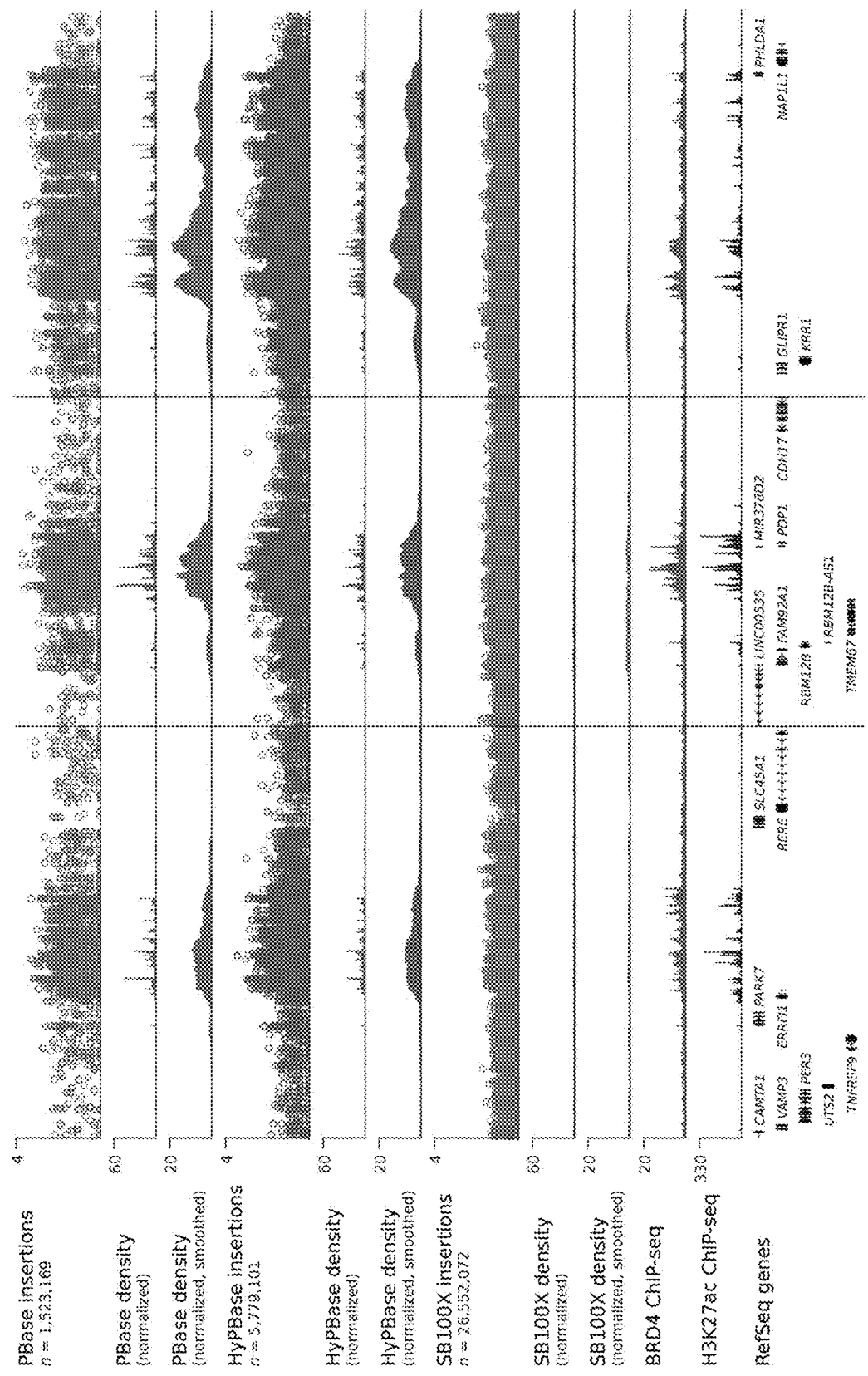
FIG. 15 is a graph showing examples of BRD4-bound super-enhancers identified by PBase and HyPBase calling cards. Three different loci exhibiting non-uniform densities of piggyBac insertions. These densities correlate well with BRD4 and H3K27ac ChIP-seq data. Density tracks are shown before and after smoothing. Sleeping Beauty does not show the same preference for BRD4-bound regions as piggyBac but instead appears uniformly distributed.

Both undirected PBase and HyPBase showed non-uniform densities of insertions at loci bound by BRD4 (see e.g., FIG. 6A and FIG. 15). At statistically significant peaks of piggyBac calling cards, PBase and HyPBase showed high reproducibility of normalized insertions between biological replicates (see e.g., FIG. 6B and FIG. 13B). Next, the mean BRD4 enrichment was calculated, as assayed by ChIP-seq, across these peaks. piggyBac peaks showed significantly increased BRD4 signal compared to a genome-wide permutation of the peaks ($p<10^{-9}$ in both instances, Kolmogorov-Smirnov test; see e.g., FIG. 6C and FIG. 13C). Maximum BRD4 ChIP-seq signal was observed at calling card peak centers and decreased symmetrically in both directions. It was also found that piggyBac peaks show striking ChIP-seq patterns for several histone modifications, in particular an enrichment for H3K27ac ChIP-seq signal (see e.g., FIG. 6D and FIG. 13D). Since bromodomains bind acetylated histones, this observation further supports the hypothesis that undirected piggyBac insertions can be used to map BRD4 binding. These peaks were also enriched in H3K4me1, another canonical enhancer mark, and depleted for H3K9me3 and H3K27me3, modifications associated with repressed chromatin. Taken together, these results demonstrate that piggyBac insertion density is highly correlated with BRD4 binding throughout the genome and that regions enriched for undirected piggyBac insertions share features common to enhancers.

Figure 6E:
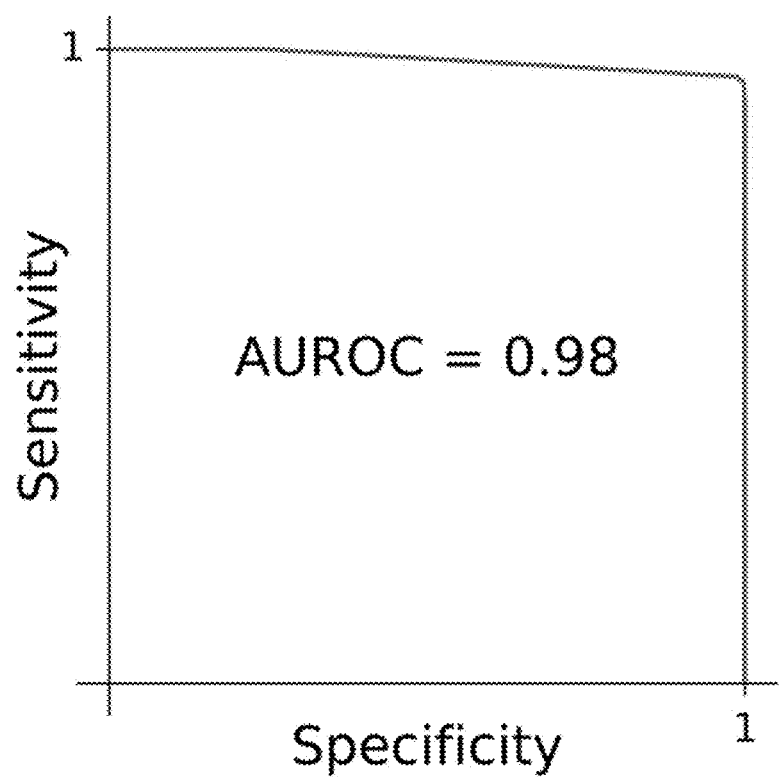
Figure 6F:
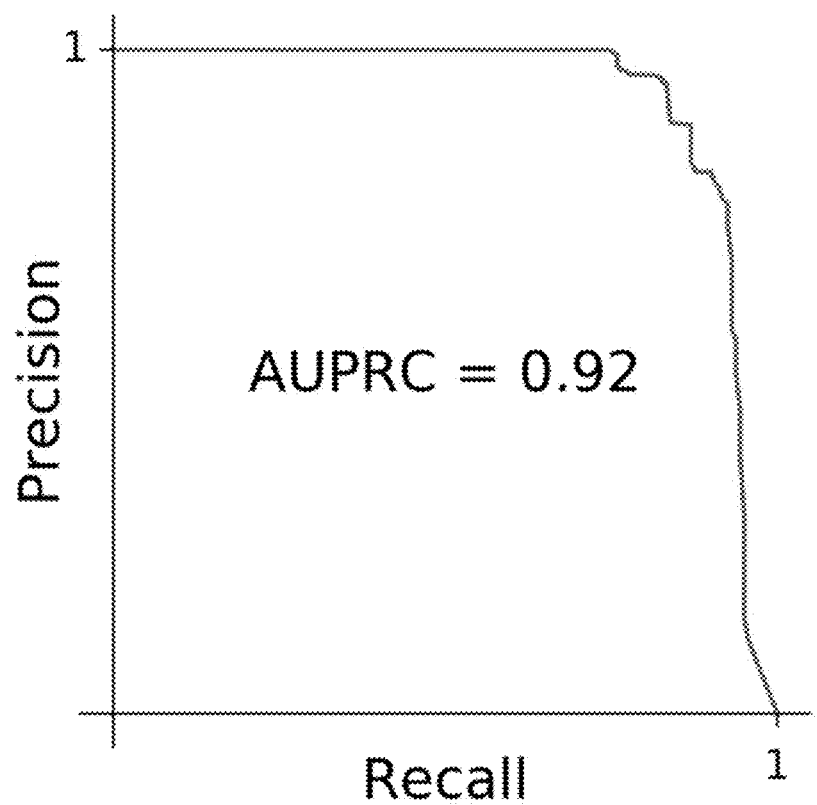
Figure 13E:
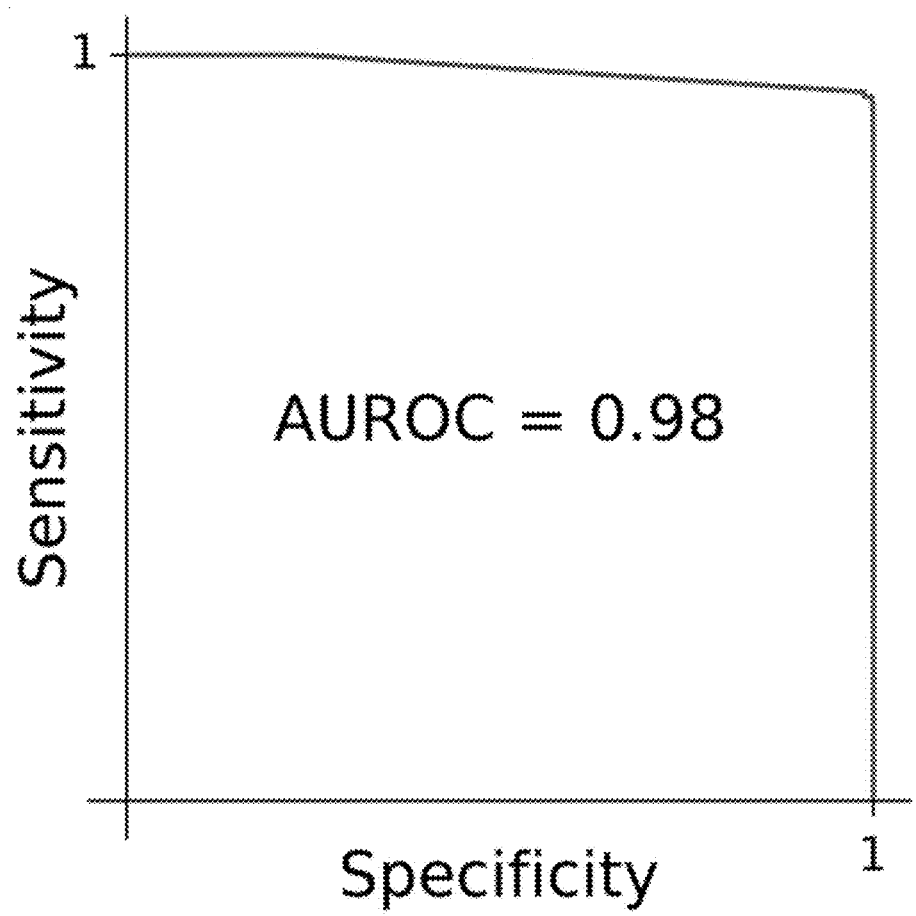
Figure 13F:
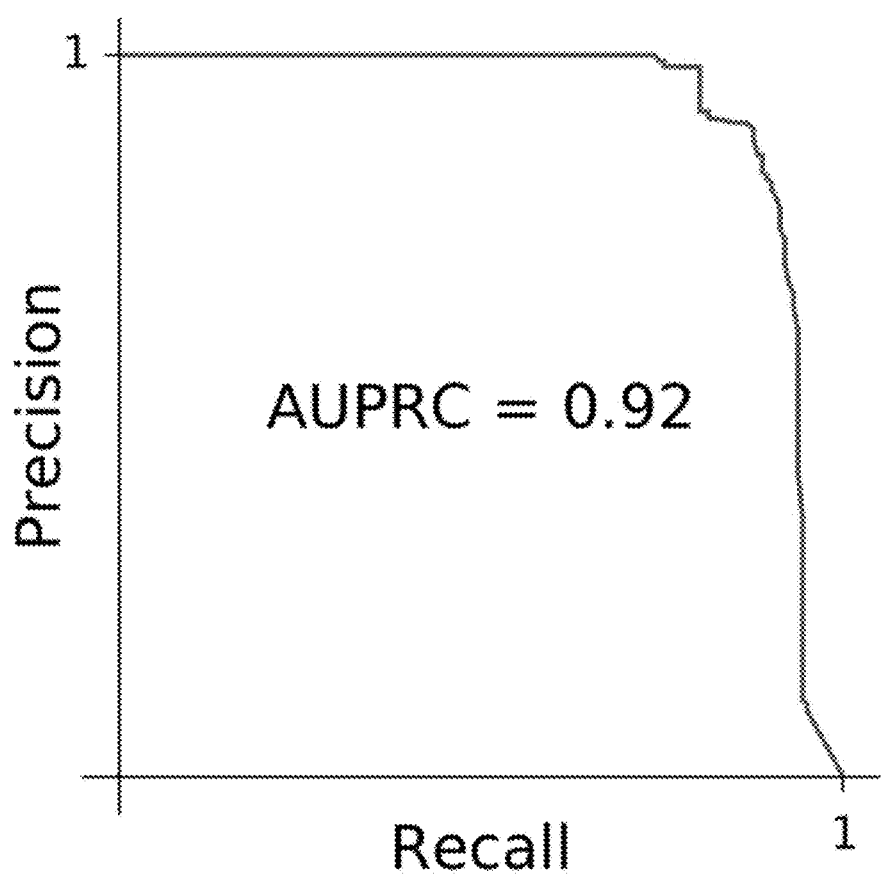

To assess whether piggyBac peaks can be used to identify BRD4-bound SEs, a reference list of Brd4-bound super-enhancers in HCT-116 cells was created (see e.g., FIG. 6A, FIG. 13A) from BRD4 ChIP-seq data. Receiver-operator characteristic curves were then constructed. These are shown for PBase- and HyPBase-derived BRD4-bound super-enhancers in FIG. 6E and FIG. 13E. The high areas under the curves (0.98 in each instance) indicate that BRD4 super-enhancers from piggyBac transpositions can be robustly called. Calling card peaks are highly specific across a range of sensitivities. In addition, calling card peaks have high positive predictive value (AUPRC=0.92 in each instance) across a broad range of sensitivities (see e.g., FIG. 6F, FIG. 13F). Thus, undirected piggyBac transpositions are an accurate assay of BRD4-bound SEs.

Figures 14A, 14B, 14C, 14D:
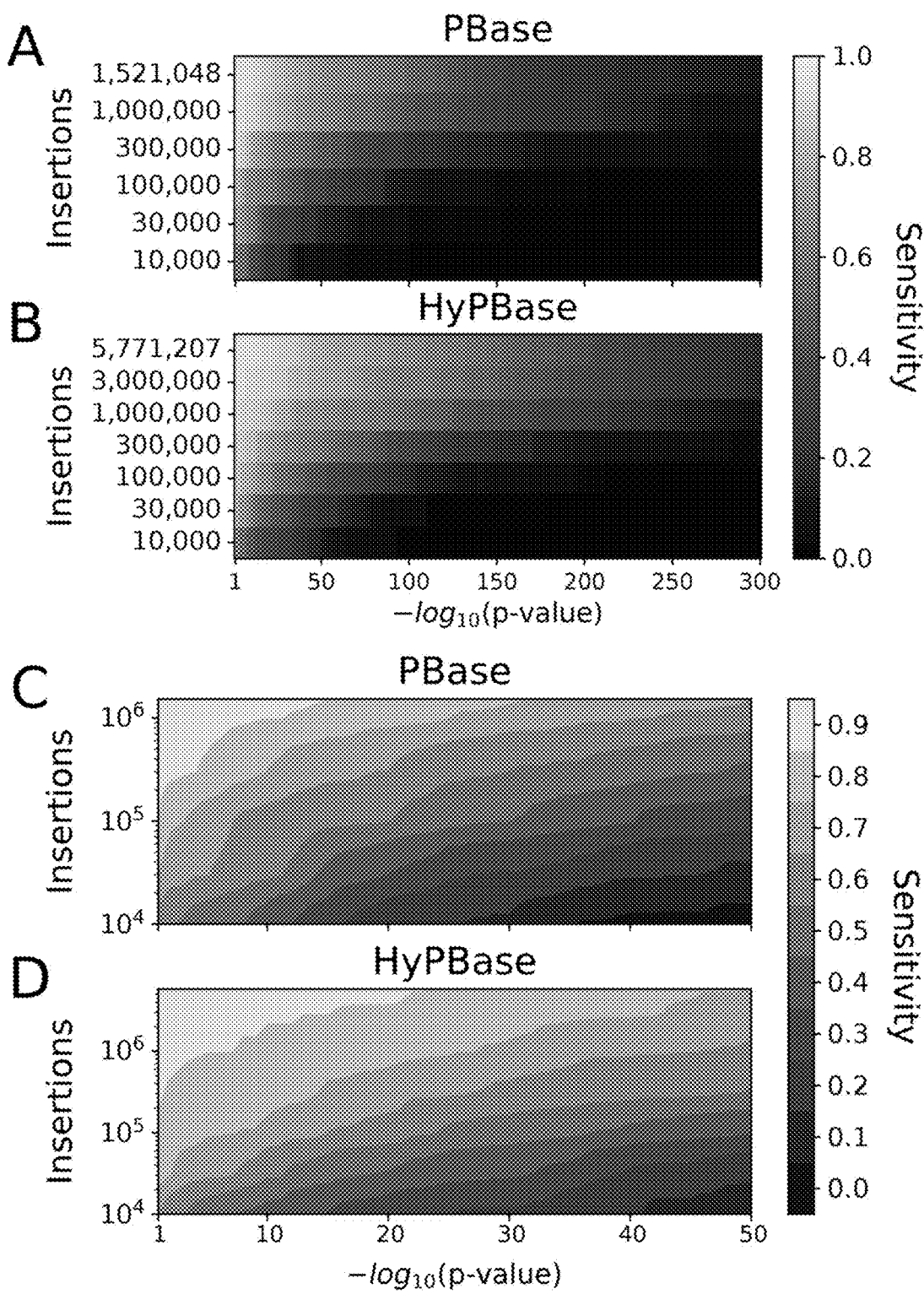
FIG. 14A-FIG. 14D is a series of graphs showing downsampling PBase and HyPBase insertions affects sensitivity to BRD4-bound super-enhancers. (A) Downsampling analysis BRD4-bound SE detection by PBase insertions at various p-value thresholds. (B) Downsampling analysis applied to HyPBase insertions. (C) Linear interpolation applied to (A) to predict SE sensitivity across a range of insertions. (D) Linear interpolation applied to (B).

To better understand the relationship between SE sensitivity and the number of insertions recovered, the data from the PBase and HyPBase experiments was downsampled in half-log increments (see e.g., FIG. 14A and FIG. 14B). The resulting heatmaps indicate that sensitivity increases with the total number of insertions recovered. Since the number of insertions future experiments will yield is difficult to predict, linear interpolation was also performed on the downsampled data. The resulting contour plots (see e.g., FIG. 14C and FIG. 14D) indicate the approximate sensitivity of BRD4-bound SE detection in HCT-116 cells. These results suggest that even with as few as 10,000 insertions, sensitivities around 50% can still be obtained.

Single Cell Calling Cards Enables Simultaneous Identification of Cell Type and Cell Type-Specific TF Binding Sites Next, SRTs were recovered from scRNA-seq libraries. This can enable identification of cell types from transcriptomic clustering and, using the same source material, profile TF binding in those cell types. The 10× Chromium platform was adopted given its high efficiency of cell and transcript capture as well as its ease of use. Like many microfluidic scRNA-seq approaches, the cell barcode and unique molecular index (UMI) are attached to the 3' ends of transcripts. This poses a molecular challenge for SRTs since the junction between the transposon and the genome may be many kilobases away, precluding the use of high-throughput short read sequencing. To overcome this barrier, a circularization strategy was developed to physically bring the cell barcode in apposition to the insertion site (see e.g., FIG. 7A).

A modified version of the bulk SRT amplification protocol was used, where primers were amplified that bound to the universal priming sequence next to the cell barcode and the terminal sequence of the piggyBac TR. These primers were biotinylated and carried a 5' phosphate group. The PCR products of this amplification were diluted and allowed to self-ligate overnight. They were then sheared and captured with streptavidin-coated magnetic beads. The rest of library was prepared on-bead and involved end repair, A-tailing, and adapter ligation. A final PCR step added the required Illumina sequences for high-throughput sequencing. The standard Illumina read 1 primer read the cell barcode and UMI, while a custom read 2 primer, annealing to the end of the piggyBac 5' TR, read into the genome. Thus, both the location of a piggyBac insertion as well as its cell of origin were collected. This method is referred to as single cell calling cards (scCC).

Figure 16A:
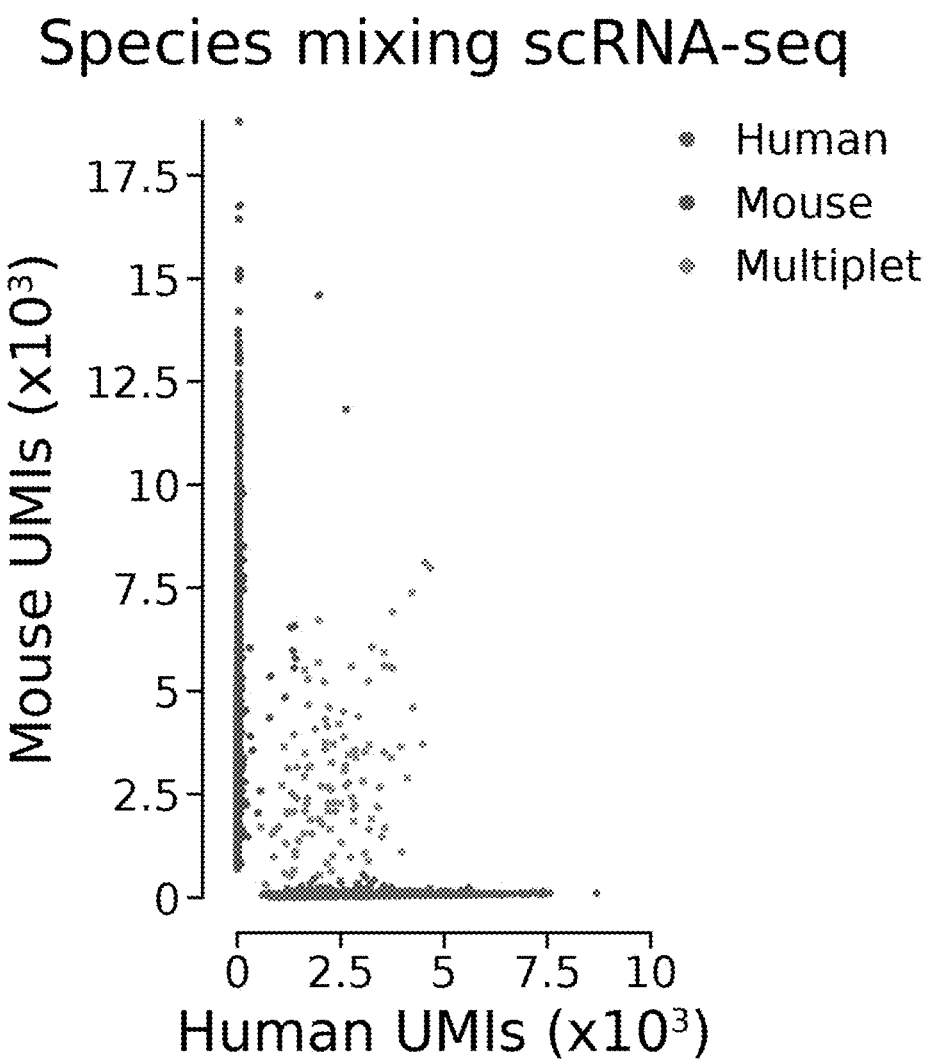
Figure 16B:
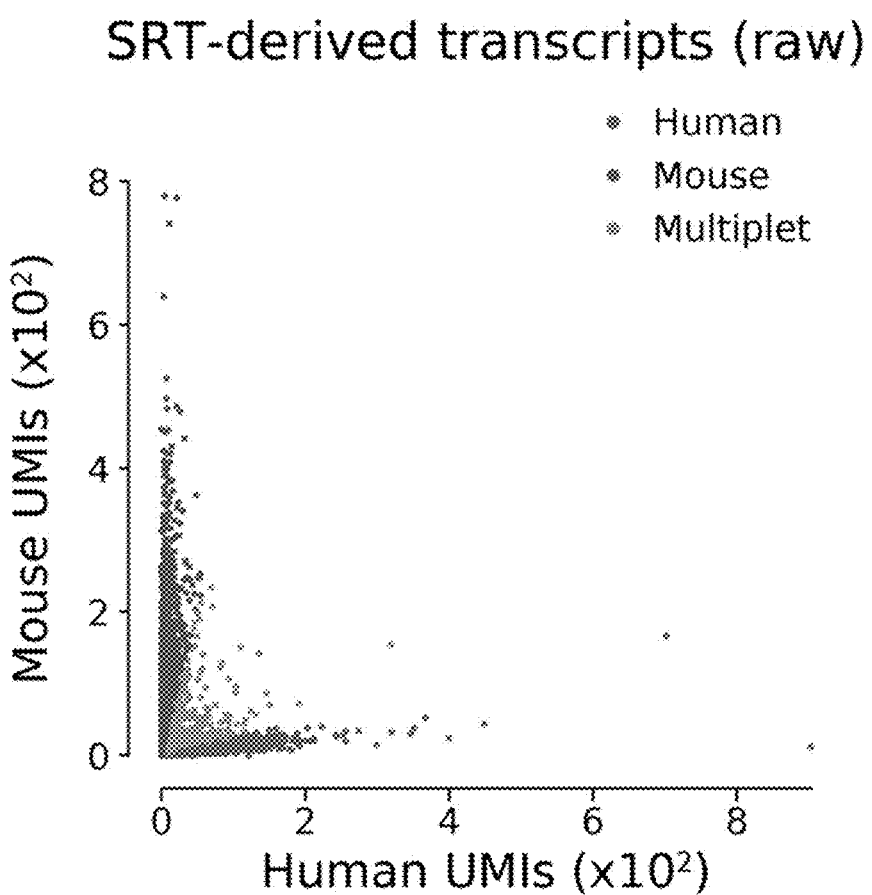
Figure 16C:
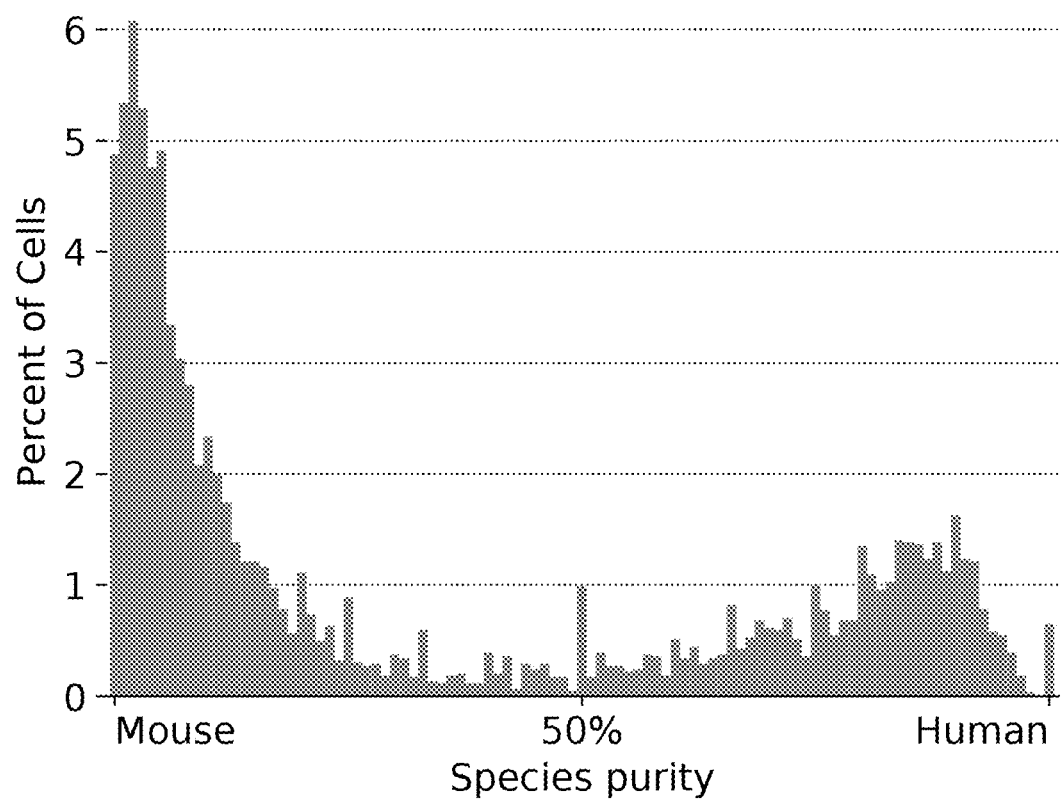

The method was validated by performing with a species-mixing experiment using human HCT-116 cells and mouse N2a cells. Cells were mixed prior to droplet generation and the resulting emulsion was processed through first strand synthesis. At this point, half of the RT product was amplified according to the standard 10× protocol. The resulting scRNA-seq revealed strong species separation with an estimated multiplet rate of 3.2% (see e.g., FIG. 16A). The remainder of the first strand synthesis was used for the scCC protocol. The calling card analysis was restricted to those insertions whose cell barcodes were observed in the scRNA-seq library. The distribution of insertions across these cells reflected a continuum from pure mouse to pure human (see e.g., FIG. 16B-FIG. 16C). Since intramolecular ligation and subsequent PCR may introduce unwanted artifacts, such as mis-assignment of a barcode from cell type A to an insertion site in cell type B, it was required that a given insertion in a given cell must have at least two different UMIs associated with it. Imposing this filter improved the number of pure mouse and human cells (see e.g., FIG. 16D), yielding clear species separation with an estimated multiplet rate of 7.8% (see e.g., FIG. 7B). This establishes that the method can map calling card insertions in single cells.

Figure 7D:
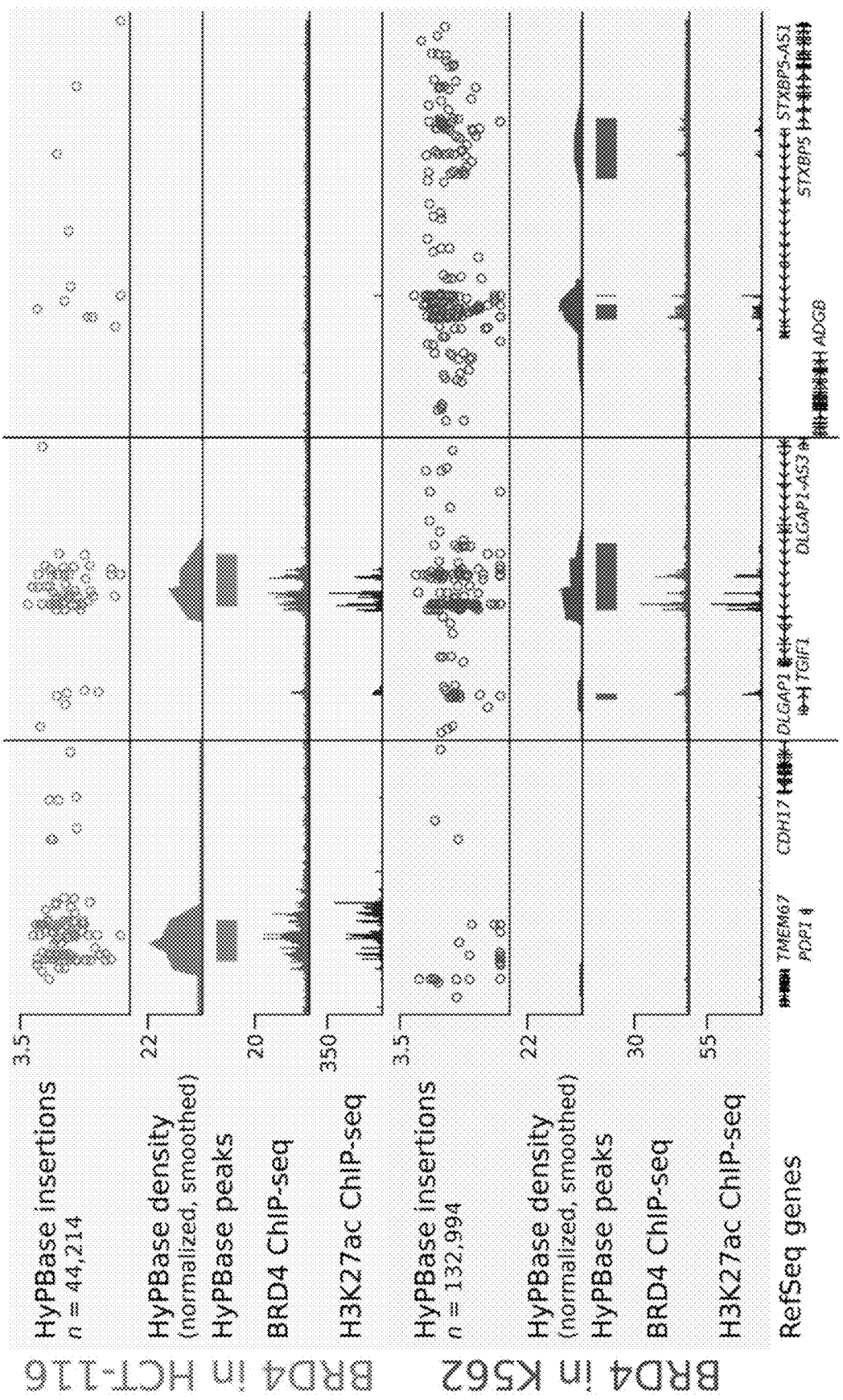
Figure 17A:
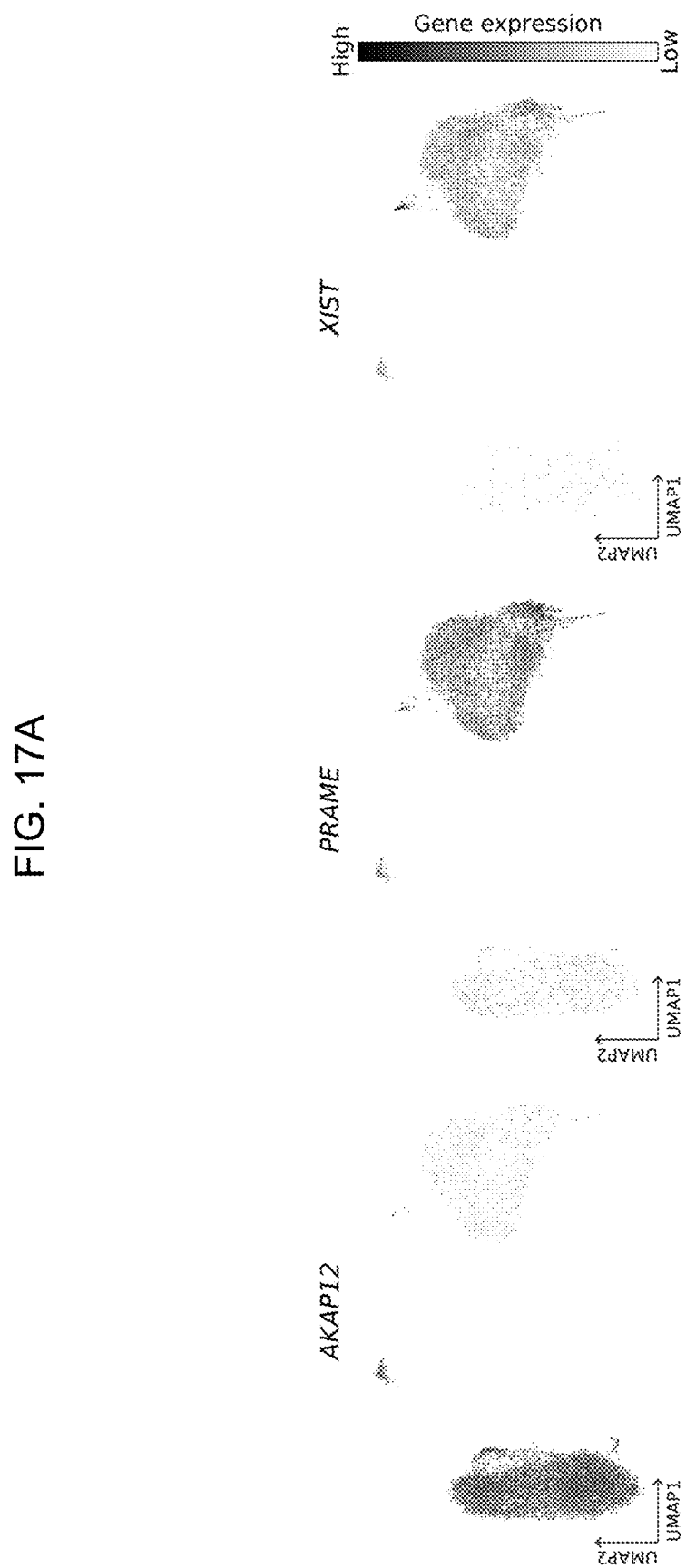
Figure 17B:
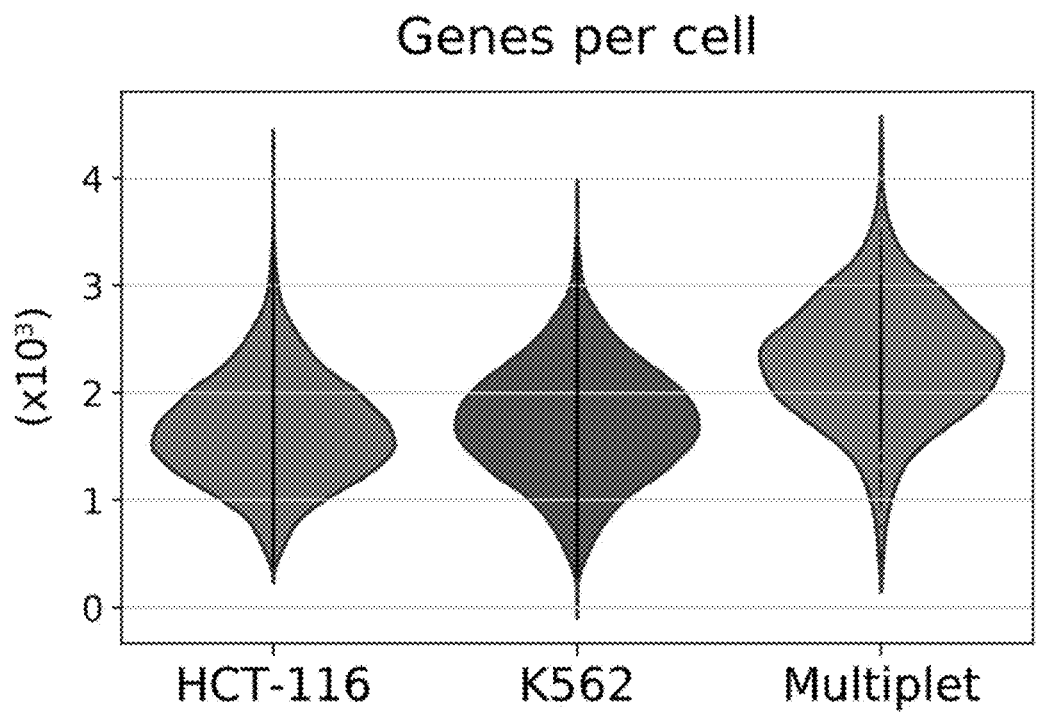
Figure 17C:
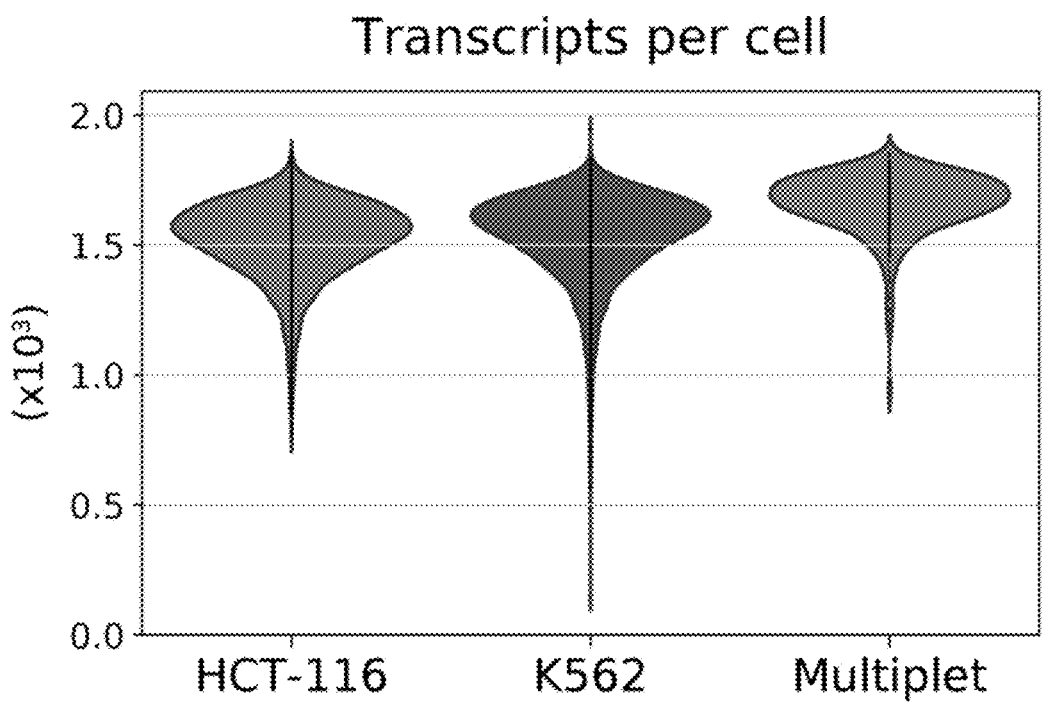
Figure 17E:
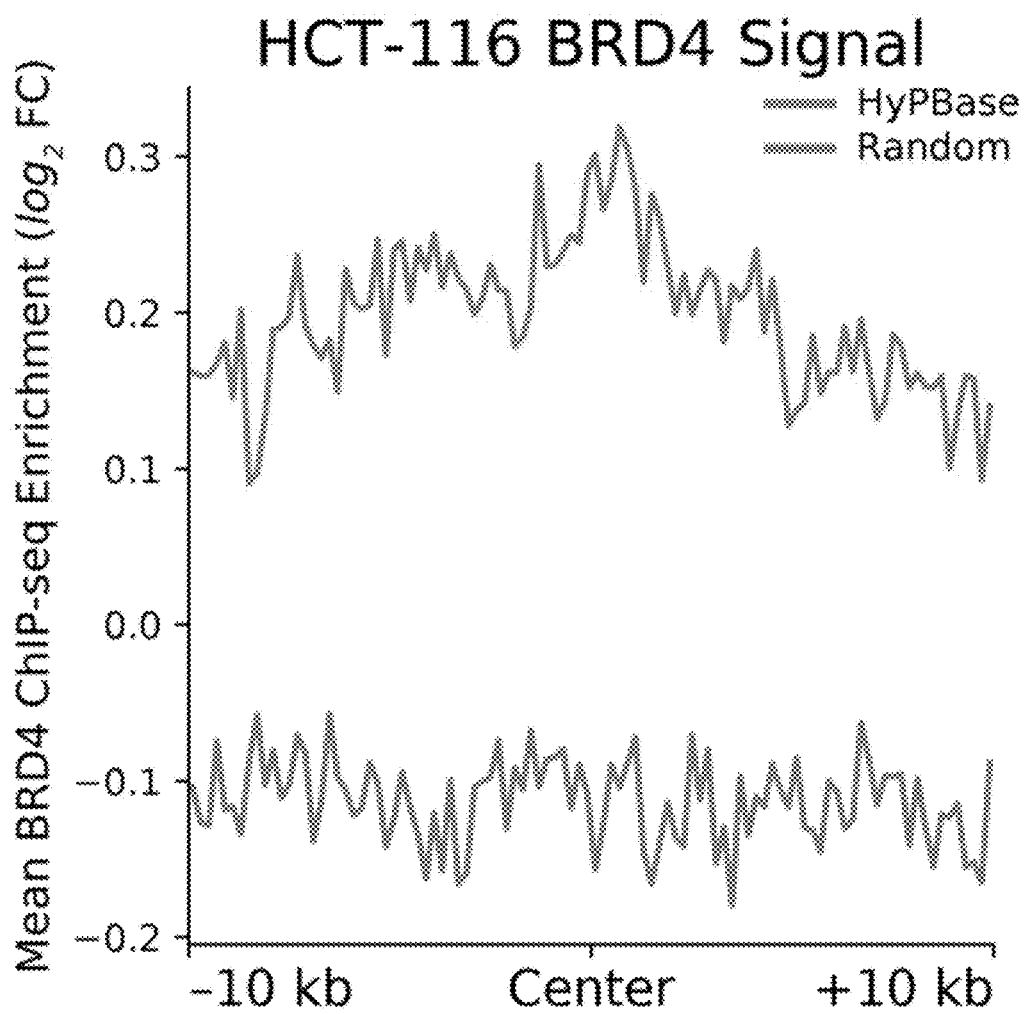
Figure 17F:
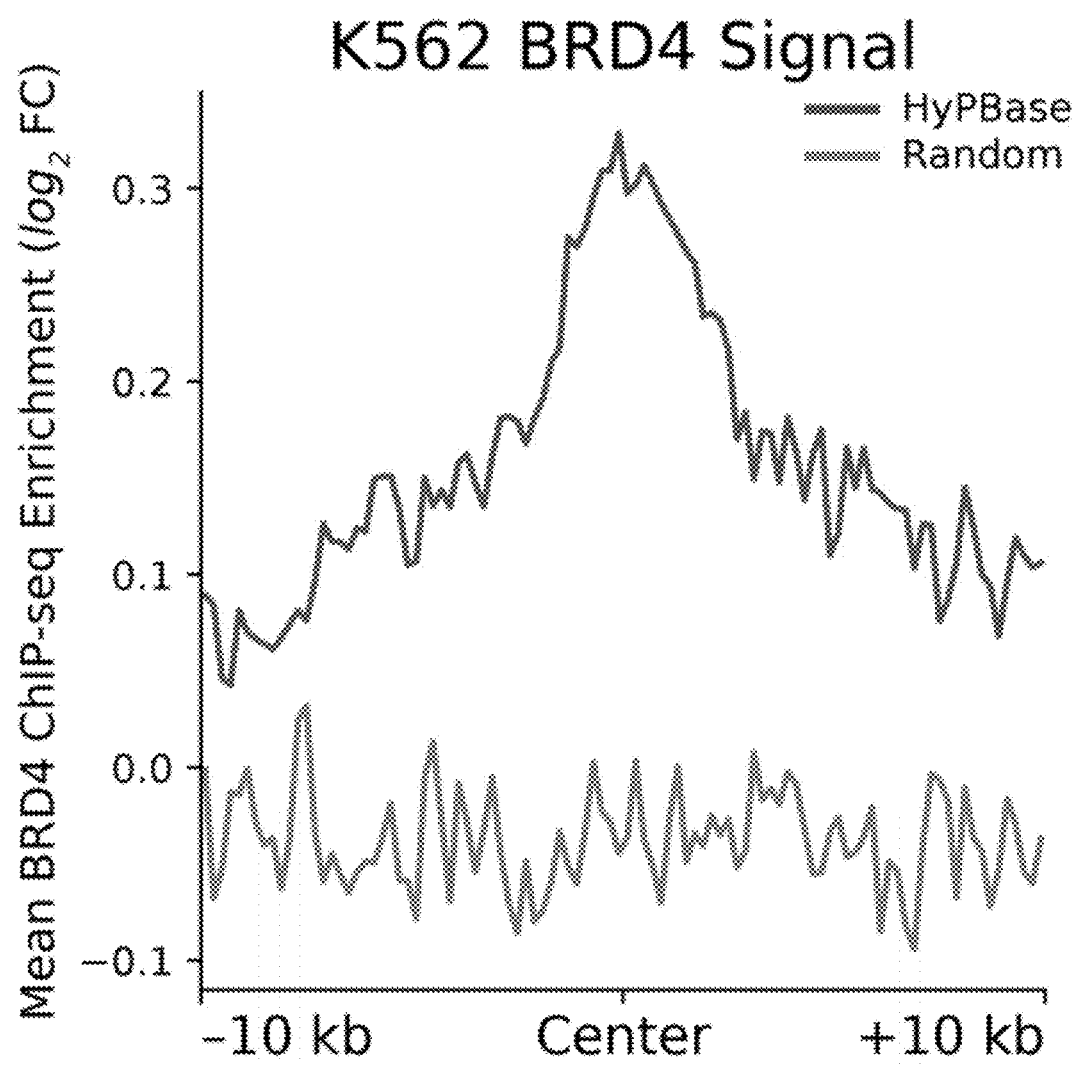

It was then tested whether scCC could discern cell type-specific TF binding. Two human cell lines, HCT-116 and K562, were transfected with HyPBase and PB-SRT-Puro and mixed together. The resulting scRNA-seq libraries clearly identified the two major cell populations (see e.g., FIG. 7C and FIG. 17A). scCC libraries were then prepared from these cells and the cell barcodes from the HCT-116 and K562 clusters were used to assign insertions to the two different cell types. 44,214 insertions were obtained from 12,891 HCT-116 cells (mean 3.4 insertions per cell; mean 136 reads per insertion) and 132,994 insertions from 11,912 K562 cells (mean 11 insertions per cell; mean $10^3$ reads per insertion). The distribution of insertions per cell varied by cell type (see e.g., FIG. 17D) and does not appear to be correlated with differences in total RNA content (see e.g., FIG. 17B-FIG. 17C). Over 93% and 97% of HCT-116 and K562 cells, respectively, had at least one insertion event. Using scCC insertion data alone, peaks were called and Brd4-bound loci that were specific to HCT-116 cells, shared between HCT-116 and K562, and specific to K562 cells, were successfully identified, respectively (see e.g., FIG. 7D). Both HCT-116 and K562 peaks showed statistically significant enrichment for BRD4 ChIP-seq signal ($p<10^{-9}$ in both instances, Kolmogorov-Smirnov test; see e.g., FIG. 17E-FIG. 17F). From the earlier downsampling analysis, it was estimated that with a p-value cutoff of $10^{-9}$, the sensitivity for detecting Brd4-bound super-enhancers would be approximately 60% (see e.g., FIG. 14D). The actual sensitivity at this level of recovery was 64%, indicating that downsampling analysis can reasonably estimate the performance of scCC. In all, these experiments demonstrate that scCC can be used to deconvolve cell type-specific TF binding.

Figure 7E:
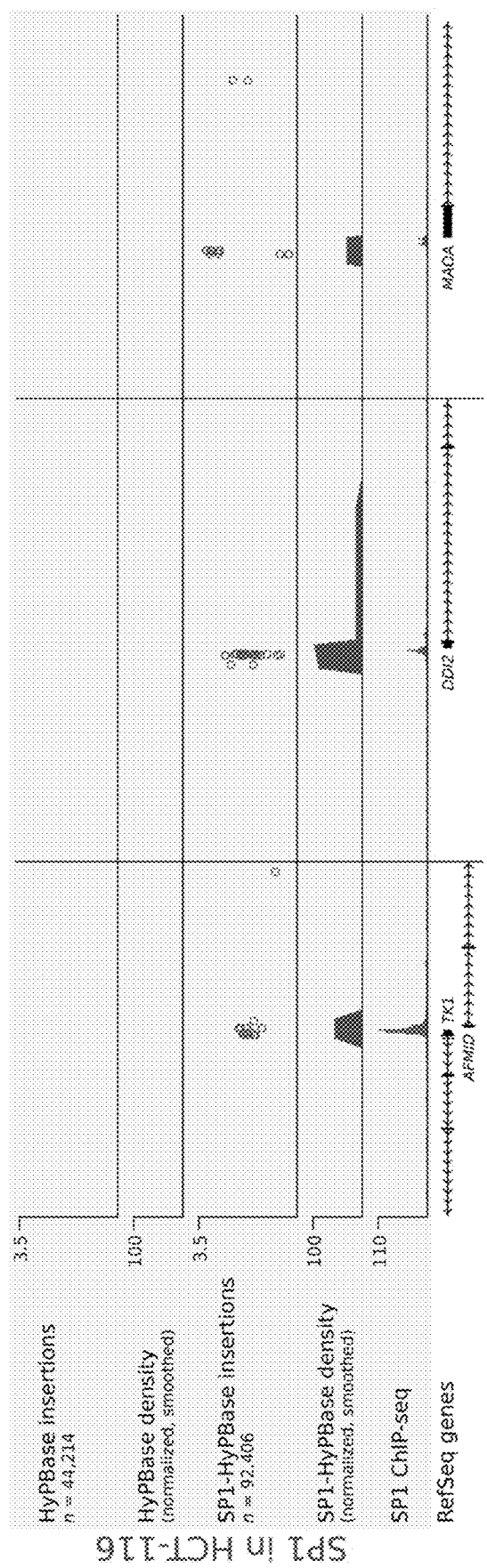
Figure 7F:
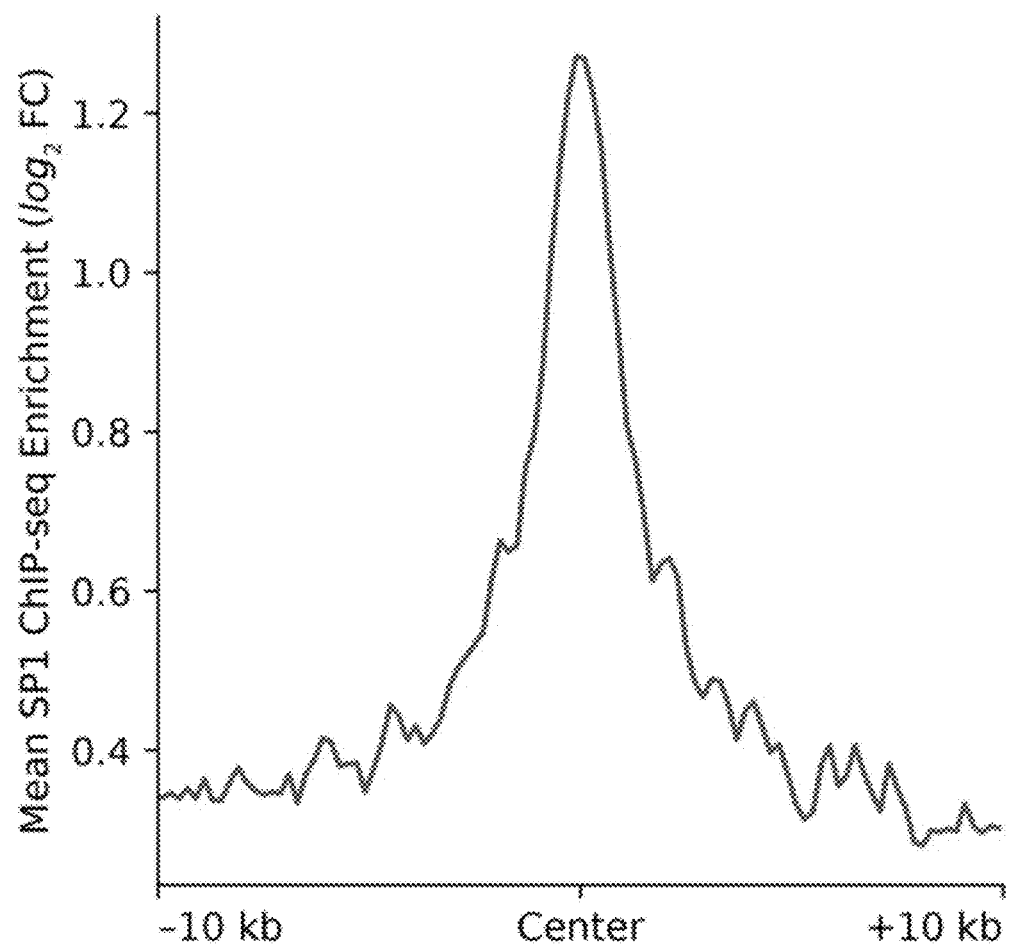
Figure 8:
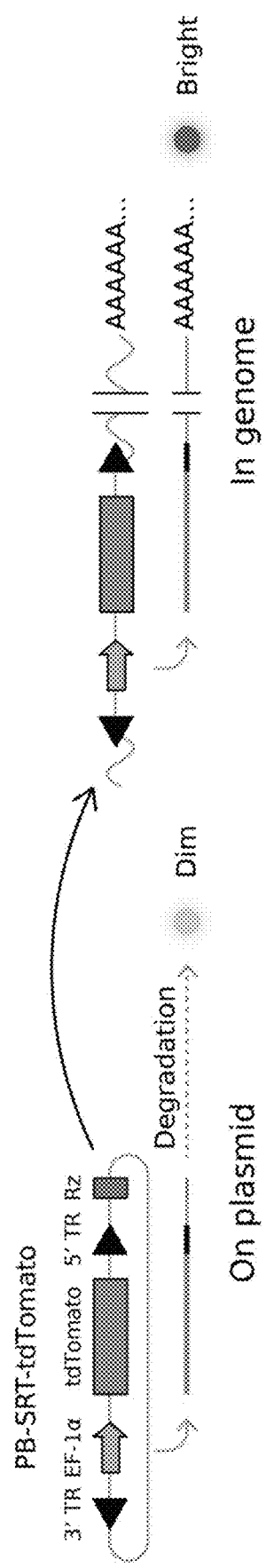
FIG. 8 is a schematic of PB-SRT-tdTomato, an SRT compatible with in vivo experiments. The pre-transposition tdTomato transcript (left) is degraded by the downstream ribozyme (Rz), leading to low fluorescence intensity. After transposition into the genome, the self-reporting transcript is stabilized and results in a bright signal.
Figure 17G:
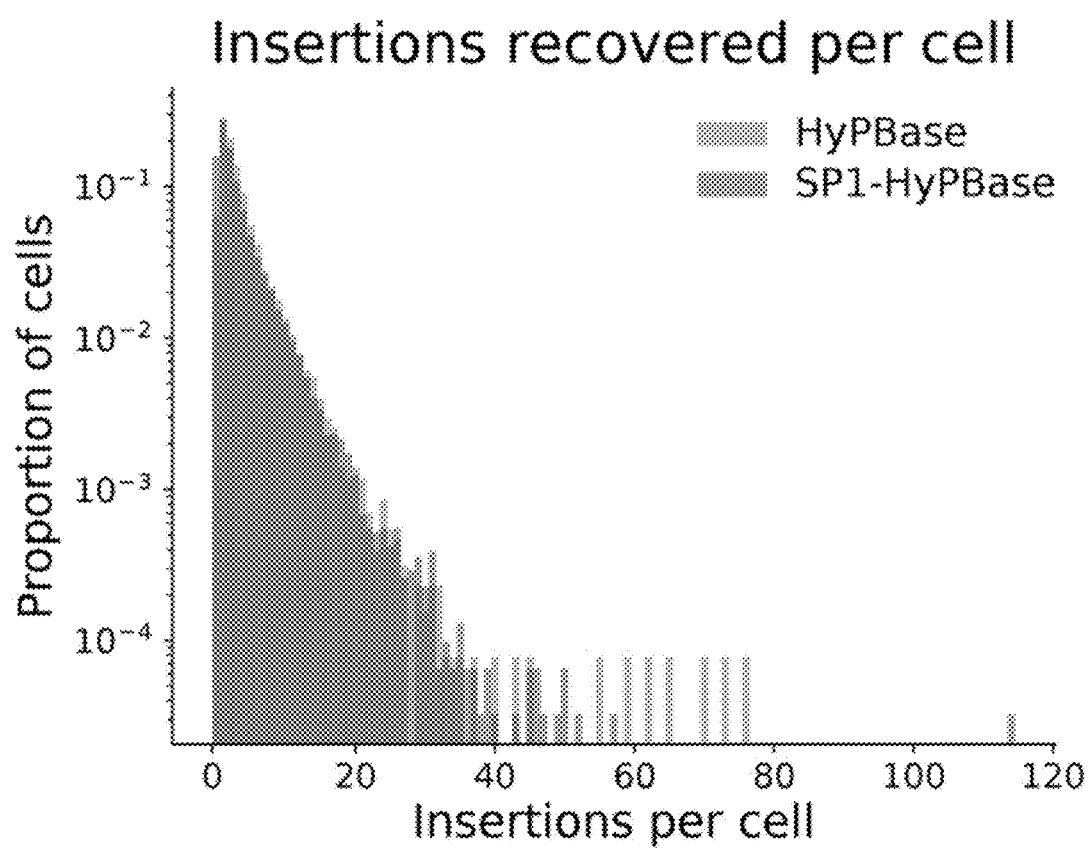
Figure 17H:
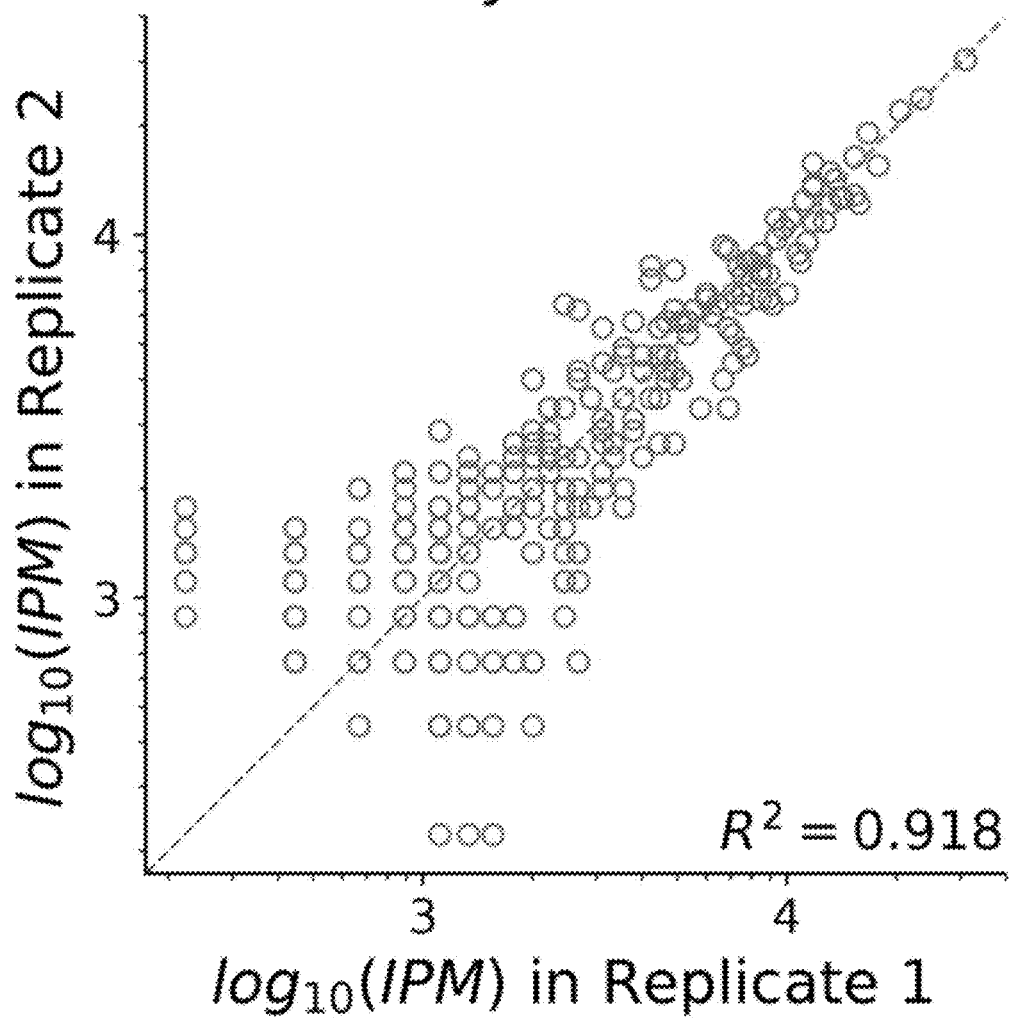
Figure 17I:
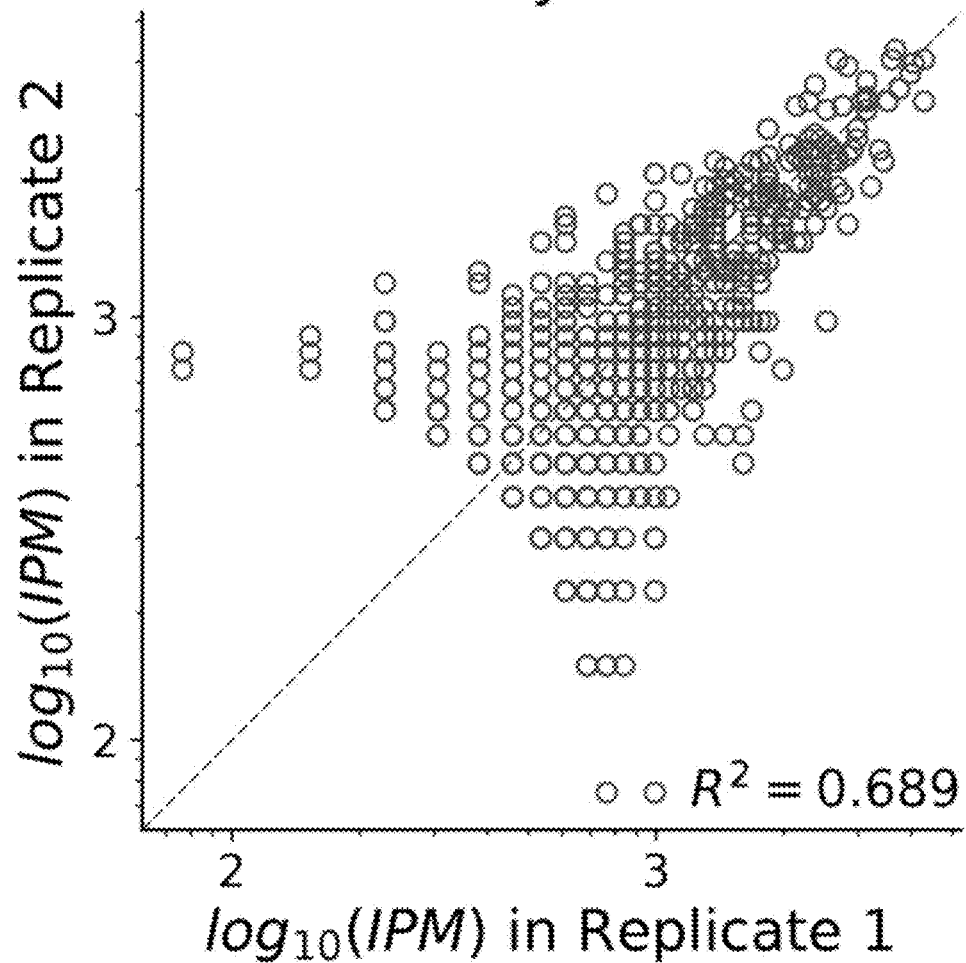

Since these Brd4 binding sites were identified using undirected HyPBase, it was also sought to confirm that TF-piggyBac fusions would still work with scCC. HCT-116 cells were transfected with SP1-HyPBase and scRNA-seq was performed. scCC libraries were made from these experiments and 92,406 insertions were identified from 30,682 cells (mean 3 insertions per cell; mean 129 reads per insertion). Over 84% of cells had at least one insertion. The slight reduction in insertions per cell with the SP1 fusion is consistent with previous studies, although the distribution of insertions recovered per cell was similar to that of the undirected transposase (see e.g., FIG. 17G). As was observed in bulk (see e.g., FIG. 12A), SP1-HyPBase-directed insertions recovered from single cells localize to SP1 binding sites (see e.g., FIG. 7E). Finally, the reproducibility of the scCC method was tested. Both single cell HyPBase and SP1-HyPBase showed high concordance between biological replicates at statistically significant peaks (see e.g., FIG. 17H and FIG. 17I). Collectively, these experiments establish that scCC can be used to identify cell type-specific binding sites of both bromodomain and DNA-binding TFs.

Discussion

Mapping TF binding in heterogeneous tissues is a challenging problem because traditional methods combine signals from multiple cell types into a single, agglomerated profile. The difficulty is further compounded if individual cell types are difficult to identify, isolate, or are rare, precluding their study. Single cell RNA-seq is a promising paradigm for handling such heterogeneity. Until now, it has been impossible to directly study the actions of individual TFs and connect them to specific cell states. Here is presented a new method, single cell calling cards (scCC), that enables simultaneous identification of cell types and TF binding sites from complex mixtures and tissues. This is an important addition to the single cell repertoire and fills a recognized void in the field. It is anticipated that this technique will enable researchers to study the consequences of TF binding in a variety of ex vivo and in situ models.

A concern with any transposon-based technique is the potential for deleterious interruption of target genes leading to cell death and thereby false negatives. Previous experiments in diploid yeast found that calling cards are deposited into promoters of essential and non-essential genes at comparable frequencies. Since mammalian genomes have much larger intergenic regions than yeast, human and mice genomes are likely also able to tolerate calling card transpositions. Indeed, the fact that SRTs can be deposited in the developing mouse brain into enhancers and super-enhancers suggests a small mutagenic burden.

One of the limitations of this technique is the relatively few insertions recovered on a per-cell basis, inflating the number of cells that must be analyzed to achieve good sensitivity. Previous studies have reported up to 15-30 insertions per cell for PBase, and likely higher for HyPBase. Here, fewer insertions were recovered per cell than this, on average, in the experiments. This is likely due to the low capture rate of mRNA transcripts, which is common to all scRNA-seq methods. The inclusion of cis-regulatory features known to enhance mRNA maturation and stability, such as the woodchuck hepatitis virus posttranscriptional regulatory element (WPRE) may increase representation of SRTs in scRNA-seq libraries. Furthermore, as the transcript capture rates of scRNA technologies improve, it is expected that the sensitivity of the method will increase. The sensitivity of scCC can also be improved by simply analyzing larger numbers of cells, such as with cell hashing or combinatorial barcoding. Since the per-cell costs for scRNA-seq are exponentially falling, it is expected that scCC can be used to analyze TF binding in even very rare cell types in the near future. Alternatively, SRTs can be combined with Cre.

The scCC experiments described here employed the piggyBac transposase, but for some applications, the use of other transposases may prove advantageous. piggyBac inserts almost exclusively into TTAA tetranucleotides. For TFs that bind GC-rich regions or have high GC-content motifs, piggyBac fusions may have a difficult time finding nearby insertion sites. Sleeping Beauty, which inserts into TA dinucleotides, or Tol2, which does not have a strict insertion site preference, could be used to overcome these limitations.

However, the natural affinity of the piggyBac transposase for BRD4 makes it the ideal choice for the study of BRD4-bound SEs, which play important regulatory roles in development and disease. It is unclear why piggyBac shows such an affinity. Recent evidence suggests that SEs form intranuclear liquid phase condensates and that SE-associated proteins like MED1 and BRD4 have intrinsically disordered regions that may allow them to form these condensates. It may be that piggyBac has a similarly disordered domain that allows it to preferentially enter these condensates, thereby enriching SEs with insertions.

The defining feature of the scCC method is the self-reporting transposon (SRT). While herein the piggyBac and Sleeping Beauty SRTs are described, the self-reporting paradigm should be generalizable to any transposon lacking a polyadenylation signal (PAS) in at least one terminal repeat. Expanding the palette of SRTs will illuminate the genome-wide behaviors of transposases and may yield further insight into chromatin dynamics. Simultaneous expression of many TFs, each tagged to a different transposase, may also enable multiplexed studies of TF binding in the same cells. Mapping SRTs using cellular RNA appears to be substantially more efficient than the DNA-based inverse PCR method, but the reasons for this are somewhat unclear. Some efficiency is likely gained by eliminating self-ligation, as well as having multiple mRNA copies of each insertion to buffer against PCR artifacts. It is also unknown what fraction of self-reporting transcripts are actually polyadenylated as opposed to merely containing A-rich genomic tracts. Non-genic PASs prevent anti-sense transcription, which suggests that PASs may be more common in the genome than previously appreciated. Targeted 3'-end sequencing of SRT libraries should help resolve this question, while long-read sequencing of self-reporting transcripts may identify non-canonical PAS. Finally, SRTs could lead to new single cell transposon-based assays. For example, just as CRISPR/Cas9 has been combined with scRNA-seq to read out the transcriptional effects of gene deletion, SRTs will allow transposon mutagenesis screens to be read out by scRNA-seq in a highly parallel fashion.

Finally, since calling card insertions are genomically integrated and preserved through mitosis, they could serve as a molecular record of cellular events. The use of an inducible transposase would enable the recording and identification of temporally-restricted TF binding sites. This would help uncover the stepwise order of events underlying the regulation of specific genes and inform cell fate decision making. More generally, transposon insertions could serve as barcodes of developmental lineage. Single transposition events have been used to delineate relationships during hematopoiesis. Multiplexing several SRTs across every cell in an organism could code lineage in a cumulative and combinatorially diverse fashion, generating high-resolution cellular phylogenies.

Methods

Cell Culture

HCT-116, N2a, and HEK293T cells were cultured in Dulbecco's Modified Eagle Medium (DMEM; Gibco #11965-084) supplemented with 10% fetal bovine serum (FBS; Peak Serum #PS-FB3) and 1% antibiotic-antimycotic (Anti-Anti; Gibco #15240-062). K562 cells were grown under the same conditions as the HCT-116 and N2a except replacing DMEM with RPMI 1640 Medium (Gibco #11875-085). Cells were grown at 37° C. with 5% carbon dioxide ($CO_2$). Puromycin (Sigma #P8899) was added 24 hours after transfection at a final concentration of 2 μg/ml. Media was replenished every 2 days.

DNA- Vs RNA-Based Recovery

Approximately 500,000 HCT-116 cells were plated in a single well of a 6-well plate. Cells were transfected with 2.5 μg of the SP1-PBase plasmid (for a full list of plasmids, see TABLE 1) and 2.5 μg of the PB-SRT-Puro plasmid using Lipofectamine 3000 (Thermo Fisher #L3000015) following manufacturer's instructions.

TABLE 1

Plasmids referenced herein.

| Plasmid | Description | Internal Accession No. | Addgene? | Addgene Accession No. |
|---------|-------------|------------------------|----------|------------------------|
| PBase | piggyBac transposase | pRM1024 | NA | NA |

TABLE 1-continued

Plasmids referenced herein.

| Plasmid | Description | Internal Accession No. | Addgene? | Addgene Accession No. |
|---|---|---|---|---|
| HyPBase | Hyperactive piggyBac transposase | pRM1114 | NA | NA |
| SP1-PBase | SP1 fused to piggyBac | pRM1023 | NA | NA |
| SP1-HyPBase | SP1 fused to hyperactive piggyBac | pRM1677 | NA | NA |
| PB-SRT-Puro | piggyBac SRT with puromycin reporter | pRM1304 | NA | NA |
| PB-SRT-tdTomato | piggyBac SRT with tdTomato reporter | pRM1535 | NA | NA |
| SB100X | Hyperactive Sleeping Beauty transposase | pRM1137 | NA | NA |
| SB-SRT-Puro | Sleeping Beauty SRT with puromycin reporter | pRM1668 | NA | NA |

After 24 hours, cells were split and plated 1:10 in each of three 10 cm dishes. Puromycin was then added and colonies were allowed to grow out under selection for two weeks. Approximately 2,300 colonies were obtained. All cells were pooled together and split into two populations: one was subjected to DNA extraction, self-ligation, and inverse PCR, as described previously; while the other underwent RNA extraction and SRT library preparation.

In Vitro Bulk Calling Card Experiments 10-12 replicates of HCT-116 cells were cotransfected with 5 µg of PB-SRT-Puro plasmid and 5 µg PBase plasmid via Neon electroporation (Thermo Fisher #MPK10025). Each replicate contained 2×10$^6$ cells. As a negative control, one replicate of HCT-116 cells was transfected with 5 µg PB-SRT-Puro plasmid only. The following settings were used-pulse voltage: 1,530 V; pulse width: 20 ms; pulse number: 1. Each replicate was allowed to recover in a single well of a 6-well plate for 24 hours before being split 1:1 into a 10 cm dish and adding puromycin. Cells were grown under selection for one week, by which time almost all negative control transfectants were dead. The same experimental setup was used for experiments with PB-SRT-Puro and each of SP1-PBase, HyPBase, and SP1-HyPBase plasmids, as well as with SB-SRT-Puro and SB100× plasmids. Each replicate was cultured independently under aforementioned media conditions. After 7 days, each replicate was dissociated with trypsin-EDTA (Sigma #T4049) and single cell suspensions were created in phosphate-buffered saline (PBS; Gibco #14190-136). Aliquots of each replicate were cryopreserved in cell culture media supplemented with 5% DMSO. The remaining cells were pelleted by centrifugation at 300 g for 5 minutes. Cell pellets were either processed immediately or kept at −80° C. in RNAProtect Cell Reagent (QIAGEN #76526).

Isolation of Bulk RNA and Reverse Transcription

Total RNA was isolated from each replicate using the RNEasy Plus Mini Kit (QIAGEN #74134) following manufacturer's instructions. Briefly, cell pellets were resuspended in 600 µl of Buffer RLT Plus with 1% β-mercaptoethanol (Gibco #21985-023). Cells were homogenized by vortexing. RNA was bound on gDNA Eliminator spin columns and treated with DNase (QIAGEN #79254) while on the column. After washing, RNA was eluted in 40 µl RNase-free H$_2$O. RNA was quantitated on a NanoDrop ND-1000 spectrophotometer (Thermo Fisher).

First strand synthesis on each replicate was performed with Maxima H Minus Reverse Transcriptase (Thermo Fisher #EP0752). 2 µg of total RNA was mixed with 1 µl 10 mM dNTPs (Clontech #639125) and 1 µl of 50 µM SMART_dT18VN primer (for a complete list of primer sequences, see TABLE 2), which brought the total volume up to 14 µl, which was then incubated it at 65° C. for 5 minutes.

TABLE 2

Oligonucleotides referenced in this work.

| Primer | Primer Sequence | Purification | Notes |
|---|---|---|---|
| SMART_dT18VN (SEQ ID NO: 13) | AAGCAGTGGTATCAACGCAGAGTACGTTTTTTTTTTTTTTTTTTTTTTTTT TTTTTVN | Standard desalt | RT primer for bulk RNA calling card recovery |
| SMART (SEQ ID NO: 14) | AAGCAGTGGTATCAACGCAGAGT | Standard desalt | PCR primer for bulk RNA calling card amplification |
| SRT_PAC_F1 (SEQ ID NO: 15) | CAACCTCCCCTTCTACGAGC | Standard desalt | Puromycin marker in SRT |
| SRT_tdTomato_F1 (SEQ ID NO: 16) | TCCTGTACGGCATGGACGAG | Standard desalt | tdTomato marker in SRT |
| Raff_ACTB_F (SEQ ID NO: 17) | CCTCGCCTTTGCCGATCCG | Standard desalt | Human ACTB primer (for RT control) |
| Raff_ACTB_R (SEQ ID NO: 18) | GGATCTTCATGAGGTAGTCAGTCAGGTCC | Standard desalt | Human ACTB primer (for RT control) |

TABLE 2-continued

Oligonucleotides referenced in this work.

| Primer | Primer Sequence | Purification | Notes |
|---|---|---|---|
| OM-PB-ACG (SEQ ID NO: 19) | AATGATACGGCGAC CACCGAGATCTACAC TCTTTCCCTACACGA CGCTCTTC CGATCTACGTTTAC GCAGACTATCTTTC TAG | Standard desalt | For use with piggyBac SRTs |
| OM-PB-CTA (SEQ ID NO: 20) | AATGATACGGCGAC CACCGAGATCTACAC TCTTTCCCTACACGA CGCTCTTC CGATCTCTATTTAC GCAGACTATCTTTC TAG | Standard desalt | For use with piggyBac SRTs |
| OM-PB-GAT (SEQ ID NO: 21) | AATGATACGGCGAC CACCGAGATCTACAC TCTTTCCCTACACGA CGCTCTTC CGATCTGATTTAC GCAGACTATCTTTC TAG | Standard desalt | For use with piggyBac SRTs |
| OM-PB-TGC (SEQ ID NO: 22) | AATGATACGGCGAC CACCGAGATCTACAC TCTTTCCCTACACGA CGCTCTTC CGATCTTGCTTTAC GCAGACTATCTTTC TAG | Standard desalt | For use with piggyBac SRTs |
| OM-PB-TAG (SEQ ID NO: 23) | AATGATACGGCGAC CACCGAGATCTACAC TCTTTCCCTACACGA CGCTCTTC CGATCTTAGTTTAC GCAGACTATCTTTC TAG | Standard desalt | For use with piggyBac SRTs |
| OM-PB-ATC (SEQ ID NO: 24) | AATGATACGGCGAC CACCGAGATCTACAC TCTTTCCCTACACGA CGCTCTTC CGATCTATCTTTAC GCAGACTATCTTTC TAG | Standard desalt | For use with piggyBac SRTs |
| OM-PB-CGT (SEQ ID NO: 25) | AATGATACGGCGAC CACCGAGATCTACAC TCTTTCCCTACACGA CGCTCTTC CGATCTCGTTTTAC GCAGACTATCTTTC TAG | Standard desalt | For use with piggyBac SRTs |
| OM-PB-GCA (SEQ ID NO: 26) | AATGATACGGCGAC CACCGAGATCTACAC TCTTTCCCTACACGA CGCTCTTC CGATCTGCATTTAC GCAGACTATCTTTC TAG | Standard desalt | For use with piggyBac SRTs |
| OM-SB-ACG (SEQ ID NO: 27) | AATGATACGGCGAC CACCGAACACTCTTT CCCTACACGACGCT CTTCCGATC TACGTAAGTGTATG TAAACTTCCGACTT CAA | Standard desalt | For use with Sleeping Beauty SRTs |
| OM-SB-CTA (SEQ ID NO: 28) | AATGATACGGCGAC CACCGAACACTCTTT CCCTACACGACGCT CTTCCGATC | Standard desalt | For use with Sleeping Beauty SRTs |

TABLE 2-continued

Oligonucleotides referenced in this work.

| Primer | Primer Sequence | Purification | Notes |
|---|---|---|---|
| | TCTATAAGTGTATGT AAACTTCCGACTTC AA | | |
| OM-SB-GAT (SEQ ID NO: 29) | AATGATACGGCGAC CACCGAACACTCTTT CCCTACACGACGCT CTTCCGATC TGATTAAGTGTATG TAAACTTCCGACTT CAA | Standard desalt | For use with Sleeping Beauty SRTs |
| OM-SB-TGC (SEQ ID NO: 30) | AATGATACGGCGAC CACCGAACACTCTTT CCCTACACGACGCT CTTCCGATC TTGCTAAGTGTATG TAAACTTCCGACTT CAA | Standard desalt | For use with Sleeping Beauty SRTs |
| OM-SB-TAG (SEQ ID NO: 31) | AATGATACGGCGAC CACCGAACACTCTTT CCCTACACGACGCT CTTCCGATC TTAGTAAGTGTATG TAAACTTCCGACTT CAA | Standard desalt | For use with Sleeping Beauty SRTs |
| OM-SB-ATC (SEQ ID NO: 32) | AATGATACGGCGAC CACCGAACACTCTTT CCCTACACGACGCT CTTCCGATC TATCTAAGTGTATGT AAACTTCCGACTTC AA | Standard desalt | For use with Sleeping Beauty SRTs |
| OM-SB-CGT (SEQ ID NO: 33) | AATGATACGGCGAC CACCGAACACTCTTT CCCTACACGACGCT CTTCCGATC TCGTTAAGTGTATG TAAACTTCCGACTT CAA | Standard desalt | For use with Sleeping Beauty SRTs |
| OM-SB-GCA (SEQ ID NO: 34) | AATGATACGGCGAC CACCGAACACTCTTT CCCTACACGACGCT CTTCCGATC TGCATAAGTGTATG TAAACTTCCGACTT CAA | Standard desalt | For use with Sleeping Beauty SRTs |
| N7 indexed primer (SEQ ID NO: 35 [index] SEQ ID NO: 36) | CAAGCAGAAGACG GCATACGAGAT[index] GTCTCGTGGGCTC GG | Standard desalt | Uniquely identifies each bulk RNA calling card library in conjunction with barcoded transposon primer |
| 10x_TSO (SEQ ID NO: 37) | AAGCAGTGGTATCA ACGCAGAGTACATr GrGrG | Standard desalt | For continuing 10x scRNA-seq prep after splitting first RT product in half |
| Bio_Illumina_Seq1_ scCC_10X_3xPT (SEQ ID NO: 38) | /5Phos/ACACTCTTT CCC/iBiodT/ACACGA CGCTCTTCCGA*T*C *T | HPLC | Single cell calling card primer for use with 10x Chromium 3' v2 kit |
| Bio_Long_PB_ LTR_3xPT (SEQ ID NO: 39) | /5Phos/GCGTCAATT TTACGCAGAC/ iBiodT/ ATCTTTC*T*A*G | HPLC | Single cell calling card primer for use with piggyBac SRTs |

TABLE 2-continued

Oligonucleotides referenced in this work.

| Primer | Primer Sequence | Purification | Notes |
|---|---|---|---|
| scCC_P5_adapter (SEQ ID NO: 40) | AATGATACGGCGAC CACCGAGATCTTCAC TCATTCCACACGACT CCTTGCCA GTCTC*T | Standard desalt | Adapter for scCC (needs to be pre-annealed with scCC_P7_adapter) |
| scCC_P7_adapter (SEQ ID NO: 41 [index]SEQ ID NO: 42) | /5Phos/GAGACTGGC AAGTACACGTCGCAC TCACCATGA[index] ATCTC GTATGCCGTCTTCT GCTTG | Standard desalt | Adapter for scCC (needs to be pre-annealed with scCC_P5_adapter) |
| scCC_P5_primer (SEQ ID NO: 43) | AATGATACGGCGAC CACCGAGATC | Standard desalt | For final scCC library PCR |
| scCC_P7_primer (SEQ ID NO: 44) | CAAGCAGAAGACG GCATACGAGAT | Standard desalt | For final scCC library PCR |
| scCC_PB_Custom Read2 (SEQ ID NO: 45) | CGTGTAGGGAAAGA GTGTGCGTCAATTT TACGCAGACTATCT TTCTAG | PAGE | For custom sequencing of piggyBac scCC libraries; read 2 should begin with GGTTAA |
| scCC_CustomInd ex1 (SEQ ID NO: 46) | GAGACTGGCAAGTA CACGTCGCACTCAC CATGA | PAGE | For custom sequencing of scCC libraries |

After transferring to ice and letting rest for 1 minute, 4 µl 5× Maxima RT Buffer, 1 µl RNaseOUT (Thermo Fisher #10777019), and 1 µl of 1:1 Maxima H Minus Reverse Transcriptase diluted in 1×RT Buffer (100 U) were added. The solution was mixed by pipetting and incubated at 50° C. for 1 hour followed by heat inactivation at 85° C. for 10 minutes. Finally, the mixture was digested with 1 µl RNaseH (NEB #M0297S) at 37° C. for 30 minutes. cDNA was stored at −20° C.

Amplification of Self-Reporting Transcripts from Bulk RNA

The PCR conditions for amplifying self-reporting transcripts (i.e., transcripts derived from self-reporting transposons) involved mixing 1 µl cDNA template with 12.5 µl Kapa HiFi HotStart ReadyMix (Kapa Biosystems #KK2601), 0.5 µl 25 µM SMART primer, and either 1 µl of 25 µM SRT_PAC_F1 primer (in the case of puromycin selection) or 0.5 µl of 25 µM SRT_tdTomato_F1 primer (in the case of tdTomato screening). The mixture was brought up to 25 µl with ddH$_2$O. Thermocycling parameters were as follows: 95° C. for 3 minutes; 20 cycles of: 98° C. for 20 seconds–65° C. for 30 seconds–72° C. for 5 minutes; 72° C. for 10 minutes; hold at 4° C. forever. As a control, cDNA quality can be assessed with exon-spanning primers for R-actin (see TABLE 2 for examples of human primers) under the same thermocycling settings.

PCR products were purified using AMPure XP beads (Beckman Coulter #A63880). 12 µl of resuspended beads were added to the 25 µl PCR product and mixed homogenously by pipetting. After a 5-minute incubation at room temperature, the solution was placed on a magnetic rack for 2 minutes. The supernatant was aspirated and discarded. The pellet was washed twice with 200 µl of 70% ethanol (incubated for 30 seconds each time), discarding the supernatant each time. The pellet was left to dry at room temperature for 2 minutes. To elute, 20 µl ddH$_2$O was added to the pellet, the pellet was resuspended by pipetting, and the mixture was incubated at room temperature for 2 minutes, and placed on a magnetic rack for one minute. Once clear, the solution was transferred to a clean 1.5 ml tube. DNA concentration was measured on the Qubit 3.0 Fluorometer (Thermo Fisher #Q33216) using the dsDNA High Sensitivity Assay Kit (Thermo Fisher #Q32851).

Generation of Bulk RNA Calling Card Libraries

Calling card libraries from bulk RNA were generated using the Nextera XT DNA Library Preparation Kit (Illumina #FC-131-1024). One nanogram of PCR product was resuspended in 5 µl ddH$_2$O. To this mixture 10 µl Tagment DNA (TD) Buffer and 5 µl Amplicon Tagment Mix (ATM) were added. After pipetting to mix, the solution was incubated in a thermocycler preheated to 55° C. The tagmentation reaction was halted by adding 5 µl Neutralization Tagment (NT) Buffer and was kept at room temperature for 5 minutes. The final PCR was set up by adding 15 µl Nextera PCR Mix (NPM), 8 µl ddH$_2$O, 1 µl of 10 µM transposon primer (e.g., OM-PB-NNN) and 1 µl Nextera N7 indexed primer. The transposon primer anneals to the end of the transposon terminal repeat-piggyBac, in the case of OM-PB primers, or Sleeping Beauty, in the case of OM-SB primers- and contains a 3 base pair barcode sequence. Every N7 primer contains a unique index sequence that is demultiplexed by the sequencer. Each replicate was assigned a unique combination of barcoded transposon primer and indexed N7 primer, enabling precise identification of each library's sequencing reads.

The final PCR was run under the following conditions: 95° C. for 30 seconds; 13 cycles of: 95° C. for 10 seconds– 50° C. for 30 seconds–72° C. for 30 seconds; 72° C. for 5 minutes; hold at 4° C. forever. After PCR, the final library was purified using 30 µl (0.6×) AMPure XP beads, as described above. The library was eluted in 11 µl ddH$_2$O and quantitated on an Agilent TapeStation 4200 System using the High Sensitivity D1000 ScreenTape (Agilent #5067-5584 and #5067-5585).

Sequencing and Analysis of Bulk RNA Calling Card Libraries

Multiple calling card libraries were pooled together for sequencing on the Illumina HiSeq 2500 platform. To increase the complexity of the library, PhiX was added at a final loading concentration of 50%. Reads were demultiplexed by the N7 index sequences added during the final PCR. Read 1 began with the 3 base pair barcode followed by the end of the transposon terminal repeat, culminating with the insertion site motif (TTAA in the case of piggyBac; TA in the case of Sleeping Beauty) before entering the genome. piggyBac reads were checked for exact matches to the barcode, transposon sequence, and insertion site at the beginning of reads before being hard trimmed using cutadapt with the following settings: —g "^NNNTTTACGC-AGACTATCTTTCTAGGGTTAA" (SEQ ID NO: 47)—minimum-length 1—discard-untrimmed—e 0—no—indels, where NNN is replaced with the primer barcode. Sleeping Beauty libraries were trimmed with the following settings: —g "^NNNTAAGTGTATGTAAACTTCCGACT-TCAACTGTA" (SEQ ID NO: 48)—minimum-length 1—discard—untrimmed—e 0—no-indels. Reads passing this filter were then trimmed of any trailing Nextera adapter sequence, again using cutadapt and the following settings: —a "CTGTCTCTTATACACATCTCCGAGCCCACGA-GACTNNNNNNNNNNNTCTCGT ATGCCGTCTTCTGCTTG" (SEQ ID NO: 49)—minimum-length 1. The remaining reads were aligned to the human genome (build hg38) with Novoalign 3 (Novocraft Technologies) and the following settings: —n 40 —o SAM —o SoftClip. Aligned reads were validated by confirming that they mapped adjacent to the insertion site motif. Successful reads were then converted to calling card format (.ccf) visualized on the WashU Epigenome Browser v46.

In Vitro Single Cell Calling Card Experiments

N2a and K562 cells were cultured and transfected identically as HCT-116 cells, with the following exceptions: K562 cells were grown in RPMI 1640 Medium (Gibco #11875-085); for K562 cells, Neon electroporation settings were—pulse voltage: 1,450 V; pulse width: 10 ms; pulse number: 3; for N2a cells, Neon electroporation settings were—pulse voltage: 1,050 V; pulse width: 30 ms; pulse number: 2. For N2a cells, one replicate ($2 \times 10^6$ cells) was transfected with 5 µg PB-SRT-Puro and 5 µg HyPBase, while another replicate was transfected with 5 µg PB-SRT-Puro only. For K562 cells, 4 replicates received both plasmids and one received the SRT alone. After 1 week of selection, N2a or K562 cells were mixed with transfected HCT-116 cells and then underwent single cell RNA-seq library preparation. For the species mixing experiment, cells were classified as either human or mouse if at least 80% of self-reporting transcripts in that cell mapped to the human or mouse genome, respectively.

Single Cell RNA-Seq Library Preparation

Single cell RNA-seq libraries were prepared using 10× Genomics' Chromium Single Cell 3' Library and Gel Bead Kit (v2 chemistry; #120267). Each replicate was targeted for recovery of 6,000 cells. Library preparation followed a modified version of the manufacturer's protocol. The Single Cell Master Mix was prepared without RT Primer and replaced by an equivalent volume of Low TE Buffer. GEM generation and GEM-RT incubation proceeded as instructed. At the end of Post GEM-RT cleanup, 36.5 µl Elution Solution I was added and 36 µl of the eluted sample was transferred to a new tube (instead of 35.5 µl and 35 µl, respectively). The eluate was split into two 18 µl aliquots and kept at $-20°$ C. until ready for further processing. One fraction was kept for single cell calling cards library preparation, while the other half was further processed into a single cell RNA-seq library.

The RT Primer sequence was then added to the products in the scRNA-seq aliquot. An RT master mix was created by adding 20 µl of Maxima 5×RT Buffer, 20 µl of 20% w/v Ficoll PM-400 (GE Healthcare #17030010), 10 µl of 10 mM dNTPs (Clontech #639125), 2.5 µl RNase Inhibitor (Lucigen), and 2.5 µl of 100 µM 10x_TSO. To this solution 18 µl of the first RT product and 22 µl of ddH$_2$O were added. Finally, 5 µl Maxima H Minus Reverse Transcriptase was added, mixed by flicking, and centrifuged briefly. This reaction was incubated at 25° C. for 30 minutes followed by 50° C. for 90 minutes and heat inactivated at 85° C. for 5 minutes. The solution was purified using DynaBeads MyOne Silane (Thermo Fisher #37002D) following 10× Genomics' instructions, beginning at "Post GEM-RT Cleanup—Silane DynaBeads" step D. The remainder of the single cell RNA-seq protocol, including purification, amplification, fragmentation, and final library amplification, followed manufacturer's instructions.

Single Cell Calling Cards Library Preparation

To amplify self-reporting transcripts from single cell RNA-seq libraries, 9 µl of RT product (the other half was kept in reserve) was added to 25 µl Kapa HiFi HotStart ReadyMix and 15 µl ddH$_2$O. A PCR primer cocktail was then prepared comprising 5 µl of 100 µM Bio_llumina_Seq1_scCC_10×_3×PT primer, 5 µl of 100 µM Bio_Long_PB_LTR_3×PT, and 10 µl of 10 mM Tris-HCl, 0.1 mM EDTA buffer (IDT #11-05-01-13). One µl of this cocktail was added to the PCR mixture and placed in a thermocycler (Eppendorf MasterCycler Pro). Thermocycling settings were as follows: 98° C. for 3 minutes; 20-22 cycles of 98° C. for 20 seconds–67° C. for 30 seconds–72° C. for 5 minutes; 72° C. for 10 minutes; 4° C. forever. PCR purification was performed with 30 µl AMPure XP beads (0.6× ratio) as described previously. The resulting library was quantitated on an Agilent TapeStation 4200 System using the High Sensitivity D5000 ScreenTape (Agilent #5067-5592 and #5067-5593).

Single cell calling card library preparation was performed using the Nextera Mate Pair Sample Prep Kit (Illumina #FC-132-1001) with modifications to the manufacturer's protocol. The library was circularized by bringing 300 fmol (approximately 200 ng) of DNA up to a final volume of 268 µl with ddH$_2$O, then adding 30 µl Circularization Buffer 10× and 2 µl Circularization Ligase (final concentration: 1 nM). This reaction was incubated overnight (12-16 hours) at 30° C. After removal of linear DNA (following manufacturer's instructions), the library on a Covaris E220 Focused-ultrasonicator was sheared with the following settings-peak power intensity: 200; duty factor: 20%; cycles per burst: 200; time: 40 seconds; temperature: 6° C.

The library preparation proceeded per manufacturer's instructions until adapter ligation. Custom adapters were designed (see e.g., TABLE 2) so that the standard Illumina sequencing primers would not interfere with the library. Adapters were prepared by combining 4.5 µl of 100 µM scCC_P5_adapter, 4.5 µl of 100 µM scCC_P7_adapter, and 1 µl of NEBuffer 2 (NEB #B7002S), then heating in a thermocycler at 95° C. for 5 minutes, then holding at 70° C. for 15 minutes, then ramping down at 1% until it reached 25° C., holding at the temperature for 5 minutes, before keeping at 4° C. forever. One µl of this custom adapter mix was used in place of the manufacturer's recommended DNA Adapter Index. The ligation product was cleaned per manufacturer's instructions. For the final PCR, the master mix was created by combining 20 µl Enhanced PCR Mix with 28 µl of ddH$_2$O and 1 µl each of 25 µM scCC_P5_primer and 25 µM scCC_P7_primer). This was then added to the streptavidin bead-bound DNA and amplified under the following conditions: 98° C. for 30 seconds; 15 cycles of: 98° C. for 10 seconds–60° C. for 30 seconds–72° C. for 2 minutes; 72° C. for 5 minutes; 4° C. forever. All of the PCR supernatant was transferred to a new tube and purified with 35 µl (0.7×) AMPure XP beads following manufacturer's instructions. The final library was eluted in 25 µl Elution Buffer (QIAGEN #19086) and quantitated on an Agilent TapeStation 4200 System using the High Sensitivity D1000 ScreenTape.

Sequencing and Analysis of scRNA-Seq Libraries scRNA-seq libraries were sequenced on either Illumina HiSeq 2500 or NovaSeq S1 machines. Reads were analyzed using 10× Genomics' cellranger 2.1.0 with the following settings: —expect-cells=6000—chemistry=SC3Pv2—local-cores=16—localmem=30. The digital gene expression matrices from 10× were then further processed with scanpy 1.3.7 for identification of highly variable genes, dimensionality reduction, and Louvain clustering. The species-mixing analysis was analyzed using Drop-seq_tools 1.11.

Sequencing and Analysis of scCC Libraries scCC libraries were sequenced on Illumina NextSeq 500 machines (v2 Reagent Cartridges) with 50% PhiX. The standard Illumina primers were used for read 1 and index 2 (BP10 and BP14, respectively), and custom primers for read 2 and index 1 (see e.g., TABLE 2). Read 1 sequenced the cell barcode and unique molecular index of each self-reporting transcript. Read 2 began with GGTTAA (end of the piggyBac terminal repeat and insertion site motif) before continuing into the genome. Reads containing this exact hexamer were trimmed using cutadapt with the following settings: —g "^GGTTAA"—minimum-length 1—discard-untrimmed—e 0—no-indels. Reads passing this filter were then trimmed of any trailing P7 adapter sequence, again using cutadapt and with the following settings: —a "AGAGACTGGCAAGTACACGTCGCACTCACCATGANNNNNNNNNNATCTCGTATGCCGTCTTCTGCTTG" (SEQ ID NO: 50)—minimum-length 1. Reads passing these filters were aligned using 10× Genomics' cellranger with the following settings: —expect-cells=6000—nosecondary—chemistry=SC3Pv2—local-cores=16—localmem=30. This workflow also managed barcode validation and collapsing of UMIs. Aligned reads were validated by verifying that they mapped adjacent to TTAA tetramers. Reads were then converted to calling card format (.ccf, see above). Finally, to minimize the presence of intermolecular artifacts, it was required that each insertion must have been tagged by at least two different UMIs. The set of validated cell barcodes from each scRNA-seq library was used to demultiplex library-specific barcoded insertions from the scCC data. This approach requires no shared cell barcodes between scCC (and scRNA-seq) libraries. As a result, insertions from non-unique cell barcodes were excluded, which represented a very small number of total cells lost (<1% per multiplexed library).

Peak Calling

Peaks were called in calling card data using Bayesian blocks, a noise-tolerant algorithm for segmenting discrete, one-dimensional data, using the astroML 0.3 implementation. Bayesian blocks segments the genome into non-overlapping blocks where the density of calling card insertions is uniform. By comparing the segmentation against a background model, Poisson statistics were used to assess whether a given block shows statistically significant enrichment for insertions. Let $B=\{b_1, b_2, \ldots b_n\}$ represent the set of blocks found by performing Bayesian block segmentation on all insertions from a TF-directed experiment (e.g., SP1-PBase). For each block $b_i$, let $x_i$ be the number of insertions in that block in the TF-directed experiment. Similarly, let $y_i'$ be the number of insertions in that block in the undirected experiment (e.g., PBase) normalized to the total number of insertions found in the TF-directed experiment. Then, for each block the Poisson p-value of observing at least $x_i$ insertions assuming a Poisson distribution with expectation $y_i'$: $P(k \geq x_i | \lambda = y_i')$ was calculated. All blocks that were significant beyond a particular p-value threshold were accepted.

For bulk analysis of SP1-PBase and SP1-HyPBase insertions, a pseudocount of 0.1 was added to all blocks and p-value cutoffs of $10^{-6}$ and $10^{-22}$ were used, respectively. For single cell analysis of SP1-HyPBase insertions, a pseudocount of 1 was added to all blocks and a p-value cutoff of $10^{-9}$ was used. All three of these values were beyond a Bonferroni-corrected α of 0.05. Peak calls were polished by merging statistically-significant blocks that were within 250 bases of each other and by aligning block edges to coincide with TTAAs.

To identify BRD4 binding sites from undirected piggyBac insertions, those insertions were segmented using Bayesian blocks. For each block $b_i$, $x_i$ denotes the number of undirected insertions in that block. $x_i'$, the expected number of insertions in block $b_i$ was also calculated, assuming piggyBac insertions were distributed uniformly across the genome. This was done by dividing the total number of mappable TTAAs in the genome by the total number of undirected insertions, then multiplying this value by the number of mappable TTAAs in block $b_i$. Then, for each block the Poisson p-value $P(k \geq x_i | \lambda = x_i')$ was calculated. All blocks that were significant beyond a particular p-value threshold were accepted. Finally, statistically significant blocks were merged that were within 12,500 bases of each other.

For the bulk PBase and HyPBase analysis, p-value cutoffs of $10^{-30}$ and $10^{-62}$ were used, respectively. For both in vitro and in vivo single cell HyPBase analyses, a p-value cutoff of $10^{-9}$ was used. To call differentially-bound loci between upper and lower cortical layer neurons, the same framework as described above for SP1 was used but with reciprocal enrichment analyses where the upper layer insertions were used as the "experiment" track and the lower layer insertions were used as the "control" track, and vice-versa. Here again a p-value cutoff of $10^{-9}$ was used.

SP1 Binding Analysis in HCT-116 Cells

The SP1 peak calls were compared to a publicly-available ChIP-seq dataset as well as an input control file (see e.g., TABLE 3).

TABLE 3

External ChIP-seq datasets referenced in this work

| Target | Cell type | Source | Accession | Control File | DOI |
|---|---|---|---|---|---|
| SP1 | HCT-116 | ENCODE | ENCFF000PCT | ENCFF000PBO | |
| BRD4 | HCT-116 | Publication | SRR2481799 | SRR2481800 | 0.1172/ JCI83265 |

TABLE 3-continued

External ChIP-seq datasets referenced in this work

| Target | Cell type | Source | Accession | Control File | DOI |
| --- | --- | --- | --- | --- | --- |
| H3K27ac | HCT-116 | ENCODE | ENCFF082JPN, ENCFF176BXC | ENCFF048ZOQ, ENCFF827YXC | |
| H3K4me1 | HCT-116 | ENCODE | ENCFF088BWP, ENCFF804MJI | ENCFF048ZOQ, ENCFF827YXC | |
| H3K9me3 | HCT-116 | ENCODE | ENCFF578MDZ, ENCFF033XOG | ENCFF048ZOQ, ENCFF827YXC | |
| H3K27me3 | HCT-116 | ENCODE | ENCFF281SBT, ENCFF124GII | ENCFF048ZOQ, ENCFF827YXC | |
| CTCF | HCT-116 | ENCODE | ENCFF000OZC | ENCFF000PBO | |
| H3K9me2 | HCT-116 | ENCODE | ENCFF760OZN, ENCFF565FDP | ENCFF048ZOQ, ENCFF827YXC | |
| H3K36me3 | HCT-116 | ENCODE | ENCFF850EAH, ENCFF312RKB | ENCFF048ZOQ, ENCFF827YXC | |
| H4K20me1 | HCT-116 | ENCODE | ENCFF070JDY, ENCFF334HHB | ENCFF048ZOQ, ENCFF827YXC | |
| H3K4me2 | HCT-116 | ENCODE | ENCFF936MMN, ENCFF937OOL | ENCFF048ZOQ, ENCFF827YXC | |
| H3K4me3 | HCT-116 | ENCODE | ENCFF183OZI, ENCFF659FPR | ENCFF048ZOQ, ENCFF827YXC | |
| H3K9ac | HCT-116 | ENCODE | ENCFF408RRT | ENCFF413RQG | |
| H3K79me2 | HCT-116 | ENCODE | ENCFF865KPW, ENCFF947YPU | ENCFF048ZOQ, ENCFF827YXC | |
| BRD4 | K562 | ENCODE | ENCFF335PHG | ENCFF000BWK | |
| H3K27ac | K562 | ENCODE | ENCFF000BXH | ENCFF000BWK | |
| H3K27ac | Mouse cortex | Publication | SRR6129714 | SRR6129695 | 0.1016/j.cell.2017.09.047 |

See below for more details on aligning and analyzing ChIP-seq data. A list of unique TSSs was collated by taking the 5'-most coordinates of RefSeq Curated genes in the hg38 build (UCSC Genome Browser). A list of CpG islands in HCT-116 cells and their methylation statuses were derived from previously-published Methyl-seq data. The liftOver tool (UCSC) was used to convert coordinates from hg18 to hg38. Enrichment in SP1-directed insertions was tested at TSSs, CpG islands, and unmethylated CpGs with the G test of independence. For motif discovery used MEME-ChIP 4.11.2 was used with a dinucleotide shuffled control and the following settings: —dna-nmeme 600—seed 0—ccut 250—meme-mod zoops —meme-minw 4—meme-nmotifs 5.

BRD4 Sensitivity, Specificity, and Precision Analysis in HCT-116 Cells

A published BRD4 ChIP-seq dataset was used to identify BRD4-bound super-enhancers in HCT-116 cells, following previously-described methods. Peaks were first called using MACS 1.4.1 at p-<$10^{-9}$, then this list was fed into ROSE 0.1. Artifactual loci less than 2,000 bp in size were discarded, yielding a final list of 162 super-enhancers. To evaluate sensitivity, bedtools 2.27.1 was used to ask what fraction of piggyBac peaks, at various p-value thresholds, overlapped the set of BRD4-bound super-enhancers. To measure specificity, a list of regions predicted to be insignificantly enriched (p>0.1) was created for BRD4 ChIP-seq signal. Bases from this region were then sampled such that the distribution of peak sizes was identical to that of the 162 super-enhancers. Sampling to 642× coverage was then performed, sufficient to cover each base with one peak, on average. The fraction of the piggyBac peaks that overlapped these negative peaks was then determined and subtracted from 1 to obtain specificity. Finally, precision, or positive predictive value, was calculated by dividing the total number of detected super-enhancer peaks by the sum of the super-enhancer peaks and the false positive peaks.

Downsampling and Replication Analysis

When performing downsampling analyses on calling card insertions, insertions were randomly sampled without replacement and in proportion to the number of reads supporting each insertion. Peaks were called on the downsampled insertions at a range of p-value cutoffs. Linear interpolation was performed using numpy 1.15 and visualized using matplotlib 3.0. Replication was assessed by splitting calling card insertions into two, approximately equal, files based on their barcode sequences. Each new file was treated as a single biological experiment. For each peak called from the joint set of all insertions, the number of normalized insertions (insertions per million mapped insertions, or IPM) was plotted in one replicate on the x-axis and the other replicate on y-axis.

ChIP-Seq and Chromatin State Analyses

Raw reads were aligned using Novoalign with the following settings for single-end datasets: —o SAM—o SoftClip, while paired-end datasets were mapped with the additional flag —i PE 200-500. To calculate and visualize the fold enrichment in ChIP-seq signal at calling card peaks, deeptools 3.0.1 was used. Significant mean enrichment was tested for in BRD4 ChIP-seq signal at piggyBac peaks over randomly shuffled control peaks with the Kolmogorov-Smirnov test. Chromatin state analysis was performed using ChromHMM 1.15 as previously described. For each chromatin state, mean and standard deviation of the rate of normalized insertions per kilobase (IPM/kb) were plotted.

SRT-tdTomato Fluorescence Validation

To test the fluorescence properties of the SRT-tdTomato construct, K562 cells were transfected as previously described with either 1 μg of PUC19 plasmid; 0.5 μg of PB-SRT-tdTomato plasmid and 0.5 μg PUC19; 0.5 μg of PB-SRT-tdTomato and 0.5 μg PBase plasmid; and 0.5 μg of PB-SRT-tdTomato and 0.5 μg HyPBase plasmid. Cells were allowed to expand for 8 days, after which fluorescence activity was assayed on an Attune NxT Flow Cytometer (Thermo Fisher) with an excitation wavelength of 561 nm. Flow cytometery data were visualized using FlowCal 1.2.0.

Bulk RNA calling cards were assayed on HEK293T cells transfected with SRT-tdTomato with or without HyPBase plasmid. While these cells were not sorted based on fluorescence activity, the SRT library from cells transfected with both SRT and transposase were more complex and contained many more insertions than the library from cells receiving SRT alone (see e.g., FIG. 9A).

In Vivo Single Cell Calling Cards Experiments

All mouse experiments were done following procedures previously described. In brief, the PB-SRT-tdTomato and HyPBase constructs were cloned into AAV vectors. The Hope Center Viral Vectors Core at Washington University in St. Louis packaged each construct in AAV9 capsids. Titers for each virus ranged between $1.1 \times 10^{13}$ and $2.2 \times 10^{13}$ viral genomes/ml. Equal volumes of each virus were mixed and intracranial cortical injections of the mixture into newborn wild-type C57BL/6J pups (P0-2) were performed. As a gating control, one litter-matched animal was injected with AAV9-PB-SRT-tdTomato only. After 2 to 4 weeks, the mice were sacrificed and the cortex (8 libraries) or hippocampus (1 library) dissected.

Tissues were dissociated to single suspensions following a modification of previously published methods. Samples were incubated in a papain solution containing Hibernate-A (Gibco #A1247501) with 5% v/v trehalose (Sigma-Aldrich #T9531), 1×B-27 Supplement (Gibco #17504044), 0.7 mM EDTA (Corning #36-034-CI), 70 µM 2-mercaptoethanol (Gibco #21985023), and 2.8 mg/ml papain (Worthington Chemical Corporation #LS003118). After incubation at 37° C., cells were treated with DNaseI (Worthington Chemical Corporation #NC9924263), triturated through increasingly narrow fire-polished pipettes, and passed through a 40-micron filter prewetted with resuspension solution: Hibernate-A containing 5% v/v trehalose, 0.5% Ovomucoid Trypsin Inhibitor (Worthington Chemical Corporation #NC9931428), 0.5% Bovine Serum Albumin (BSA; Sigma-Aldrich #A9418), 33 µg/ml DNaseI, and 1×B-27 Supplement. The filter was washed with 6 ml of resuspension solution. The resulting suspension was centrifuged for 4 minutes at 250 g. The supernatant was discarded. The pellet was then resuspended in 2 ml of resuspension solution and resuspended by gentle pipetting.

Subcellular debris was eliminated using gradient centrifugation. A working solution of 30% w/w OptiPrep Density Gradient Medium (Sigma-Aldrich #D1556) mixed with an equal volume of 1×Hank's Balanced Salt Solution (HBSS; Gibco #14185052) with 0.5% BSA was prepared. Solutions of densities 1.057, 1.043, 1.036, and 1.029 g/ml were then prepared by combining the working solution with resuspension solution at ratios of 0.33:0.67, 0.23:0.77, 0.18:0.82, and 0.13:0.87, respectively. 1 ml aliquots of each solution were layered in a 15 ml conical tube beginning with the densest solution on the bottom. The cell suspension was added last to the tube and centrifuged for 20 minutes at 800 g at 12° C. The top layer was then aspirated and purified cells were isolated from the remaining layers. These cells were then resuspended in FACS buffer: 1×HBSS, 2 mM $MgCl_2$ (Sigma-Aldrich #M4880), 2 mM $MgSO_4$ (Sigma-Aldrich #M2643), 1.25 mM $CaCl_2$ (Sigma-Aldrich #C7902), 1 mM D-glucose (Sigma-Aldrich #G7021), 0.02% BSA, and 5% v/v trehalose. Cells were centrifuged for 4 minutes at 250 g, the supernatant was discarded, and the pellet was resuspended in FACS buffer by gentle pipetting.

Cells were then sorted based on fluorescence activity. As a gating control, w cells from cortices injected with AAV9-PB-SRT-tdTomato only were analyzed. Cells were then collected from brains transfected with AAV9-PB-SRT-tdTomato and AAV9-HyPBase whose fluorescence values exceed the gate. After sorting, cells were centrifuged for 3 minutes at 250 g. The supernatant was discarded and cells were resuspended in FACS buffer at a concentration appropriate for 10× Chromium 3' scRNA-seq library preparation.

Example 3: Use of the Line 1 (L1) Transposon for Calling Cards

Figure 18:
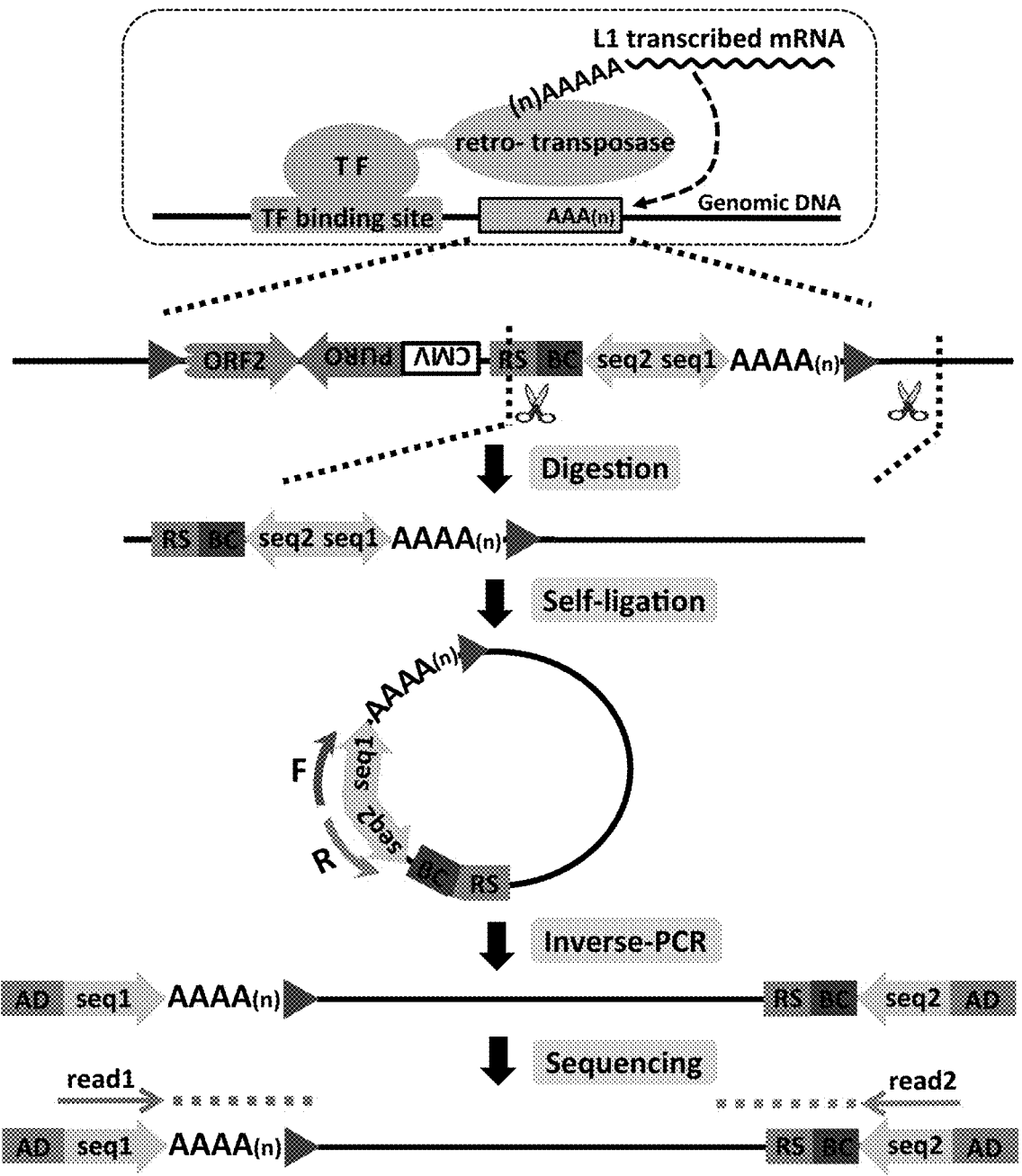
FIG. 18 is a schematic depicting the calling cards method adapted for use with the L1 retrotransposon with DNA recovery. By fusing a retro-transposase to a transcription factor (TF), the TF is endowed with the ability to insert retrotransposons into the genome. In this embodiment, the TF is fused to ORF2 of the L1 transposon. ORF2 then cuts genomic DNA at TF binding sites and copies the RNA transposon via its reverse transcriptase activity to insert a DNA copy of the transposon in the genome. Transposon locations can be mapped by performing inverse PCR followed by Illumina sequencing.
Figure 19:
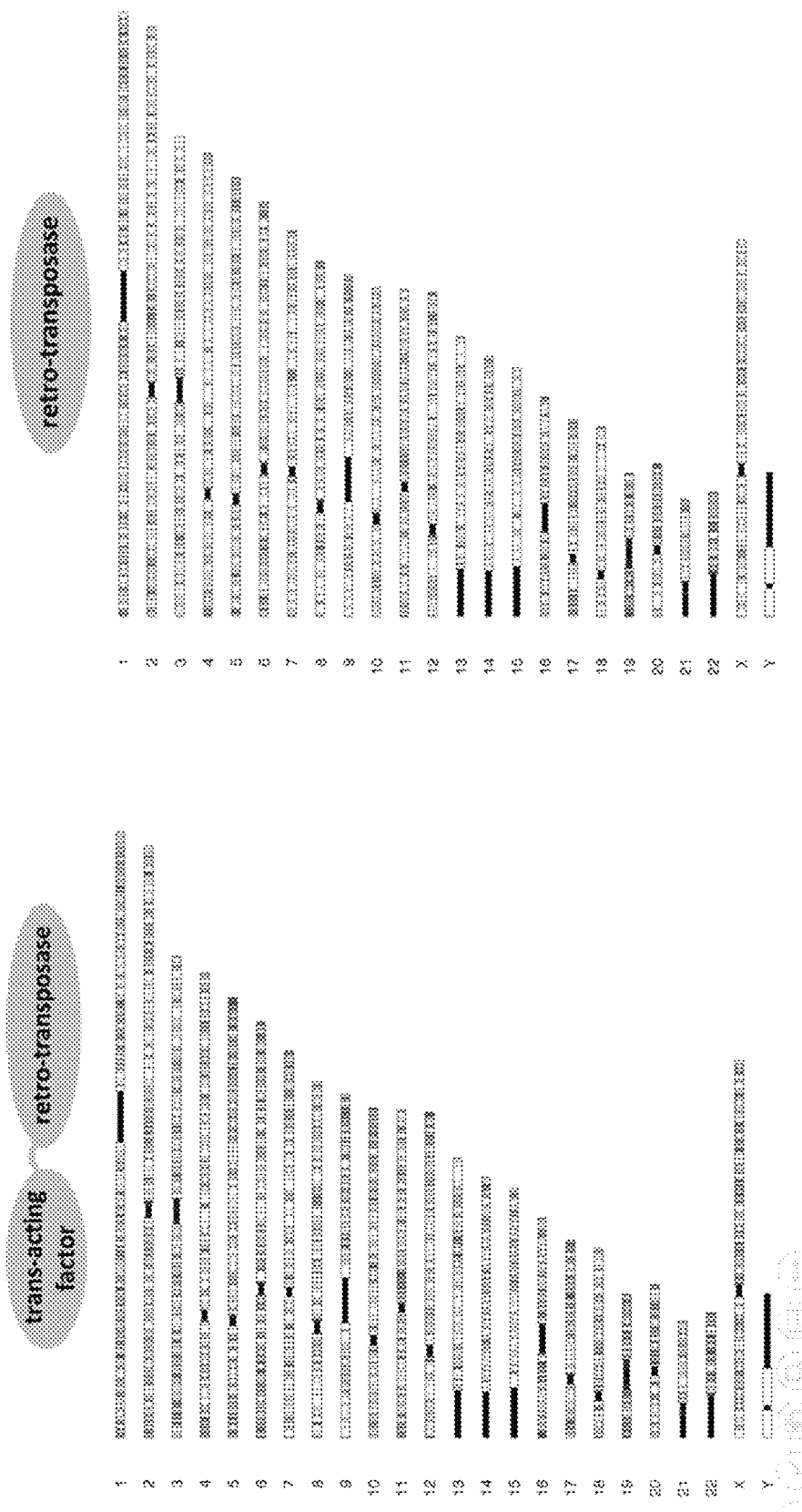
FIG. 19 is a genome wide view of LINE 1 insertions that were either directed by SP1 or undirected. These insertions were mapped using the protocol described in FIG. 18.
Figure 22:
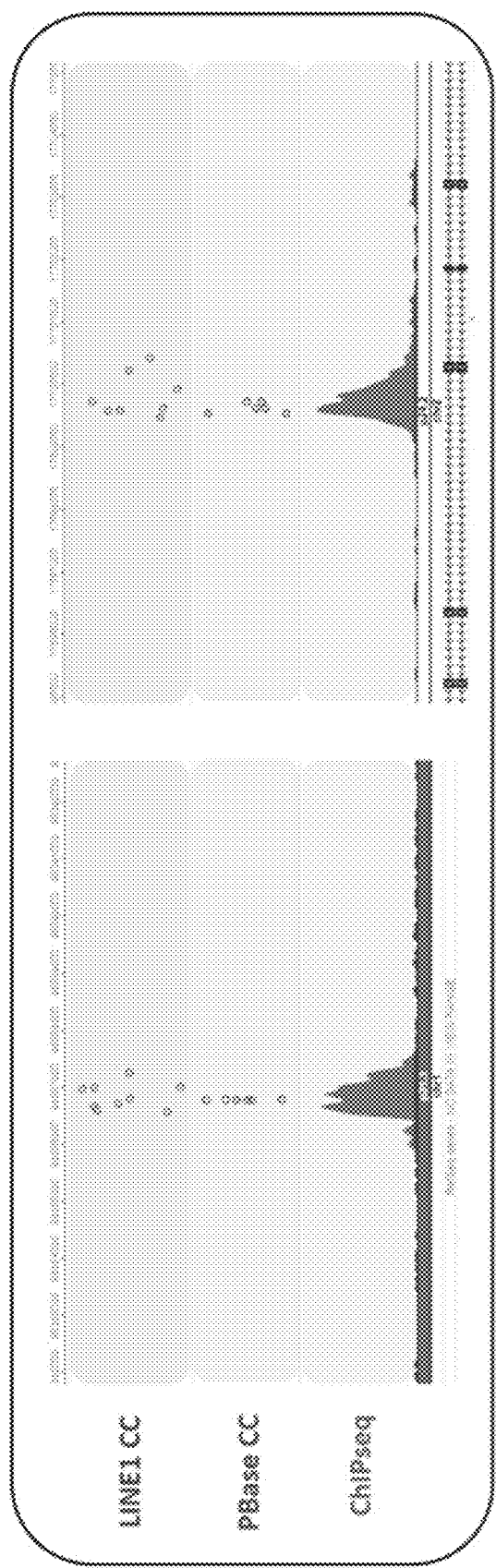
FIG. 22 provides an example of a known Sp1 binding site, demonstrating the concordance of ChIPseq signal, L1 calling cards directed by Sp1, and piggyBac calling cards directed by Sp1.
Figure 24:
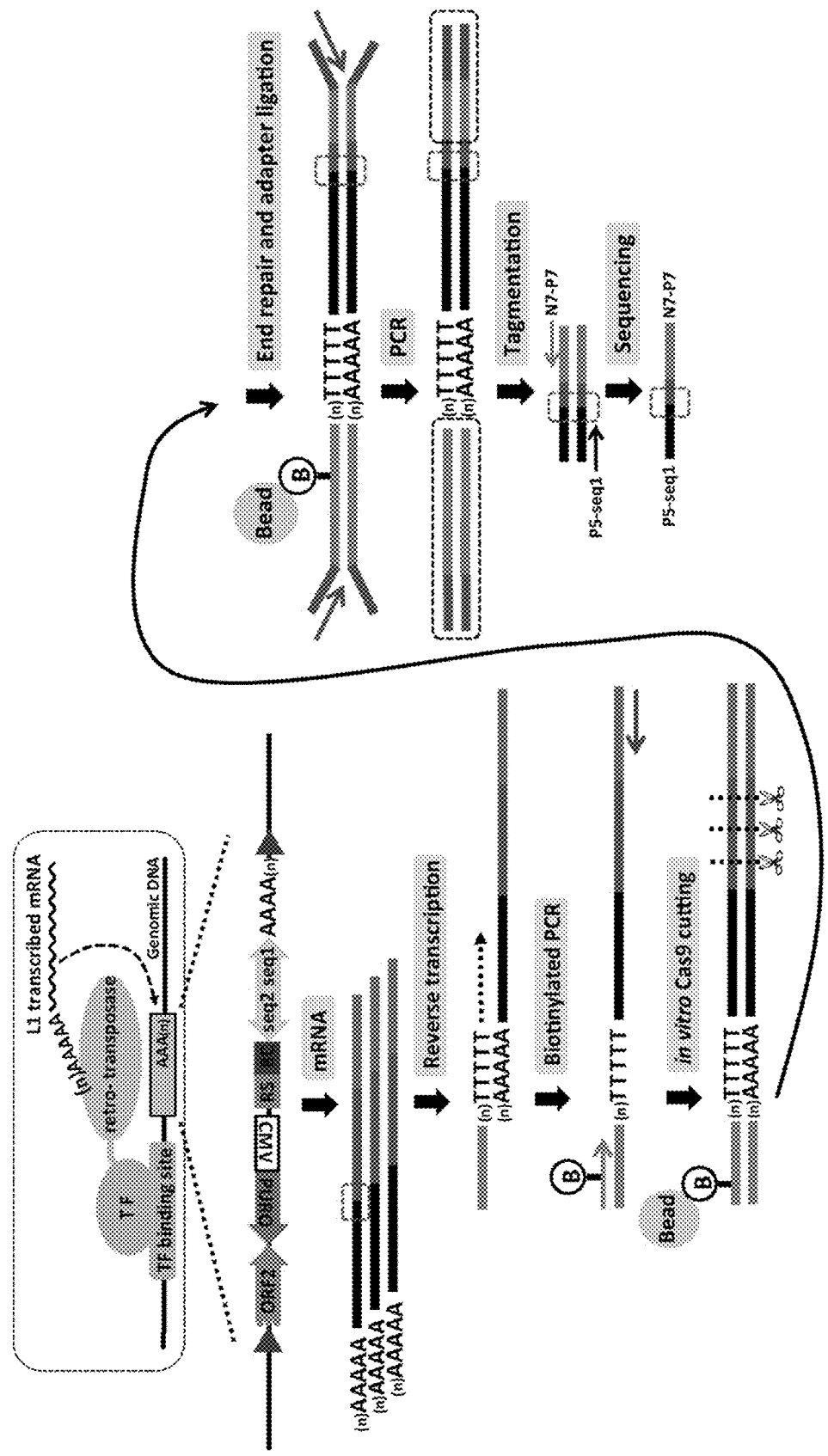
FIG. 24 is a recovery protocol for a self-reporting L1 transposon where unwanted transposon DNA is removed by Cas9 cutting. This is achieved by performing the following steps:
  (a) capturing the biotinylated PCR product on streptavidin-coated magnetic beads
  (b) optionally, tailing the ends of the PCR product with a dideoxynucleotide (ddNTP)
  (c) incubating the PCR products in vitro with Cas9 and guide RNAs (gRNAs) to specifically cut the unwanted transposon sequence
  (d) end repairing, A-tailing, and ligating Y-adapters to the cut PCR products "on bead"
  (e) amplifying by PCR with a primer specific for the Y-adapter and a primer specific to the universal sequence
  (f) purifying the resulting PCR product and proceeding with step (iv).

This example describes the development and use of an inducible LINE1 Calling Cards method and the identification of L1-directed SP1 binding sites (see e.g., FIG. 18-FIG. 24). This example demonstrates that retrotransposons can be used to map the binding of genome-associated proteins. FIG. 18 is a schematic depicting how the calling cards method was adapted for use with the L1 retrotransposon with DNA recovery. The Sp1 transcription factor was fused to ORF2 of the L1 transposon) in this construct (ORF2 is the L1 protein that is the equivalent of the transposase. ORF2 then cuts genomic DNA at TF binding sites and copies the RNA transposon via its reverse transcriptase activity to insert a DNA copy of the transposon in the genome. The construct shown in FIG. 18 is compatible with the DNA recover, so transposon locations are mapped by performing inverse PCR followed by Illumina sequencing. We used this protocol to recover undirected and Sp1 directed insertions of the L1 element. A genome-wide view of L1 insertions is shown in FIG. 19. We recovered a roughly equal number of insertions from the Sp1-retrotransposase fusion as with the unfused retrotransposase, demonstrating that the fusion does not significantly impair retrotransposase activity (see e.g., FIG. 20, top panel). Furthermore, the Sp1-retrotranspose fusion deposits significantly more transposons into promoters, 5' UTRs and CpG islands, consistent with Sp1's known binding preferences for these regions of the genome (see e.g., FIG. 20, bottom panel). Sp1 directed insertion also occur near Sp1 motifs more often than expected by chance (see e.g., FIG. 21). FIG. 22 provides an example of a known Sp1 binding site, demonstrating the concordance of ChIPseq signal, L1 calling cards directed by Sp1, and piggyBac calling cards directed by Sp1. Together, these data demonstrate that retrotransposon insertions are significantly enriched near Sp1 binding sites.

Like the piggyBac transposon, the activity of the L1 can be regulated by a chemical inducer molecule, as demonstrated in FIG. 23, where transpositions are recovered only in the presence of an inducer molecule when a degradation domain is fused to the ORF1 protein of L1.

For this proof-of-principle experiment, we mapped L1 transposition events using a DNA-based recovery method. But L1 SRTs can also be recovered from the cellular RNA. To do so, one would perform performing the following steps, shown in FIG. 24:

(g) capturing the biotinylated PCR product on streptavidin-coated magnetic beads (h) optionally, tailing the ends of the PCR product with a dideoxynucleotide (ddNTP)

(i) incubating the PCR products in vitro with Cas9 and guide RNAs (gRNAs) to specifically cut the unwanted transposon sequence (j) end repairing, A-tailing, and ligating Y-adapters to the cut PCR products "on bead"

(k) amplifying by PCR with a primer specific for the Y-adapter and a primer specific to the universal sequence (l) purifying the resulting PCR product and proceeding with step (iv).

Example 4: Tracing Cellular Lineages with Single Cell Calling Cards (scCCs)

This example describes how to infer phylogenetic relatedness of terminal cell fates from single cell calling cards data.

Calling cards are permanent and preserved through mitosis. Each insertion serves as a marker of clonal identity and different patterns of insertions in terminal cell types can be used to reconstruct phylogenetic relationships within a complex tissue.

piggyBac transpositions along a known lineage tree are computationally simulated and then genealogical relationships between individual cells are inferred from insertion site information alone. This will demonstrate feasibility as well as identify the optimal transposition rate to maximize accuracy of the inferred phylogenetic tree. Using an inducible piggyBac transposase with titratable activity, an in vitro lineage tracing experiment can be performed and the ability of computational methods to reconstruct lineage relationships is demonstrated in this example, wherein those lineages are connected to transcriptionally distinct terminal cell fates.

Natural transposition events are already used to infer phylogenetic relationships between species. Herein is described a similar kind of analysis but at cellular, instead of geologic, time scales. The single cell calling cards protocol established in section (I) can be re-used for this study. Whereas (I) relies on TF-directed piggyBac transposases, (11) uses wild-type, undirected transposases that can integrate anywhere in the genome. Each insertion event can be thought of as a lineage-specific barcode; the content and distribution of lineage barcodes can be used to infer somatic phylogenies. By performing single cell calling cards on a heterogeneous population of cells, novel cell types can be identified and their genealogical context reconstructed at the same time.

Figure 25:
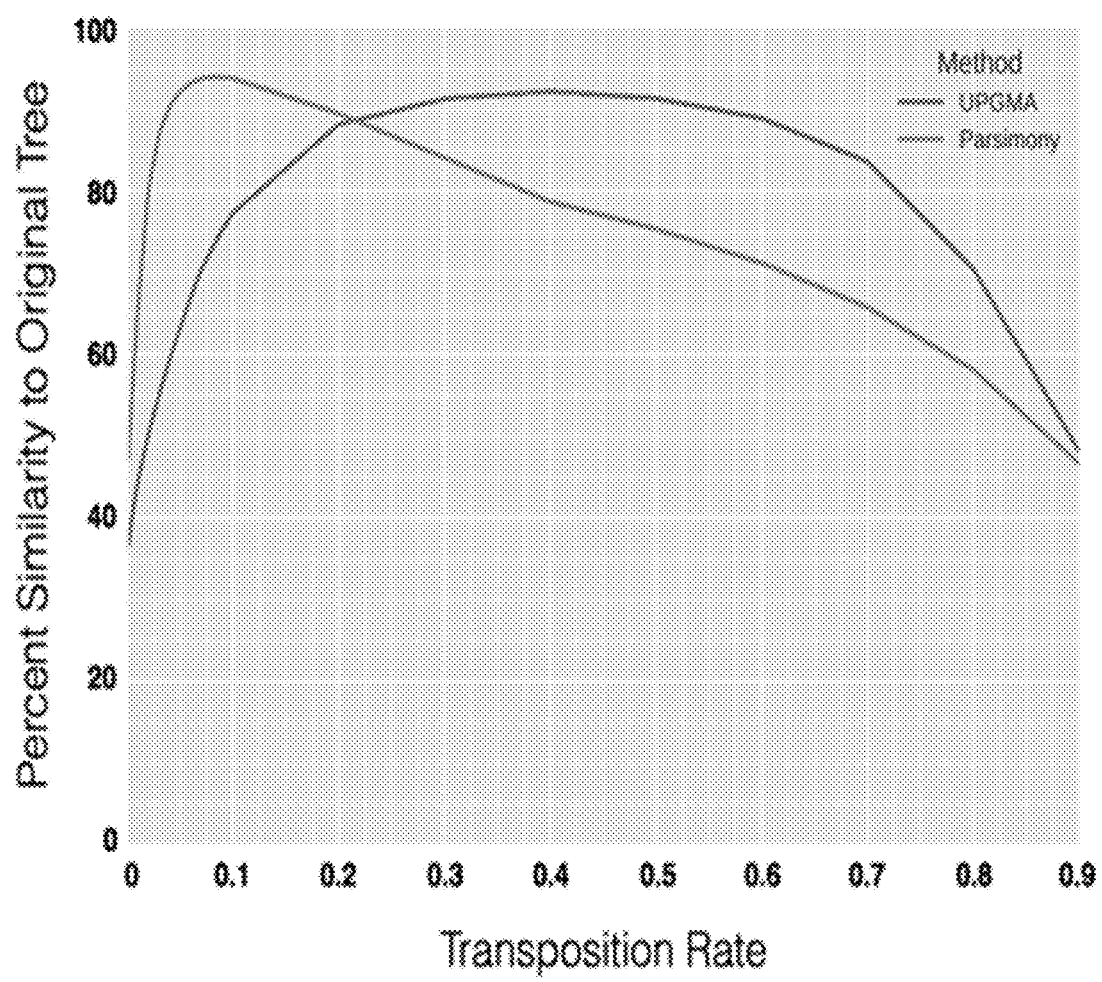
FIG. 25 is a graph showing percent similarity of inferred trees to the original tree as a function of transposition rate. Green: parsimony-based reconstruction; blue: UPGMA reconstruction. Data represent the mean of 1000 replicates.

Demonstrate Feasibility by Reconstructing Phylogenies from Computational Simulations of Single Cell Calling Cards Herein is described the design of software that can simulate single cell calling card insertions across a monoclonal population. Every replicate randomly samples cells from a 20-generation bifurcating genealogy. This subset of cells has a known phylogeny. The program then simulates transposition of self-reporting transposons along the known tree. For these purposes, the program assumes there are 1000 self-reporting donors distributed in the genome, which is a reasonable upper limit for in vitro recording. The program then traverses the known tree and at every cell division, a subset of donors transpose, proportional to the mutation rate. After each round of mutation, the transposons are copied down to each daughter cell, and the process repeats until the end of the tree is reached. The state of the transposons in each descendant serve as discrete markers of identity and are input for a parsimony-based tree inference program. Lastly, the relationship between mutation rate and inference accuracy is plotted to find the optimal transposition rate per generation. Data shown in FIG. 25, which were derived from a simpler model, suggests this kind of analysis can recreate trees with high accuracy. Reconstruction accuracy is on the y-axis and ranges from 0 to 100%, while transposition rate is along the x-axis.

Figures 26A, 26B:
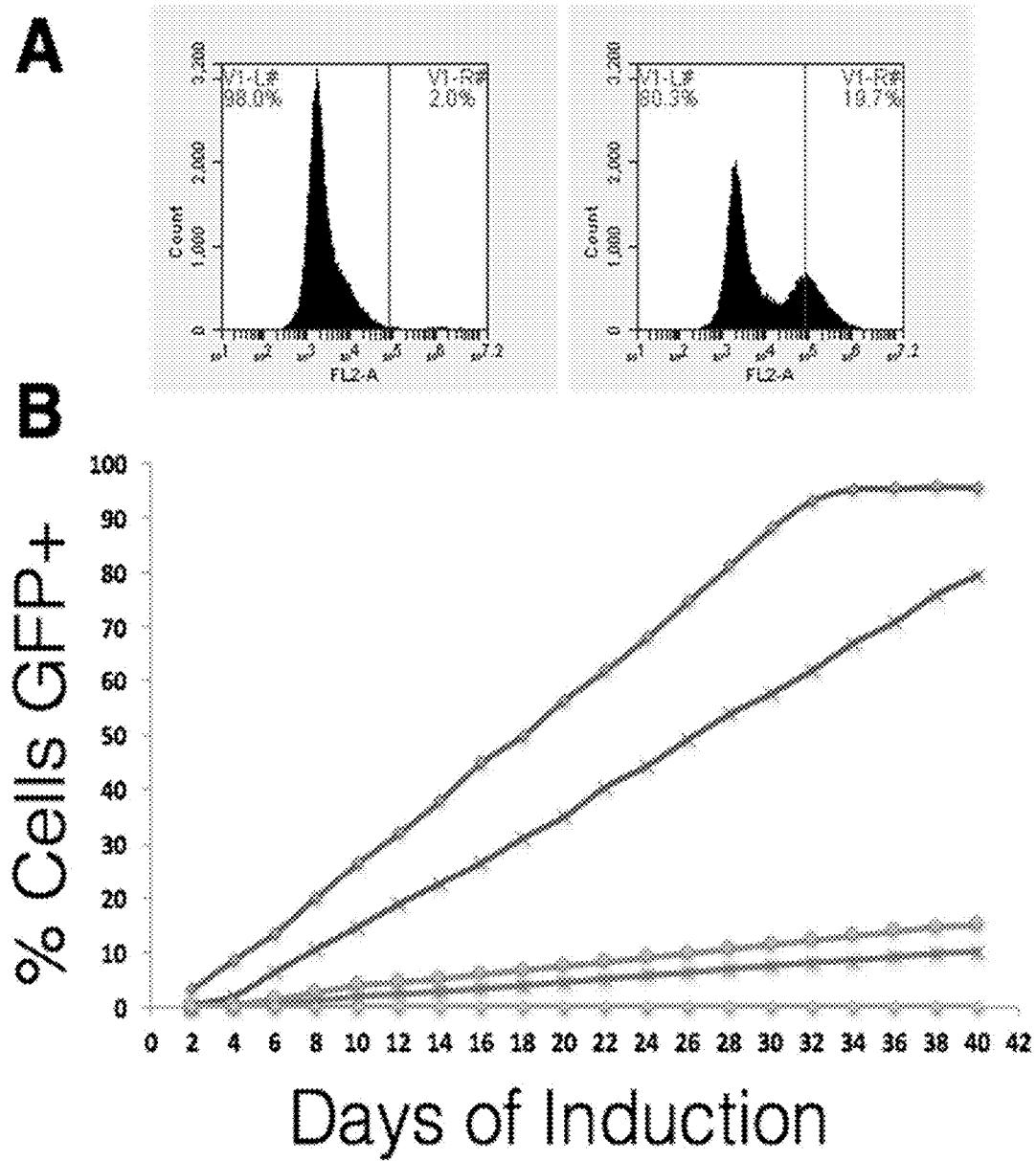
FIG. 26A-FIG. 26B is a series of graphs demonstrating that the rate of transposon insertion by a transposase-degradation domain fusion can be controlled by titrating the amount of inducer present.

Design Self-Reporting Calling Card Donors Suitable for Estimating Transposition Rates With DNA-based calling cards, a fluorescent reporter construct split by a piggyBac donor is used; when transposition occurs, the original reading frame is restored and fluorescence can be detected. A similar effect can be achieved with RNA by placing a fluorescent protein inside the self-reporting transposon and a self-cleaving hammerhead ribozyme sequence downstream of the terminal repeat. When this construct is transfected without transposase, a unimodal fluorescence distribution is observed (see e.g., FIG. 26A, left) due to rapid degradation of the transcript. Addition of a transposase creates a bimodal fluorosase distribution (see e.g., FIG. 26A, right), which implies genomic integration of the donor into in a proportion of the cells. By measuring the percent of cells in the rightmost peak over time (see e.g., FIG. 26B) and using Poisson statistics, the rate of transposition per cell division can be estimated. HEK293T cells are transfected with the self-reporting fluorescent transposon with ribozyme as well as an inducible piggyBac transposase. This cell line is cultured with different concentrations of inducers and transposition rate is estimated based on the fraction of cells that show increased fluorescence.

Given the early computational results, it is expected that a more refined simulation will not only validate feasibility but also show better performance across a range of transposition rates. The in vitro lineage tracing experiment should result in a tree that matches the order in which the populations were split. The tree inferred from the in vitro neural differentiation protocol should show the oligodendrocyte lineage clustering closer to astrocytes than astrocytes, which would corroborate known lineage relationships during motor neuron development.

Potential Pitfalls, Alternative Approaches, and Future Directions

The piggyBac transposase uses a cut-and-paste mechanism. If the transposition rate is too high, lineage-specific insertions acquired early in differentiation may re-transpose later and shuffle around in the genome. This increases noise and could hamper phylogenetic reconstruction. The newly reconstructed replicative transposase Helraiser effectively functions via a copy-paste mechanism. Thus, two cells that had distantly split from a progenitor should share few insertions, while very closely related cells should share almost all insertions. Parsimony-based methods are notoriously slow and may be impossible to use with thousands of single cell data. Distance-based inferences, like UPGMA, or probabilistic inference algorithms, can run in less time. Lastly, Drop-seq is limited to collecting ~10% of a cell's transcripts, which may cause drop-out of SRTs and loss of lineage-specific information. Methods like FACS-seq could be used, which sort live cells into individual wells of a 96-well plate. Barcoded RNA-seq library preparation is then performed inside each well. This technique offers greater transcript capture rates than Drop-seq and provides a more complete representation of a cell's transcriptome. Successful completion of this study should empower investigators with the tools necessary for reconstructing the developmental history of complex tissues in situ.

What is claimed is:

1. A self-reporting transposon (SRT) construct comprised of a transposon containing transposon DNA and at least one promoter; wherein the promoter is capable of driving transcription of DNA through at least one transposon end after the SRT construct is inserted into genomic DNA so that a portion of the transposon DNA, the at least one transposon end, and genomic DNA flanking the transposon end is transcribed into RNA; and wherein the transposon does not contain a poly-adenylation (poly-A) termination signal in the transcribed region.

2. The SRT construct of claim 1, wherein the promoter is an inducible promoter.

3. The SRT construct of claim 2, wherein the inducible promoter is capable of being induced by a chemical inducer and light.

4. The SRT construct of claim 1, wherein the promoter comprises an EF1α promoter, a CAG promoter, a PGK promoter, a Tet-on or Tet-off promoter, a T7 promoter, or a CMV promoter.

5. The SRT construct of claim 1, wherein the promoter drives expression of a reporter gene incorporated in the transposon.

6. The SRT construct of claim 5, wherein the reporter gene is selected from the group consisting of:
   a gene encoding a fluorescent protein;
   a gene capable of use as a selectable marker by conferring resistance to a chemical agent that kills eukaryotic or prokaryotic cells; and
   a gene encoding an enzyme capable of converting a chemical substrate into a colorimetric reporter, a luminescent reporter, or a fluorescent reporter.

7. The SRT construct of claim 6, wherein the gene encoding a fluorescent protein comprises green fluorescent protein, tdTomato, eGFP, or eCFP.

8. The SRT construct of claim 6, wherein the gene capable of use as a selectable marker comprises puromycin N-acetyltransferase, an aminoglycoside 3' phosphotransferase gene encoded by Tn5 and Tn601, or hygromycin phosphotransferase.

9. The SRT construct of claim 1, wherein the transposon encodes a Woodchuck Hepatitis Virus (WHP) Posttranscriptional Regulatory Element (WPRE).

* * * * *